(12) United States Patent
Casale et al.

(10) Patent No.: US 8,580,783 B2
(45) Date of Patent: Nov. 12, 2013

(54) [1,2,4]TRIAZOLO [1,5-C]PYRIMIDINE DERIVATIVES AS HSP90 MODULATORS

(75) Inventors: Elena Casale, Somma Lombardo (IT); Francesco Casuscelli, Dairago (IT); Claudio Dalvit, Milan (IT); Paolo Polucci, Cassina Rizzardi (IT); Fabio Zuccotto, Milan (IT)

(73) Assignee: Nerviano Medical Sciences S.r.l., Nerviano (MI) (IT)

( * ) Notice: Subject to any disclaimer, the term of this patent is extended or adjusted under 35 U.S.C. 154(b) by 0 days.

(21) Appl. No.: 13/394,255

(22) PCT Filed: Sep. 3, 2010

(86) PCT No.: PCT/EP2010/062930
§ 371 (c)(1),
(2), (4) Date: Apr. 3, 2012

(87) PCT Pub. No.: WO2011/029775
PCT Pub. Date: Mar. 17, 2011

(65) Prior Publication Data
US 2012/0184546 A1 Jul. 19, 2012

(51) Int. Cl.
*A61K 31/519* (2006.01)
*A61K 31/5377* (2006.01)
*C12N 9/99* (2006.01)
*A61P 35/00* (2006.01)

(52) U.S. Cl.
USPC .................. 514/233.2; 514/267; 514/252.16; 544/251; 544/115; 435/184

(58) Field of Classification Search
USPC .......... 514/233.2, 267, 252.16; 544/115, 251; 435/184
See application file for complete search history.

(56) References Cited

U.S. PATENT DOCUMENTS

2008/0096903 A1 4/2008 Chen et al.
2009/0163545 A1 6/2009 Goldfarb

FOREIGN PATENT DOCUMENTS

WO  WO 2005/018532       3/2005
WO  WO 2005/018532 A2    3/2005

OTHER PUBLICATIONS

Brough P.A. et al., "3-(5-Chloro-2,4-Dihydroxyphenyl)-Pyrazole-4-Carboxamides as Inhibitors of the Hsp90 Molecular Chaperone", *Bioorganic & Medicinal Chemistry Letters* 15(23):5197-5201 (Dec. 1, 2005).
Jolly C. et al., "Role of the Heat Shock Response and Molecular Chaperones in Oncogenesis and Cell Death", *Journal of the National Cancer Institute* 92(19):1564-1572 (Oct. 4, 2000).
Ried et al., "Reactions with Aminoguanidine. I. S-Triazolo[1,5-c] Quinazoline Derivatives", *Chemische Berichte* 101(6):2106-2116 (1968).
Montalbetti C.A.G.N. et al., "Amide Bond Formation and Peptide Coupling", *Tetrahedron* 61:10827-10852 (2005).
Borch R.F. et al., "The Cyanohydridoborate Anion as a Selective Reducing Agent", *Journal of the American Chemical Society* 93(12):2897-2904 (Jun. 16, 1971).
Bader H. et al., "Nucleophilic Displacements of Activated Fluorine in Aromatic.Compounds", *Journal of Organic Chemistry* 31(7):2319-2321 (Jul. 1966).
Bader H. et al., "Nucleophilic Displacements of Activated Fluorine in Aromatic Compounds", *Journal of Organic Chemistry* 31(7):2319-2321 (Jul. 1966).

*Primary Examiner* — San-Ming Hui
*Assistant Examiner* — Kathrien Cruz
(74) *Attorney, Agent, or Firm* — Scully, Scott, Murphy & Presser, P.C.

(57) ABSTRACT

The present invention relates to [1,2,4]triazolo[1,5-c]pyrimidine derivatives of formula (I) which inhibit the activity of Heat Shock Protein Hsp90. The compounds of the invention are therefore useful in treating proliferative diseases such as cancer and neurodegenerative diseases. The present invention also provides processes for preparing these compounds, methods of treating diseases and the pharmaceutical compositions comprising these compounds.

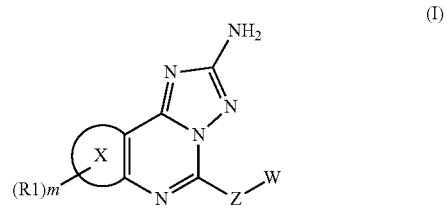

11 Claims, No Drawings

[1,2,4]TRIAZOLO [1,5-C]PYRIMIDINE DERIVATIVES AS HSP90 MODULATORS

The present invention relates to [1,2,4]triazolo[1,5-c]pyrimidine derivatives which inhibit the activity of Heat Shock Protein Hsp90. The compounds of the invention are therefore useful in treating proliferative diseases such as cancer and neurodegenerative diseases. The present invention also provides processes for preparing these compounds, pharmaceutical compositions comprising them, methods of treating diseases and the pharmaceutical compositions comprising these compounds.

The current target therapies for the treatment of cancer are based on the identification of specific proteins that drive tumour progression, and on the identification of a specific agent capable of antagonizing the effect of this protein. Most of the efforts of the pharma industry are directed towards a very limited number of well validated protein targets. A common drawback is the arising of drug resistant mutations frequently found in cancer patients that are treated with these specific inhibitors. Recently, the common opinion is that the simultaneous block of signalling pathways involved in cancer progression is expected to determine a better anti-tumour efficacy, and also a lower probability to develop resistance. Hsp90 belongs to a small family of proteins (GHKL, from DNA Gyrase, Hsp90, histidine Kinase, mutL) sharing in common a very specific C shaped mode of binding to ATP (Bergerat fold). Hsp90 is one of the most abundant proteins in cells, essential for viability in eukaryotes. The human cell contains four isoforms of Hsp90: the cytosolic β-isoform, which is constitutively expressed, the inducible α-form, GRP94/gp96 in the endoplasmatic reticulum, and the mitochondrial TRAP1/hsp75. The α- and the β-form show 85% sequence identity.

Hsp90 is a key component of a chaperone machinery, it catalyzes the folding and quality control of proteins, called Hsp90 clients, in both normal cells and also under stress conditions. The chaperone activity, strictly dependent on the ATPase activity, is tightly regulated by the binding of other regulatory co-chaperones.

There are strong evidences that in disease conditions, such as cancer or other proliferative diseases, Hsp90 becomes critical, due to the mutation or overexpression of specific oncogenes or also because tumors often have an overload of misfolded proteins that leads to an increased requirement of chaperone function.

Structurally Hsp90 is an homodimer made of three main structured domains: an N terminal domain very conserved, the ATPase domain, a middle domain and a C terminal domain. The N and C terminal domains can bind ATP. Most of the currently known inhibitors such as geldanamycin, radicicol, diarylpyrazoles and purine derivatives show an ATP competitive binding to the N terminal ATP binding site, while novobiocin is the prototype of the inhibitors binding to the C terminal pocket.

At the moment, there is an increasing number of reported Hsp90 clients (Jolly, et al., J. Natl. Cancer Inst. 92; 1564-1572 (2000), belonging to the family of kinases (Her2, B-RAF V600E, bcr-Abl, Flt3, NPM-ALK, Akt, Npm-Alk, ZAP-70), transcription factors (p53, HIF) telomerase, other chaperones, most of them strictly related with cancer progression. Hsp90 inhibition impairs the capacity to fold or stabilize its client proteins, leading to the proteosomal dependent degradation of these unfolded proteins. The degradation of these client proteins is frequently used as a marker of Hsp90 inhibition, typically used is the degradation of Her2 after compound treatment in Her2 overexpressing cells, such as BT474 breast cancer cells.

A big wave of research in the field of Hsp90 inhibitors was driven initially by the evidence that the natural compound geldanamycin could actually block the proliferation of multiple tumour cells, by competitively binding to the N terminal ATP binding site and inhibiting the Hsp90 ATPase activity and function. Surprisingly, this compound was not active in normal cells, may be because Hsp90 is present in an active complex (with high affinity to geldanamycin) only in tumour cells (Kamal et al.). Another potential reason for the selective sensitivity for tumours is the tumour retention that many HSP90 inhibitors show.

Tanespimycin (17-AAG), a semisynthetic derivative of geldanamycin, together with other related derivatives (alvespimycin, 17-DMAG, IPI-504) is under intense clinical evaluation, but the efficacy appear to be limited by a number of factors: cumbersome formulation, dependence on metabolism to generate the active metabolite, lack of patient enrichment, hepatic toxicity possibly related to the quinone moiety. This paved the way to an intense effort for the identification of second generation of Hsp90 inhibitors with a better drug-like profile and better tolerability. This led to the identification of purine derivatives and diaryl-resorcinol derivatives.

The major cause of neurodegenerative diseases such as Alzheimer's, Parkinson's, Huntington's, and prion disease is the accumulation of misfolded proteins that result in plaque formation. These misfolded proteins rely upon molecular chaperones (Hsp70, Hsp40, etc.) for rematuration, disaggregation, and resolubilization of protein aggregates. The heat shock proteins have been shown to provide this function in various cell culture models. Hsps can be induced by HSF1, which is tightly regulated by Hsp90 in normal cells. It has been demonstrated that Hsp90 inhibitors such as geldanamycin and the 17-AAG derivative can disrupt this interaction and lead to Hsp induction, resulting in neuroprotective activities and the resolubilization and disaggregation of misfolded proteins. Hsp90 overexpression can significantly decrease the accumulation of misfolded proteins, which are responsible for Alzheimer's, in fact it has been demonstrated an inverse relationship between aggregated tau and Hsp70/90 levels. Abnormal tau aggregation can be diminished (through degradation) by the overexpression of Hsp70, Hsp27, and Hsp40 which is triggered by the inhibition of Hsp90. Application of Hsp90 inhibitors for the management of Parkinson'disease finds ground on the in vivo effect of GDA on 1-methyl-4-phenyl-1,2,3,6-tetrahydropyridine (MPTP)-induced neurotoxicity of a mouse model for PD. GDA protected the neurons from toxicity caused by MPTP, which was closely linked to increased Hsp70 levels. In addition, it has been also shown that Hsp90 overexpression can significantly decrease the accumulation of misfolded proteins, which are responsible for motor impairments, multiple sclerosis, spinal and bulbar muscular atrophy and other diseases.

Triazolopyrimidine compounds binding to purine receptor for the treatment of CNS disorders have been disclosed in WO2005018532 in the name of Actar Ab.

The synthesis of 5-ethyl-[1,2,4]triazolo[1,5-c]quinazolin-2-ylamine is described in Chemische Berichte (1968), 101 (6), 2106-16, no biological activity is reported for this compound; 5-n-propyl-[1,2,4]triazolo[1,5-c]quinazolin-2-ylamine and 5-benzyl-[1,2,4]triazolo[1,5-c]quinazolin-2-ylamine as lifespan-altering compounds are disclosed in US2009163545 in the name of University of Rochester.

It has been found that compounds of formula (I) described below, are Hsp90 inhibitors and are thus useful in therapy as antitumor and antineurodegenerative agents.

Accordingly, a first object of the present invention is to provide a compound of the formula (I):

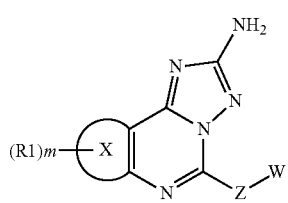

(I)

wherein:

m is 0, 1 or 2;

X is phenyl, naphtyl, pyridine, furan or thiophene;

any R1, if present, is independently halogen, trifluoromethyl, cyano, nitro, CONHRa, ORa, NRbRa, NHCORa, NHSO$_2$Ra, SO$_2$Rd, COORe or an optionally substituted group selected from linear or branched C$_1$-C$_7$ alkyl, C$_2$-C$_7$ alkenyl, C$_2$-C$_7$ alkynyl, C$_3$-C$_8$ cycloalkyl, C$_4$-C$_8$ cycloalkenyl and C$_4$-C$_8$ heterocyclyl, wherein Ra is hydrogen, trifluoromethyl or an optionally substituted group selected from linear or branched C$_1$-C$_7$ alkyl, C$_2$-C$_7$ alkenyl, C$_2$-C$_7$ alkynyl, C$_3$-C$_8$ cycloalkyl, C$_4$-C$_8$ cycloalkenyl, C$_4$-C$_8$ heterocyclyl, aryl and heteroaryl;

Rb and Ra, the same or different, are hydrogen or an optionally substituted group selected from linear or branched C$_1$-C$_7$ alkyl, C$_2$-C$_7$ alkenyl, C$_2$-C$_7$ alkynyl, C$_3$-C$_8$ cycloalkyl, C$_4$-C$_8$ cycloalkenyl, C$_4$-C$_8$ heterocyclyl, aryl and heteroaryl or Rb and Rc together with the nitrogen atom to which they are bonded form an optionally substituted heterocyclyl group comprising oxygen, sulfur or nitrogen atom, Rd is an optionally substituted linear or branched C$_1$-C$_7$ alkyl, Re is hydrogen or an optionally substituted linear or branched C$_1$-C$_7$ alkyl;

W is a substituted linear or branched C$_1$-C$_7$ alkyl or an optionally substituted aryl or heteroaryl, optionally fused with C$_3$-C$_8$ cycloalkyl or C$_4$-C$_8$ heterocyclyl;

Z is CH$_2$, CH(OR2) or CH(NHR3), wherein

R2 is hydrogen or an optionally substituted linear or branched C$_1$-C$_7$ alkyl, R3 is hydrogen or COR4, wherein R4 is O—C$_1$-C$_7$ alkyl, and pharmaceutically acceptable salts thereof, provided that 5-benzyl-[1,2,4]triazolo[1,5-c]quinazolin-2-ylamine is excluded.

In particular, compounds of the formula (I) are:

[1,2,4]triazolo[1,5-c]quinazoline derivatives of formula (I)A,

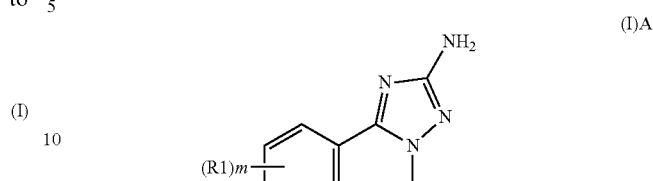

(I)A that is compounds of formula (I) wherein X is phenyl and m, R1, Z and W are as defined above; benzo[g], benzo[f], benzo[h][1,2,4]triazolo[1,5-c]quinazoline derivatives of formula (I)B1, (I)B2 and (I)B3 respectively

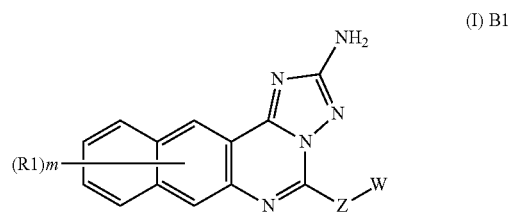

(I) B1

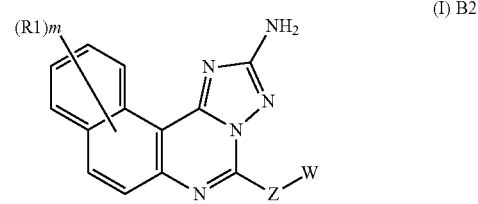

(I) B2

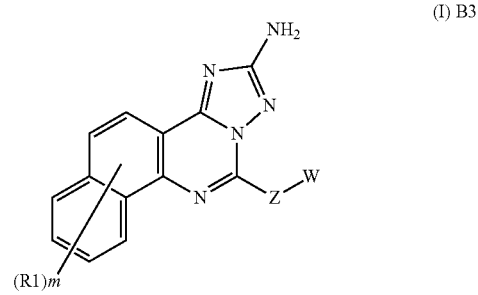

(I) B3 that are compounds of formula (I) wherein X is naphtyl and m, R1, Z and W are as defined above; pyrido[3,2-e], pyrido[4,3-e], pyrido[3,4-e], pyrido[2,3-e][1,2,4]triazolo[1,5-d]pyrimidine derivatives of formula (I)C1, (I)C, (I)C3 and (I)C4 respectively

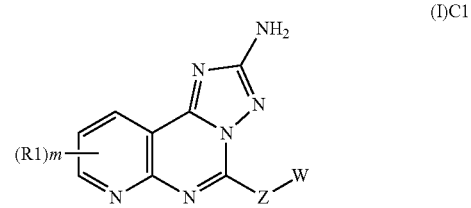

(I)C1

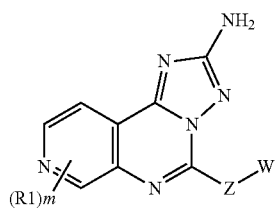
(I)C2

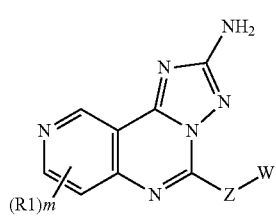
(I)C3

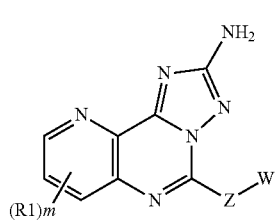
(I)C4 that are compounds of formula (I) wherein X is pyridine and m, R1, Z and W are as defined above; furo[3,2-e], furo[2,3-e], furo[3,4-e][1,2,4]triazolo[1,5-c]pyrimidine derivatives of formula (I)D1, (I)D2 and (I)D3 respectively

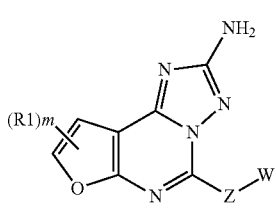
(I)D1

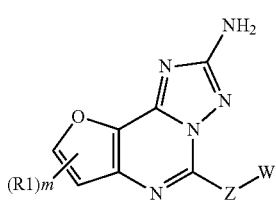
(I)D2

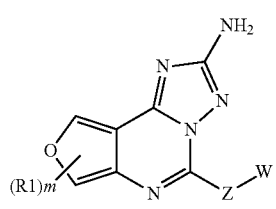
(I)D3 that are compounds of formula (I) wherein X is furan and m, R1, Z and W are as defined above and thieno[3,2-e], thieno[2,3-e], thieno[3,4-e][1,2,4]triazolo[1,5-c]pyrimidine derivatives of formula (I)E1, (I)E2 and (I)E3 respectively

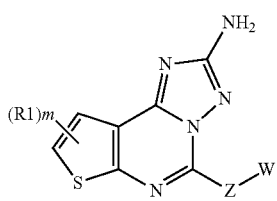
(I)E1

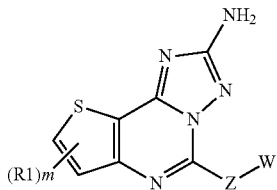
(I)E2

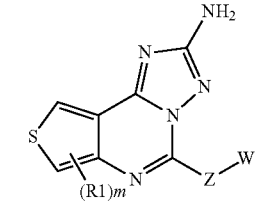
(I)E3 that are compounds of formula (I) wherein X is thiophene and m, R1, Z and W are as defined above.

As stated above, the compounds of the present invention are potent Hsp90 inhibitors and are thus useful in anticancer and neurodegenerative diseases therapy.

The present invention also provides processes of synthesizing the [1,2,4]triazolo[1,5-c]pyrimidine derivatives of formula (I) prepared through a process consisting of standard synthetic transformations.

The present invention also provides a method for treating diseases mediated by Hsp90 protein.

A preferred method of the present invention is to treat a disease mediated by Hsp90 protein selected from the group consisting of cancer and neurodegenerative disorders.

Another preferred method of the present invention is to treat specific types of cancer including but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage including leukaemia, acute lymphocytic leukaemia, acute lymphoblastic leukaemia, B-cell lymphoma, T-cell-lymphoma, Hodgkin's lymphoma, non-Hodgkin's lymphoma, hairy cell lymphoma and Burkitt's lymphoma; hematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

Another preferred method of the present invention is to treat specific types of neurodegenerative disorders including but not limited to: Alzheimer's, Parkinson's, Huntington's diseases, multiple sclerosis and spinal and bulbar muscular atrophy.

The present invention further provides a method of treatment comprising a compound of formula (I) in combination with radiation therapy or chemotherapy regimen for simultaneous, separate or sequential use in anticancer therapy.

Moreover the invention provides an invitro method for inhibiting Hsp90 protein activity which comprises contacting the said protein with an effective amount of a compound of formula (I).

The present invention also provides a pharmaceutical composition comprising one or more compounds of formula (I) or a pharmaceutically acceptable salt thereof and a pharmaceutically acceptable excipient, carrier or diluent.

The present invention also provides a pharmaceutical composition comprising a compound of formula (I) in combination with known cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrix metalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

Additionally, the invention provides a product or kit comprising a compound of formula (I) or a pharmaceutically acceptable salt thereof, as defined above, or pharmaceutical compositions thereof and one or more chemotherapeutic agents, as a combined preparation for simultaneous, separate or sequential use in anticancer therapy.

In yet another aspect the invention provides a compound of formula (I) or a pharmaceutically acceptable salt thereof, as defined above, for use as a medicament.

Moreover the invention provides the use of a compound of formula (I) or a pharmaceutically acceptable salt thereof, as defined above, in the manufacture of a medicament with antitumor activity.

Finally, the invention provides a compound of formula (I) or a pharmaceutically acceptable salt thereof, as defined above, for use in a method of treating cancer or a neurodegenerative disorder.

Unless otherwise specified, when referring to the compounds of formula (I) per se as well as to any pharmaceutical composition thereof or to any therapeutic treatment comprising them, the present invention includes all of the isomers, tautomers, hydrates, solvates, complexes, N-oxides and pharmaceutically acceptable salts of the compounds of this invention.

N-oxides are compounds of formula (I) wherein on one of the nitrogen atoms of the molecule there is an oxygen atom tethered through a dative bond. If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases wherein compounds may exist in tautomeric forms, such as keto-enol tautomers, each tautomeric form is contemplated as being included within this invention whether existing in equilibrium or predominantly in one form.

Pharmaceutically acceptable salts of the compounds of formula (I) include the acid addition salts with inorganic or organic acids, e.g., nitric, hydrochloric, hydrobromic, sulfuric, perchloric, phosphoric, acetic, trifluoroacetic, propionic, glycolic, fumaric, lactic, oxalic, malonic, malic, maleic, tartaric, citric, benzoic, cinnamic, mandelic, methanesulphonic, isethionic and salicylic acid. Pharmaceutically acceptable salts of the compounds of formula (I) also include the salts with inorganic or organic bases, e.g., alkali or alkaline-earth metals, especially sodium, potassium, calcium ammonium or magnesium hydroxides, carbonates or bicarbonates, acyclic or cyclic amines, preferably methylamine, ethylamine, diethylamine, triethylamine, piperidine and the like.

With the term halogen atom we intend a fluorine, chlorine, bromine or iodine atom.

With the term "linear or branched $C_1$-$C_7$ alkyl", we intend any of the groups such as, for instance, methyl, ethyl, n-propyl, isopropyl, n-butyl, isobutyl, tert-butyl, sec-butyl, n-pentyl, n-hexyl, and the like.

With the term "$C_2$-$C_7$ alkenyl" we intend an aliphatic $C_2$-$C_7$ hydrocarbon chain containing at least one carbon-carbon double bond and which can be straight or branched. Representative examples include, but are not limited to, ethenyl, 1-propenyl, 2-propenyl, 1- or 2-butenyl, and the like.

With the term "$C_2$-$C_7$ alkynyl" we intend an aliphatic $C_2$-$C_7$ hydrocarbon chain containing at least one carbon-carbon triple bond and which can be straight or branched. Representative examples include, but are not limited to, ethynyl, 1-propynyl, 2-propynyl, 1- or 2-butynyl, and the like.

With the term "$C_3$-$C_8$ cycloalkyl" we intend, unless otherwise provided, 3- to 8-membered all-carbon monocyclic ring, which may contain one or more double bonds but does not have a completely conjugated π-electron system. Examples of cycloalkyl groups, without limitation, are cyclopropane, cyclobutane, cyclopentane, cyclopentene, cyclohexane, cyclohexene and cyclohexadiene.

With the term "$C_4$-$C_8$ heterocyclyl" we intend a 4- to 8-membered, saturated or partially unsaturated carbocyclic ring where one or more carbon atoms are replaced by nitrogen, oxygen or sulfur. Non limiting examples of heterocyclyl groups are, for instance, pyrane, pyrrolidine, pyrroline, imidazoline, imidazolidine, pyrazolidine, pyrazoline, thiazoline, thiazolidine, dihydrofuran, tetrahydrofuran, 1,3-dioxolane, piperidine, piperazine, morpholine and the like.

The term "aryl" refers to a mono-, bi- or poly-carbocyclic hydrocarbon with from 1 to 4 ring systems, optionally further fused or linked to each other by single bonds, wherein at least one of the carbocyclic rings is "aromatic", wherein the term "aromatic" refers to completely conjugated π-electron bond system. Non limiting examples of such aryl groups are phenyl, α- or β-naphthyl or biphenyl groups.

The term "heteroaryl" refers to aromatic heterocyclic rings, typically 5- to 8-membered heterocycles with from 1 to 3 heteroatoms selected among N, O or S; the heteroaryl ring can be optionally further fused or linked to aromatic and non-aromatic carbocyclic and heterocyclic rings. Not limiting examples of such heteroaryl groups are, for instance, pyridyl, pyrazinyl, pyrimidinyl, pyridazinyl, indolyl, imidazolyl, thiazolyl, isothiazolyl, pyrrolyl, phenyl-pyrrolyl, furyl, phenyl-furyl, oxazolyl, isoxazolyl, pyrazolyl, thienyl, benzothienyl, isoindolinyl, benzoimidazolyl, quinolinyl, isoquinolinyl, 1,2,3-triazolyl, 1-phenyl-1,2,3-triazolyl, 2,3-dihydroindolyl, 2,3-dihydrobenzofuranyl, 2,3-dihydrobenzothiophenyl; benzopyranyl, 2,3-dihydrobenzoxazinyl, 2,3-dihydroquinoxalinyl and the like.

According to the present invention and unless otherwise provided, any of the above R1, R2, R3, R4, Ra, Rb, Ra, Rd, Re and W group may be optionally substituted, in any of their free positions, by one or more groups, for instance 1 to 6 groups, independently selected from: halogen, nitro, oxo groups (=O), cyano, $C_1$-$C_7$ alkyl, polyfluorinated alkyl, polyfluorinated alkoxy, $C_2$-$C_7$ alkenyl, $C_2$-$C_7$ alkynyl, hydroxyalkyl, aryl, arylalkyl, heteroaryl, heteroarylalkyl, $C_4$-$C_8$ heterocyclyl, heterocyclylalkyl, $C_3$-$C_8$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclylalkyloxycarbonyl-amino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate. In their turn, whenever appropriate, each of the above substituent may be further substituted by one or more of the aforementioned groups.

With the term polyfluorinated alkyl or polyfluorinated alkoxy we intend any of the above straight or branched $C_1$-$C_8$ alkyl or alkoxy groups which are substituted by more than one fluorine atom such as, for instance, trifluoromethyl, trifluoroethyl, 1,1,1,3,3,3-hexafluoropropyl, trifluoromethoxy and the like.

With the term hydroxyalkyl we intend any of the above $C_1$-$C_8$ alkyl, bearing an hydroxyl group such as, for instance, hydroxymethyl, 2-hydroxyethyl, 3-hydroxypropyl and the like.

From all of the above, it is clear to the skilled person that any group which name is a composite name such as, for instance, arylamino has to be intended as conventionally construed by the parts from which it derives, e.g. by an amino group which is further substituted by aryl, wherein aryl is as defined above.

Likewise, any of the terms such as, for instance, alkylthio, alkylamino, dialkylamino, alkoxycarbonyl, alkoxycarbonylamino, heterocyclylcarbonyl, heterocyclylcarbonylamino, cycloalkyloxycarbonyl and the like, include groups wherein the alkyl, alkoxy, aryl, $C_3$-$C_7$ cycloalkyl and heterocyclyl moieties are as defined above.

A preferred class of compounds of formula (I) is represented by compounds wherein X is phenyl, and Z, m, R1 and W are as defined above.

A more preferred class of compounds of formula (I) is represented by compounds wherein X is phenyl, Z is $CH_2$, and m, R1 and W are as defined above.

A most preferred class of compounds of formula (I) is represented by compounds wherein X is phenyl, Z is $CH_2$, W is an optionally substituted aryl, optionally fused with $C_3$-$C_8$ cycloalkyl or $C_4$-$C_8$ heterocyclyl, and m and R1 are as defined above.

Specific compounds (cpd.) of the invention are listed below:
1. 5-(3-bromo-4-methoxybenzyl)[1,2,4]triazolo[1,5-c]quinazolin-2-amine,
2. 5-[3-(2-furyl)-4-methoxybenzyl][1,2,4]triazolo[1,5-c]quinazolin-2-amine,
3. 4-[(2-amino[1,2,4]triazolo[1,5-c]quinazolin-5-yl)methyl]-2-bromophenol,
4. 5-(1,3-benzodioxol-5-ylmethyl)-8-nitro[1,2,4]triazolo[1,5-c]quinazolin-2-amine,
5. tert-butyl[(S)-(2-amino[1,2,4]triazolo[1,5-c]quinazolin-5-yl)(phenyl)methyl]carbamate,
6. 5-(1,3-benzodioxol-5-ylmethyl)[1,2,4]triazolo[1,5-c]quinazoline-2,8-diamine,
7. 2-amino-5-(1,3-benzodioxol-5-ylmethyl)[1,2,4]triazolo[1,5-c]quinazoline-8-sulfonamide,
8. (R)-(2-amino[1,2,4]triazolo[1,5-c]quinazolin-5-yl)(phenyl)methanol,
9. 5-(2,3-dihydro-1,4-benzodioxin-6-ylmethyl)[1,2,4]triazolo[1,5-c]quinazolin-2-amine,
10. 5-[2-(benzyloxy)benzyl][1,2,4]triazolo[1,5-c]quinazolin-2-amine,
11. 5-(2,3-dihydro-1-benzofuran-5-ylmethyl)[1,2,4]triazolo[1,5-c]quinazolin-2-amine,
12. (S)-(2-amino[1,2,4]triazolo[1,5-c]quinazolin-5-yl)(phenyl)methanol,
13. tert-butyl[(R)-(2-amino[1,2,4]triazolo[1,5-c]quinazolin-5-yl)(phenyl)methyl]carbamate,
14. 2-amino-5-(1,3-benzodioxol-5-ylmethyl)[1,2,4]triazolo[1,5-c]quinazoline-9-carbonitrile,
15. 5-(1,3-benzodioxol-5-ylmethyl)-8-fluoro[1,2,4]triazolo[1,5-c]quinazolin-2-amine,
16. 5-[(R)-amino(phenyl)methyl][1,2,4]triazolo[1,5-c]quinazolin-2-amine,
17. 5-(1,3-benzodioxol-5-ylmethyl)-8-(methylsulfonyl)[1,2,4]triazolo[1,5-c]quinazolin-2-amine,
18. 5-[(6-iodo-1,3-benzodioxol-5-yl)methyl][1,2,4]triazolo[1,5-c]quinazolin-2-amine,
19. 9-(aminomethyl)-5-(1,3-benzodioxol-5-ylmethyl)[1,2,4]triazolo[1,5-c]quinazolin-2-amine,
20. 2-amino-5-(1,3-benzodioxol-5-ylmethyl)[1,2,4]triazolo[1,5-c]quinazolin-9-ol,
21. 5-[(6-bromo-1,3-benzodioxol-5-yl)methyl][1,2,4]triazolo[1,5-c]quinazolin-2-amine,
22. 2-amino[1,2,4]triazolo[1,5-c]quinazolin-5-ol,
23. 5-(1,3-benzodioxol-5-ylmethyl)-10-fluoro[1,2,4]triazolo[1,5-c]quinazolin-2-amine,
24. N-[2-amino-5-(1,3-benzodioxol-5-ylmethyl)[1,2,4]triazolo[1,5-c]quinazolin-9-yl]acetamide,
25. 5-(1,3-benzodioxol-5-ylmethyl)-8-bromo[1,2,4]triazolo[1,5-c]quinazolin-2-amine,
26. 5-(1,3-benzodioxol-5-ylmethyl)-8-morpholin-4-yl[1,2,4]triazolo[1,5-c]quinazolin-2-amine,
27. 2-amino-5-(1,3-benzodioxol-5-ylmethyl)[1,2,4]triazolo[1,5-c]quinazolin-7-ol,
28. 5-(1,3-benzodioxol-5-ylmethyl)-8-(4-methylpiperazin-1-yl)[1,2,4]triazolo[1,5-c]quinazolin-2-amine,
29. 2-{[2-amino-5-(1,3-benzodioxol-5-ylmethyl)[1,2,4]triazolo[1,5-c]quinazolin-8-yl]amino}ethanol,
30. 5-(1,3-benzodioxol-5-ylmethyl)-N~8~-(2-morpholin-4-ylethyl)[1,2,4]triazolo[1,5-c]quinazoline-2,8-diamine,
31. 5-(1,3-benzodioxol-5-ylmethyl)-N~8~-(2-pyrrolidin-1-ylethyl)[1,2,4]triazolo[1,5-c]quinazoline-2,8-diamine,
32. 5-(1,3-benzodioxol-5-ylmethyl)-N~8~-[2-(dimethylamino)ethyl][1,2,4]triazolo[1,5-c]quinazoline-2,8-diamine,
33. 5-(1,3-benzodioxol-5-ylmethyl)-N~8~-(2-methoxyethyl)[1,2,4]triazolo[1,5-c]quinazoline-2,8-diamine,
34. 5-(1,3-benzodioxol-5-ylmethyl)-10-methoxy[1,2,4]triazolo[1,5-c]quinazolin-2-amine,
35. 3-{[2-amino-5-(1,3-benzodioxol-5-ylmethyl)[1,2,4]triazolo[1,5-c]quinazolin-8-yl]amino}propan-1-ol,
36. N-8-(2-aminoethyl)-5-(1,3-benzodioxol-5-ylmethyl)[1,2,4]triazolo[1,5-c]quinazoline-2,8-diamine, 37. 5-(1,3-benzodioxol-5-ylmethyl)-8,10-diffluoro[1,2,4]triazolo[1,5-c]quinazolin-2-amine,
38. 2-{[2-amino-5-(1,3-benzodioxol-5-ylmethyl)-8-fluoro[1,2,4]triazolo[1,5-c]quinazolin-10-yl]amino}ethanol,
39. N-10-(2-aminoethyl)-5-(1,3-benzodioxol-5-ylmethyl)-8-fluoro[1,2,4]triazolo[1,5-c]quinazoline-2,10-diamine,
40. 3-{[2-amino-5-(1,3-benzodioxol-5-ylmethyl)-8-fluoro[1,2,4]triazolo[1,5-c]quinazolin-10-yl]amino}propan-1-ol,
41. 5-(1,3-benzodioxol-5-ylmethyl)-N~10~-[2-(dimethylamino)ethyl]-8-fluoro[1,2,4]triazolo[1,5-c]quinazoline-2,10-diamine,
42. 5-(1,3-benzodioxol-5-ylmethyl)-8-fluoro-N~10-(2-pyrrolidin-1-ylethyl)[1,2,4]triazolo[1,5-c]quinazoline-2,10-diamine,
43. 5-(1,3-benzodioxol-5-ylmethyl)-8-fluoro-N~10-(2-morpholin-4-ylethyl)[1,2,4]triazolo[1,5-c]quinazoline-2,10-diamine,
44. 5-(1,3-benzodioxol-5-ylmethyl)-8-fluoro-10-(4-methylpiperazin-1-yl)[1,2,4]triazolo[1,5-c]quinazolin-2-amine,
45. 5-(1,3-benzodioxol-5-ylmethyl)-10-chloro[1,2,4]triazolo[1,5-c]quinazolin-2-amine,
46. 5-(1,3-benzodioxol-5-ylmethyl)-N-10-cyclopropyl-8-fluoro[1,2,4]triazolo[1,5-c]quinazoline-2,10-diamine,
47. 5-(1,3-benzodioxol-5-ylmethyl)-10-fluoro-8-(4-methylpiperazin-1-yl)[1,2,4]triazolo[1,5-c]quinazolin-2-amine,
48. 2-amino-5-(1,3-benzodioxol-5-ylmethyl)[1,2,4]triazolo[1,5-c]quinazolin-8-ol,
49. 5-(1,3-benzodioxol-5-ylmethyl)-8-fluoro-N~10-(2-methoxyethyl)[1,2,4]triazolo[1,5-c]quinazoline-2,10-diamine,
50. 2-amino-5-(1,3-benzodioxol-5-ylmethyl)-N-(2-hydroxyethyl)[1,2,4]triazolo[1,5-c]quinazoline-8-carboxamide,
51. 2-amino-5-(1,3-benzodioxol-5-ylmethyl)[1,2,4]triazolo[1,5-c]quinazoline-8-carboxamide,
52. 2-amino-5-(1,3-benzodioxol-5-ylmethyl)-N-(3-hydroxypropyl)[1,2,4]triazolo[1,5-c]quinazoline-8-carboxamide,
53. 8-fluoro-5-[(5-methoxy-1H-indol-3-yl)methyl][1,2,4]triazolo[1,5-c]quinazolin-2-amine,
54. 2-({2-amino-5-[(5-methoxy-1H-indol-3-yl)methyl][1,2,4]triazolo[1,5-c]quinazolin-8-yl}amino)ethanol,
55. 8-fluoro-5-(3,4,5-trimethoxybenzyl)[1,2,4]triazolo[1,5-c]quinazolin-2-amine,
56. 2-{[2-amino-5-(3,4,5-trimethoxybenzyl)[1,2,4]triazolo[1,5-c]quinazolin-8-yl]amino}ethanol,
57. 3-{[2-amino-5-(3,4,5-trimethoxybenzyl)[1,2,4]triazolo[1,5-c]quinazolin-8-yl]amino}propan-1-ol,
58. 2-{[2-amino-5-(1,3-benzodioxol-5-ylmethyl)[1,2,4]triazolo[1,5-c]quinazolin-10-yl]amino}ethanol,
59. 2-[(2-amino-8-fluoro-5-propyl[1,2,4]triazolo[1,5-c]quinazolin-10-yl)amino]ethanol,
60. 5-(1,3-benzodioxol-5-ylmethyl)-10-fluoro-8-(4-methylpiperazin-1-yl)[1,2,4]triazolo[1,5-c]quinazolin-2-amine trifluoroacetate,
61. 5-[4-(benzyloxy)-3-methoxybenzyl]-8-fluoro[1,2,4]triazolo[1,5-c]quinazolin-2-amine,
62. 8-fluoro-5-[4-(trifluoromethoxy)benzyl][1,2,4]triazolo[1,5-c]quinazolin-2-amine,
63. 2-({2-amino-5-[4-(trifluoromethoxy)benzyl][1,2,4]triazolo[1,5-c]quinazolin-8-yl}amino)ethanol,
64. 3-({2-amino-5-[4-(trifluoromethoxy)benzyl][1,2,4]triazolo[1,5-c]quinazolin-8-yl}amino)propan-1-ol,
65. 3-({2-amino-5-[4-(benzyloxy)-3-methoxybenzyl][1,2,4]triazolo[1,5-c]quinazolin-8-yl}amino)propan-1-ol,
66. 2-({2-amino-5-[4-(benzyloxy)-3-methoxybenzyl][1,2,4]triazolo[1,5-c]quinazolin-8-yl}amino)ethanol,
67. 4-({2-amino-8-[(2-hydroxyethyl)amino][1,2,4]triazolo[1,5-c]quinazolin-5-yl}methyl)-2-methoxyphenol,
68. 4-[(2-amino-8-fluoro[1,2,4]triazolo[1,5-c]quinazolin-5-yl)methyl]-2-methoxyphenol,
69. 4-({2-amino-8-[(3-hydroxypropyl)amino][1,2,4]triazolo[1,5-c]quinazolin-5-yl}methyl)-2-methoxyphenol,
70. 5-(1,3-benzodioxol-5-ylmethyl)-8-fluoro-N~10~,N~10~-dimethyl[1,2,4]triazolo[1,5-c]quinazoline-2,10-diamine,
71. 5-(1,3-benzodioxol-5-ylmethyl)-8,10-dimethoxy[1,2,4]triazolo[1,5-c]quinazolin-2-amine,
72. 5-[2-(3,5-dimethoxyphenyl)ethyl][1,2,4]triazolo[1,5-c]quinazolin-2-amine,
73. 5-[2-(3,5-dimethoxyphenyl)ethyl]-8,10-difluoro[1,2,4]triazolo[1,5-c]quinazolin-2-amine,
74. 2-({2-amino-5-[2-(3,5-dimethoxyphenyl)ethyl]-8-fluoro[1,2,4]triazolo[1,5-c]quinazolin-10-yl}amino)ethanol,
75. 5-[2-(2-amino[1,2,4]triazolo[1,5-c]quinazolin-5-yl)ethyl]benzene-1,3-diol,
76. 5-(2-{2-amino-8-fluoro-10-[(2-hydroxyethyl)amino][1,2,4]triazolo[1,5-c]quinazolin-5-yl}ethyl)benzene-1,3-diol and
77. {(2S)-1-[2-amino-5-(1,3-benzodioxol-5-ylmethyl)[1,2,4]triazolo[1,5-c]quinazolin-8-yl]pyrrolidin-2-yl}methanol.

The present invention also provides a process for the preparation of a compound of formula (I) as defined above, characterized in that the process comprises the following steps:

1) reacting a compound of formula (II)

(II)

wherein Z and W are as defined above, with SOCl$_2$, or (COCl)$_2$, or 2-(1H-7-azabenzotriazol-1-yl)-1,1,3,3-tetramethyl uronium hexafluorophosphate methanaminium (HATU), or O-(benzotriazol-1-yl)-N,N,N',N'-tetramethyluronium tetrafluoroborate (TBTU) or N,N'-dicyclohexylcarbodiimide (DCC); or N,N'-dicyclohexylcarbodiimide and pentafluorophenol; or N,N'-dicyclohexylcarbodiimide and 1-hydroxypyrrolidine-2,5-dione (NHS), or N,N'-carbonyl diimidazole (CDI); in a solvent such as chloroform, DCE, dioxane, tetrahydrofuran, pyridine or DMF, at a temperature ranging from 0° C. to 120° C.;

2) condensing the resultant compound of formula (III)

(III)

wherein Z and W are as defined abone and Y is

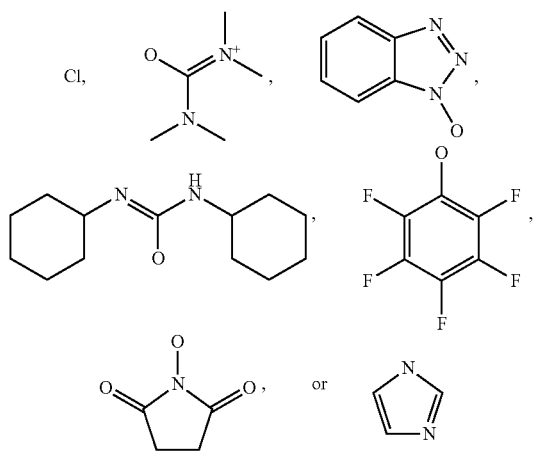

with a compound of formula (IV)

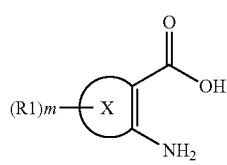

(IV)

wherein X, m and R1 are as defined above, in a solvent such as chloroform, DCE, dioxane, tetrahydrofuran, pyridine or DMF, in presence, if necessary, of an organic base such as TEA, DIPEA or 4-methyl-morpholine, at a temperature ranging from 0° C. to 90° C.;
3) reacting the resultant compound of formula (V)

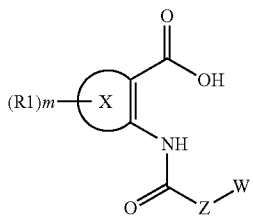

(V)

wherein X, m, R1, Z and W are as defined above, with $SOCl_2$, acetic or trifluoroacetic anhydride, as reagent and solvent, or DCC in pyridine in a range of temperature ranging from 100° C. to 150° C.;
4) condensing the resultant compound of formula (VI)

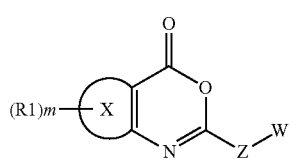

(VI)

wherein X, m, R1, Z and W are as defined above, with aminoguanidine hydrogencarbonate by melting at 170° C. or under microwaves heating at 180° C. for 30 minutes to 2 hours, to give a compound of formula (I) as defined above and optionally converting the resultant compound of formula (I) as defined above into a different compound of formula (I); and, if desired, converting a compound of formula (I) into a pharmaceutically acceptable salt thereof or converting a salt into the free compound of formula (I).

A preferred preparation of a compound of formula (I)A′

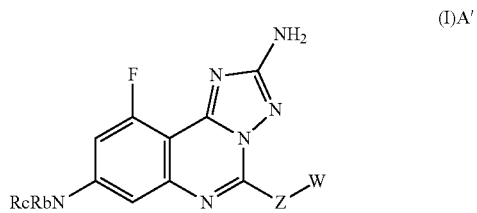

(I)A′ wherein Z, W, Rb and Rc are as defined above, is characterized in that the process comprises the following steps:
5) reacting a compound of formula (V)A

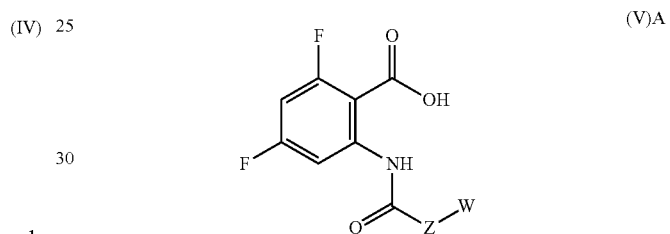

(V)A wherein Z and W are as defined above, with diazomethane or trimethylsilyldiazomethane diethyl ether in a solvent such as DCM, chloroform or THF at 0° C.;
6) reacting the resultant compound of formula (VII)A

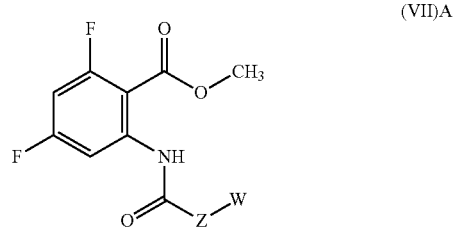

(VII)A wherein Z and W are as defined above, with a compound of formula NHRbRc wherein Rb and Rc are as defined above, in a solvent such as DMF, DMSO or N-methylpirrolidone at 50-120° C.;
7) reacting the resultant compound of formula (VIII)A

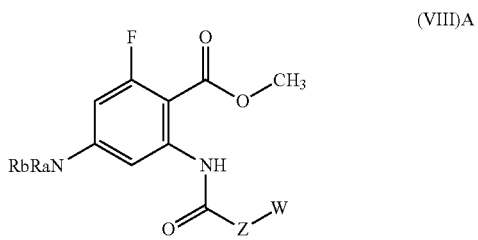

(VIII)A wherein Z, W, Rb and Rc are as defined above, with NaOH or LiOH in a solvent such as methanol, ethanol or THF at 50° C.;
8) reacting the resultant compound of formula (IX)A

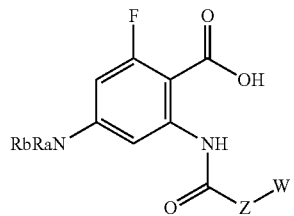

(IX)A wherein Z, W, Rb and Rc are as defined above, with acetic or trifluoroacetic anhydride at reflux;
9) reacting the resultant compound of formula (X)A

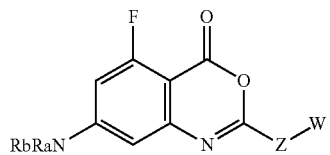

(X)A wherein Z, W, Rb and Rc are as defined above, with aminoguanidine hydrogenocarbonate under microwaves condition at 150-180° C., to give a compound of formula (I)A' as defined above, and optionally converting the resultant compound of formula (I)A' as defined above into a different compound of formula (I)A; and, if desired, converting a compound of formula (I)A' into a pharmaceutically acceptable salt thereof or converting a salt into the free compound of formula (I)A.

The synthesis of a compound of formula (I), according to the synthetic process described below, can be conducted in a stepwise manner, whereby each intermediate is isolated and purified by standard purification techniques, like, for example, column chromatography, before carrying out the subsequent reaction. Alternatively, two or more steps of the synthetic sequence can be carried out in a so-called "one-pot" procedure, as known in the art, whereby only the compound resulting from the two or more steps is isolated and purified.

If necessary or wanted, the process comprises converting a compound of formula (I) into a different compound of formula (I) by known chemical reactions such as:

a) hydrolysis under acid or basic condition of a compound of formula (I) wherein R1 is COORe, wherein Re is as defined above but hydrogen, into another compound of formula (I) wherein Re is hydrogen, according to standard procedures as reported in The Chemistry of Carboxylic Acids and Esters, Saul Patai, Interscience Publisher (John Wiley & Sons 1969).

b) reduction of a compound of formula (I) wherein R1 is COORe, wherein Re is as defined above but hydrogen, into another compound of formula (I) wherein R1 is $CH_2OH$, according to the standard procedure as reported in The Chemistry of Carboxylic Acids and Esters, Saul Patai, Interscience Publisher (John Wiley & Sons 1969), or in The Chemistry of Hydroxyl Group, Saul Patai, Interscience Publisher (John Wiley & Sons 1971).

c) amidation of a compound of formula (I) wherein R1 is COORe, wherein Re is as defined above, into the corresponding amide by reaction with a suitable amine according to the standard procedures as reported in The Chemistry of Amides, Saul Patai, Interscience Publisher (John Wiley & Sons 1970), or in Tetrahedron 61 (2005) 10827-10852.

d) reduction of an amide group into the corresponding amine according to the standard procedures as reported in The Chemistry of Amino Group, Saul Patai, Interscience Publisher (John Wiley & Sons 1968).

e) alkylation or reductive alkylation of primary or secondary amines into the corresponding secondary and tertiary amines according to the standard procedure as reported in The Chemistry of Amino Group, Saul Patai, Interscience Publisher (John Wiley & Sons 1968), or in J. Am. Chem. Soc., 1971, 93, 2897, or in Comprensive Organic Synthesis, Trost B. N., Fleming L. (Eds. Pergamon Press: New York, 1991; Vol. 8).

f) reduction of a aromatic nitro group $NO_2$ into the corresponding primary amine $NH_2$ according to the standard procedure as reported in The Chemistry of Nitro and Nitroso Group, Henry Feuer, Interscience Publisher (John Wiley & Sons 1969).

g) aromatic nucleophilic displacement of a fluorine atom by primary or secondary amines according to the standard procedures as reported in Journal of Organic Chemistry (1966), 31(7), 2319-21 or in Comprensive Organic Synthesis, Trost B. N., Fleming L. (Eds. Pergamon Press: New York, 1991).

h) protecting/deprotecting group methodologies and synthetic chemistry conversions according to the standard procedures as reported in W. Greene and P. G. M. Wuts, Protective Groups in Organic Synthesis, 2d. Ed., (John Wiley and Sons 1991), L. Fieser and M. Fieser, Fieser and Fieser's Reagents for Organic Synthesis (John Wiley & Sons 1994), R. Larock, Comprehensive Organic Transformations (VCH Publishers 1989), T. and L. Paquette, ed., Encyclopedia of Reagents for Organic Synthesis (John Wiley & Sons 1995).

i) reduction of a cyano group CN into the corresponding primary amine $CH_2NH_2$ according to the standard procedure as reported in The Chemistry of Cyano Group, Saul Patai, Interscience Publisher (John Wiley & Sons 1970) and in The Chemistry of Amino Group, Saul Patai, Interscience Publisher (John Wiley & Sons 1968).

The synthesis of a compound of formula (I), according to the synthetic process described above, can be conducted in a stepwise manner, whereby each intermediate is isolated and purified by standard purification techniques, like, for example, column chromatography, before carrying out the subsequent reaction. Alternatively, two or more steps of the synthetic sequence can be carried out in a so-called "one-pot" procedure, as known in the art, whereby only the compound resulting from the two or more steps is isolated and purified.

According to any variant of the process for preparing the compounds of formula (I), the starting materials and any other reactants are known or easily prepared according to known methods.

Pharmacology

The potencies of the compounds of the present invention were evaluated by measuring the Her2 degradation as a marker for Hsp90 inhibition.

Hsp90 is a key component of a chaperone machinery that catalyzes the folding and quality control of several proteins. Its inhibition impairs the capacity to fold or stabilize its client proteins, leading to the proteosomal dependent degradation of these unfolded proteins. At the moment, there is an increasing number (>100) of reported Hsp90 clients, but one of the most frequently way to detect Hsp90 chaperone inhibition is the detection of Her2 protein levels after short time treatment (usually 8-24 h), in order to be sure about the specificity of this effect.

Cellular activity of Hsp90 inhibitors was assessed by measuring the induced loss of Her2 protein levels in BT474 breast cancer cells (ATCC #HTB-20). Cellular Her2 levels were measured by immunocytochemistry, and quantified using an ArrayScan vTi instrument (Cellomics Thermo Scientific).

Her2 Degradation Assay

Cellular activity of Hsp90 inhibitors was assessed by measuring the induced loss of Her2 protein levels in BT474 breast cancer cells (ATCC #HTB-20). Cellular Her2 levels were measured by immunocytochemistry, and quantified using an ArrayScan vTi instrument (Cellomics Thermo Scientific).

Studies were performed as follows: 5000 cells/well are seeded in 96 well plates (Perkin Elmer) in DMEM/5% FCS and incubated for 48 hours at 37° C., 5% $CO_2$.

Medium is then replaced with fresh medium containing test compounds at the required concentration. Concentration curves are prepared in DMEM/10% FCS from compound stocks in DMSO, and final DMSO concentration is 0.1% (v/v). Duplicate wells for each concentration point are prepared, with a typical highest compound concentration of 30 μM. After addition of compound, plates are returned to the incubator for 8 hours, then fixed by replacing medium with PBS containing 3,7% paraformaldehyde solution. Plates are incubated for 20 minutes at room temperature, then wells are washed in PBS and cells permiabilised by incubating with PBS containing 0, 3% Triton X-100 for 15 minutes at room temperature. Non-specific binding sites are blocked by incubating wells for 1 hour in PBS containing 3% (w/v) BSA. Wells are then incubated for 1 hour at room temperature in PBS containing anti Her2 mouse monoclonal (Anti-c-ErbB2/c-Neu, Mouse mAb 3B5, Calbiochem Cat No OP15) diluted 1:100 in 1% (w/v) BSA. After 3 washes in PBS, wells are incubated in PBS (w/v) 1% BSA containing a 2 μg/ml of Cy2-conjugated Goat anti mouse secondary antibody (Amersham Pharmacia Biotech cat. No PA 42002) (Absorption maximum 489 nm fluorescence maximum 506 nm) and 1 μg/ml of DAPI (Absorption maximum 359 nm fluorescence maximum 461 nm) (4',6-diamidine-2-phenylindole, dilactate) (Sigma cat. No D 9564) a high sensitivity dye to detect nucleid acid for nuclear staining. After washing a further 3 times in PBS, cellular Her2 immunoreactivity is assessed using the ArrayScan vTi instrument, with a Zeiss 10×0.5 N.A. objective, and applying the Cytotoxity.V3 algorithm (Cellomics/Thermo Fisher) with a XF100 filter. At least 10 fields, corresponding to at least 900 cells, are read for each well. IC50 values represent the compound concentration at which cellular Her2 signal is diminished by 50% compared with untreated controls.

The following formula is used:

$$Y = \text{Bottom} + (\text{Top} - \text{Bottom})/(1 + 10^{((\log(IC50)-X)*p)})$$

X is the logarithm of concentration. Y is the response; Y starts at Bottom and goes to Top with a sigmoidal curve with a Hillslope p.

Given the above assay, the compounds of formula (I) result to possess a remarkable Hsp90 inhibitory activity, as proven by the induction of the Her2 protein degradation, as shown in the following Table 1.

TABLE 1

| Compound | Her2 Degradation $IC_{50}$ (μM) |
|---|---|
| 2-{[2-amino-5-(1,3-benzodioxol-5-ylmethyl)[1,2,4]triazolo[1,5-c]quinazolin-8-yl]amino}ethanol | 2.88 |
| 5-(1,3-benzodioxol-5-ylmethyl)-10-fluoro[1,2,4]triazolo[1,5-c]quinazolin-2-amine | 6.78 |
| 5-(1,3-benzodioxol-5-ylmethyl)[1,2,4]triazolo[1,5-c]quinazoline-2,8-diamine | 18.10 |

From all of the above, the novel compounds of formula (I) of the invention appear to be particularly advantageous in the therapy of diseases such as cancer neurodegenerative disorders.

The compounds of the present invention can be administered either as single agents or, alternatively, in combination with known anticancer treatments such as radiation therapy or chemotherapy regimen in combination with, for example, antihormonal agents such as antiestrogens, antiandrogens and aromatase inhibitors, topoisomerase I inhibitors, topoisomerase II inhibitors, agents that target microtubules, platin-based agents, alkylating agents, DNA damaging or intercalating agents, antineoplastic antimetabolites, other kinase inhibitors, other anti-angiogenic agents, inhibitors of kinesins, therapeutic monoclonal antibodies, inhibitors of mTOR, histone deacetylase inhibitors, farnesyl transferase inhibitors, and inhibitors of hypoxic response.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight, and conditions of the patient and administration route.

For example, a suitable dosage adopted for oral administration of a compound of formula (I) may range from about 100 to about 1 mg per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form.

For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions.

As an example the syrups may contain, as a carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

Experimental Section

For a reference to any specific compound of formula (I) of the invention, optionally in the form of a pharmaceutically acceptable salt, see the experimental section and claims. Referring to the examples that follow, compounds of the present invention were synthesized using the methods described herein, or other methods, which are well known in the art.

The following abbreviations were employed:

| | |
|---|---|
| mg | milligram |
| mL | milliliter |
| μL | microliter |
| M | molar |
| mM | millimolar |
| μM | micromolar |
| nM | nanomolar |
| DCC | dicyclohexylcarbodiimide |
| TBTU | O-(benzotriazol-1-yl)-N,N,N',N'-tetramethylisouronium tetrafluoroborate |
| TEA | triethylamine |
| DIPEA | N,N'-Diisopropylethylamine |
| Fmoc | 9H-fluoren-9-ylmethyl carbamate |
| TBDMS | tert-butyldimethylsilyl |
| DMSO | dimethylsulfoxide |
| DCE | dichloroethane |
| DMF | N,N-dimethylformamide |
| DCM | dichloromethane |

The following examples illustrate the syntheses of the compounds of the present invention:

EXAMPLE 1

5-(4-Nitrobenzyl)-[1,2,4]triazolo[1,5-c]quinazolin-2-amine

[(I); m=0, X=phenyl, Z=CH$_2$, W=4-nitrophenyl]

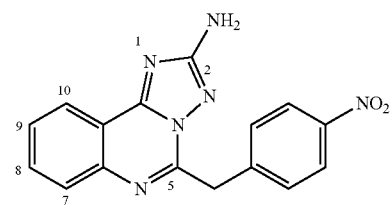 [SMILES: Nc1nc2c3ccccc3nc(Cc3ccc([N+](=O)[O-])cc3)n2n1]

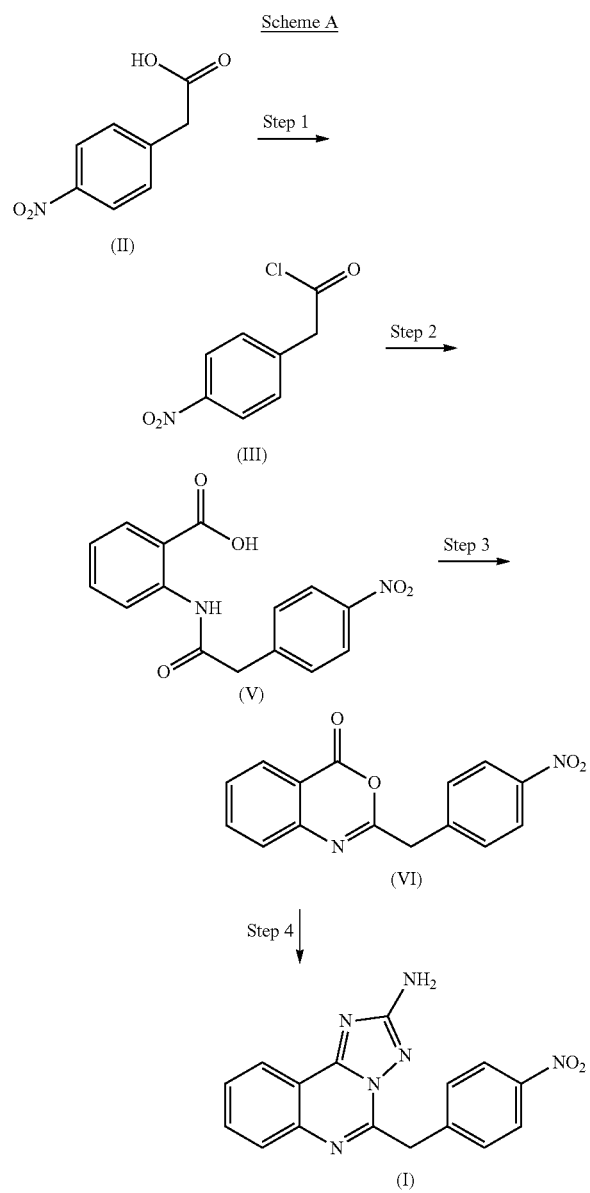

Scheme A

Step 1

4-nitro-phenyl)-acetyl chloride (III)

To a stirred solution of commercially available (4-nitro-phenyl)-acetic acid (3 g) in THF (50 mL) was added dropwise oxalyl chloride (5 mL) followed by the addition of two drops of DMF. When the bubbling subsided, the yellowish solution was furthermore stirred for two hours. The solvent was then carefully removed, to furnish the desired compound in quantitative yield.

1H-NMR (400 MHz), δ (ppm, CDCl$_3$-d): 3.78 (s, 2 H) 7.66 (d, 2 H) 8.24 (d, 2 H)

Step 2

2-{[(4-nitrophenyl)acetyl]amino}benzoic acid (V)

To a stirred solution of (4-nitro-phenyl)-acetyl chloride (2.20 g, 11.05 mmol) in anhydrous dichloromethane (50 mL) was added 2-aminobenzoic acid (0.76 g, 5.50 mmol) followed by the addition of pyridine (3 mL). After stirring for 5 hours at rt, the cloudy solution was diluted with dichloromethane and thoroughly washed with 3 M HCl solution, then with brine and dried over Na$_2$SO$_4$. The solvent was removed and the solid crystallized from ethyl acetate to provide the title compound (2.9 g, 88% yield).

1H-NMR (400 MHz), δ (ppm, DMSO-d$_6$): 3.77 (s, 2 H) 7.19-7.23 (m, 2 H) 7.51 (dd, 2 H) 7.95 (m, 1 H) 8.22 (dd, 2 H) 8.55 (m, 1 H) 9.52 (s, 1 H).

Step 3

2-(4-nitrobenzyl)-4H-3,1-benzoxazin-4-one (VI)

A stirred solution of 2-{[(4-nitrophenyl)acetyl] amino}benzoic acid (7.5 g, 25 mmol) in acetic anhydride (50 mL) was refluxed for 3 hours. The solvent was removed in vacuum and the residue was taken up in diethyl ether, to provide after filtration and drying the title compound (5.7 g, 81% yield).

1H-NMR (400 MHz), δ (ppm, DMSO-d$_6$): 4.26 (s, 2 H) 7.42 (m, 1 H) 7.55 (dd, 1 H) 7.62 (m, 1 H) 7.73 (m, 1 H) 8.15 (m, 1 H) 8.23 (dd, 2 H)

Step 4 (I)

5-(4-nitrobenzyl)-[1,2,4]triazolo[1,5-c]quinazolin-2-amine

A solution of 2-(4-nitrobenzyl)-4H-3,1-benzoxazin-4-one (5.7 g, 20.2 mmol) and aminoguanidine hydrogencarbonate (2.7 g, 20.2 mmol) in pyridine (25 mL) was heated under microwave condition at 180° C. for 30 minutes. After cooling, the red solution was taken up in ethyl acetate, washed with brine and dried over Na$_2$SO$_4$. The solvent was removed in vacuum and the residue was chromatographed on silica gel eluting with DCM/CH$_3$OH 95/5 to furnish the title compound (2.7 g, 42% yield)

1H-NMR (400 MHz), δ (ppm, DMSO-d$_6$): 8.25-8.19 (m, 3H), 7.68 (d, 1H), 7.82 (m, 1H), 7.62-7.65 (m, 3H), 6.50 (bs, 2H), 4.70 (bs, 2H)

EXAMPLE 2

5-(3-nitro-benzyl)-[1,2,4]triazolo[1,5-c]quinazolin-2-ylamine

[(I); m=0, X=phenyl, Z=CH$_2$, W=3-nitrophenyl]

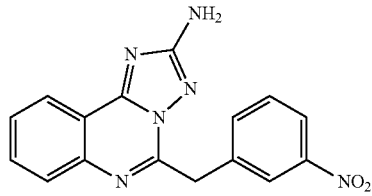 [SMILES: Nc1nc2c3ccccc3nc(Cc3cccc([N+](=O)[O-])c3)n2n1]

Steps 2, 3 and 4

To a solution of commercially available (3-nitro-phenyl)-acetyl chloride (2.20 g, 11.05 mmol) in anhydrous DCM (9 mL) was added 2-aminobenzoic acid (0.76 g, 5.50 mmol). Pyridine (3 mL) was then added to the mixture and the reaction mixture was heated under microwave condition at 120° C. for 30 minutes, then diluted with dichloromethane and washed with NaHCO$_3$ satured solution, then with water followed by brine. The organic phase was dried over Na$_2$SO$_4$, filtered and evaporated to give the 2-(3-nitro-benzyl)-benzo[d][1,3]oxazin-4-one intermediate as red oil. To a solution of 2-(3-nitro-benzyl)-benzo[d][1,3]oxazin-4-one in dry pyridine (10 mL) was added aminoguanidine hydrogencarbonate (0.90 g, 6.60 mmol) and the mixture was heated under microwave condition at 180° C. for 20 minutes. The solvent was then evaporated and the crude was purified by flash column chromatography on silica gel eluting with DCM/CH$_3$OH 95/5 to afford the title compound as orange solid (0.35 g, 30% yield).

1H-NMR (400 MHz), δ (ppm, DMSO-d$_6$): 8.31 (t, 1 H), 8.24 (d, 1 H), 8.16 (d, 1 H), 7.87-7.83 (m, 2 H), 7.80 (m, 1 H), 7.70-7.62 (m, 2 H), 6.50 (bs, 2 H), 4.70 (bs, 2 H).

EXAMPLE 3

5-(4-methoxy-benzyl)-[1,2,4]triazolo[1,5-c]quinazolin-2-ylamine

[(I); m=0, X=phenyl, Z=CH$_2$, W=4-methoxyphenyl]

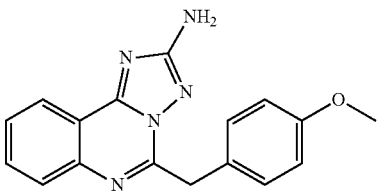 [SMILES: COc1ccc(Cc2nc3ccccc3c3nc(N)nn23)cc1]

Operating as in Example 2, but employing (4-methoxyphenyl)-acetyl chloride instead of (3-nitro-phenyl)-acetyl chloride, the title compound was obtained in 35% yield.

1H-NMR (400 MHz), δ (ppm, DMSO-d$_6$): 8.22 (d, 1 H), 7.90 (d, 1 H), 7.81 (m, 1 H), 7.67 (m, 1 H), 7.34 (d, 2 H), 6.89 (d, 2 H), 6.46 (bs, 2 H), 4.45 (bs, 2 H), 3.72 (s, 3 H).

EXAMPLE 4

5-(3,5-dimethoxy-benzyl)-[1,2,4]triazolo[1,5-c]quinazolin-2-ylamine

[(I); m=0, X=phenyl, Z=CH$_2$, W=3,5-dimethoxyphenyl]

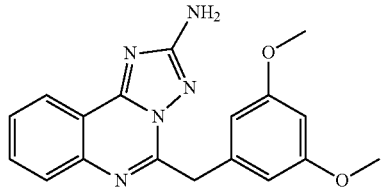 [SMILES: COc1cc(Cc2nc3ccccc3c3nc(N)nn23)cc(OC)c1]

Operating as in Example 2, but employing (3,5-dimethoxy-phenyl)-acetyl chloride instead of (3-nitro-phenyl)-acetyl chloride, the title compound was obtained in 27% yield.

1H-NMR (400 MHz), δ (ppm, DMSO-d$_6$): 8.22 (d, 1 H), 7.91 (d, 1 H), 7.81 (m, 1 H), 7.68 (m, 1 H), 6.55 (d, 2 H), 6.47 (bs, 2 H), 6.38 (t, 1 H), 4.44 (bs, 2 H), 3.69 (s, 6 H).

EXAMPLE 5

5-(2,4-dimethoxy-benzyl)-[1,2,4]triazolo[1,5-c]quinazolin-2-ylamine

[(I); m=0, X=phenyl, Z=CH$_2$, W=2,4-dimethoxyphenyl]

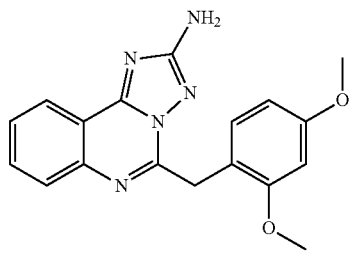 [SMILES: COc1ccc(Cc2nc3ccccc3c3nc(N)nn23)c(OC)c1]

Operating as in Example 2, but employing (2,4-dimethoxy-phenyl)-acetyl chloride instead of (3-nitro-phenyl)-acetyl chloride, the title compound was obtained in 29% yield.

1H-NMR (400 MHz), δ (ppm, DMSO-d$_6$): 8.23 (d, 1 H), 7.81-7.75 (m, 2 H), 7.66 (m, 1 H), 6.99 (d, 1 H), 6.59 (d, 1 H), 6.46-6.43 (m, 3 H), 4.39 (bs, 2 H), 3.75 (s, 3 H), 3.72 (s, 3 H).

EXAMPLE 6

5-(2,5-dimethoxy-benzyl)-[1,2,4]triazolo[1,5-c]quinazolin-2-ylamine

[(I); m=0, X=phenyl, Z=CH$_2$, W=2,5-dimethoxyphenyl]

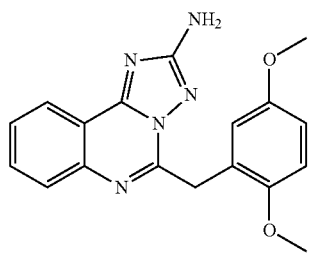 [SMILES: COc1ccc(OC)c(Cc2nc3ccccc3c3nc(N)nn23)c1]

Operating as in Example 2, but employing (2,5-dimethoxy-phenyl)-acetyl chloride instead of (3-nitro-phenyl)-acetyl chloride, the title compound was obtained in 31% yield.

1H-NMR (400 MHz), δ (ppm, DMSO-d$_6$): 8.23 (d, 1), 7.82-7.75 (m, 2), 7.66 (m, 1 H), 6.96 (d, 1 H), 6.83 (dd, 1 H), 6.74 (d, 1 H), 6.45 (bs, 2 H), 4.45 (bs, 2 H), 3.67 (s, 3), 3.65 (s, 3 H).

EXAMPLE 7

5-(3,4-dimethoxy-benzyl)-[1,2,4]triazolo[1,5-c]quinazolin-2-ylamine

[(I); m=0, X=phenyl, Z=CH$_2$, W=3,4-dimethoxyphenyl]

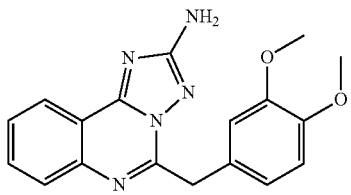 [SMILES: COc1ccc(Cc2nc3ccccc3c3nc(N)nn23)cc1OC]

Operating as in Example 2, but employing (3,4-dimethoxy-phenyl)-acetyl chloride instead of (3-nitro-phenyl)-acetyl chloride, the title compound was obtained in 37% yield.

1H-NMR (400 MHz), δ (ppm, DMSO-d$_6$): 8.22 (d, 1 H), 7.90 (d, 1 H), 7.80 (m, 1 H), 7.67 (m, 1 H), 7.09 (s, 1 H), 6.87-6.85 (m, 2 H), 6.46 (bs, 2 H), 4.44 (bs, 2 H), 3.72 (s, 3 H), 3.70 (s, 3 H).

EXAMPLE 8

5-(2,4-dimethoxy-benzyl)-8-nitro-[1,2,4]triazolo[1,5-c]quinazolin-2-ylamine

[(I); R1=8-NO$_2$, X=phenyl, Z=CH$_2$, W=2,4-dimethoxyphenyl]

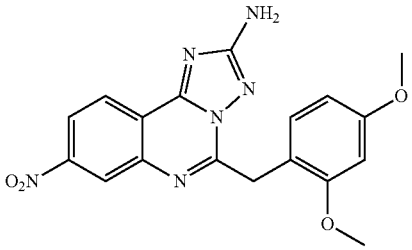 [SMILES: COc1ccc(Cc2nc3cc([N+](=O)[O-])ccc3c3nc(N)nn23)c(OC)c1]

Operating as in Example 2, but employing (2,4-dimethoxy-phenyl)-acetyl chloride instead of (3-nitro-phenyl)-acetyl chloride and 2-amino-4-nitro-benzoic acid instead of 2-aminobenzoic acid, the title compound was obtained in 14% yield.

1H-NMR (400 MHz), δ (ppm, DMSO-d$_6$): 8.50 (d, 1), 8.45 (d, 1), 8.40 (dd, 1), 7.07 (d, 1 H), 6.68 (bs, 2 H), 6.60 (d, 1 H), 6.48 (dd, 1 H), 4.44 (bs, 2 H), 3.76 (s, 3 H), 3.72 (s, 3 H).

EXAMPLE 9

5-(2,5-dimethoxy-benzyl)-[1,2,4]triazolo[1,5-c]quinazoline-8-nitro-2-ylamine

[(I); R1=8-NO$_2$, X=phenyl, Z=CH$_2$, W=2,5-dimethoxyphenyl]

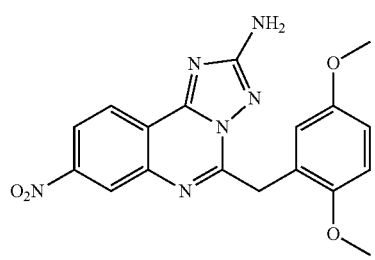 [SMILES: COc1ccc(OC)c(Cc2nc3cc([N+](=O)[O-])ccc3c3nc(N)nn23)c1]

Operating as in Example 2, but employing (2,5-dimethoxy-phenyl)-acetyl chloride instead of (3-nitro-phenyl)-acetyl chloride and 2-amino-4-nitro-benzoic acid instead of 2-aminobenzoic acid, the title compound was obtained in 23% yield.

1H-NMR (400 MHz), δ (ppm, DMSO-$d_6$): 8.55 (d, 1), 8.47 (d, 1), 8.38 (dd, 1), 7.17 (d, 1 H), 6.73 (bs, 2 H), 6.65 (d, 1 H), 6.52 (dd, 1 H), 4.47 (bs, 2 H), 3.75 (s, 3 H), 3.69 (s, 3 H).

EXAMPLE 10

5-(3,5-dimethoxy-benzyl)-9-iodo-[1,2,4]triazolo[1,5-c]quinazolin-2-ylamine

[(I); R1=9-I, X=phenyl, Z=CH$_2$, W=2,4-dimethoxyphenyl]

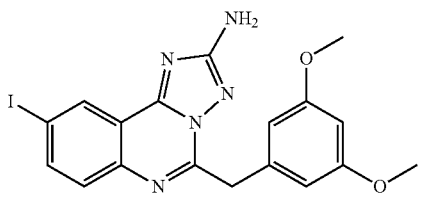 [SMILES: COc1cc(Cc2nc3ccc(I)cc3c3nc(N)nn23)cc(OC)c1]

Operating as in Example 2, but employing (3,5-dimethoxy-phenyl)-acetyl chloride instead of (3-nitro-phenyl)-acetyl chloride and 2-amino-5-iodio-benzoic acid instead of 2-aminobenzoic acid, the title compound was obtained in 27% yield.

1H-NMR (400 MHz), δ (ppm, DMSO-$d_6$): 8.49 (d, 1 H), 8.08 (dd, 1 H), 7.68 (d, 1 H), 6.55-6.53 (m, 3 H), 6.38 (t, 1 H), 4.42 (bs, 2 H), 3.69 (s, 6 H).

EXAMPLE 11

5-(3-bromo-4-methoxy-benzyl)-[1,2,4]triazolo[1,5-c]quinazolin-2-ylamine

[(I); m=0, X=phenyl, Z=CH$_2$, W=3-bromo-4-methoxyphenyl]

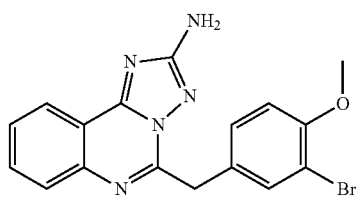 [SMILES: COc1ccc(Cc2nc3ccccc3c3nc(N)nn23)cc1Br]

Operating as in Example 2, but employing (3-bromo-4-methoxy-phenyl)-acetyl chloride instead of (3-nitro-phenyl)-acetyl chloride, the title compound was obtained in 15% yield.

1H-NMR (400 MHz), δ (ppm, DMSO-$d_6$): 8.22 (d, 1 H), 7.88 (d, 1 H), 7.80 (m, 1 H), 7.63 (d, 1 H), 7.37 (dd, 1 H), 7.07 (d, 1 H), 6.48 (bs, 2 H), 4.46 (bs, 2 H), 3.81 (s, 3 H).

EXAMPLE 12

5-benzo[1,3]dioxol-5-ylmethyl-[1,2,4]triazolo[1,5-c]quinazolin-2-ylamine

[(I); m=0, X=phenyl, Z=CH$_2$, W=benzo[1,3]dioxol-5-yl]

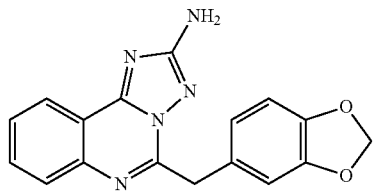 [SMILES: Nc1nc2c3ccccc3nc(Cc3ccc4c(c3)OCO4)n2n1]

Operating as in Example 2, but employing benzo[1,3]dioxol-5-yl-acetyl chloride instead of (3-nitro-phenyl)-acetyl chloride, the title compound was obtained in 23% yield.

1H-NMR (400 MHz), δ (ppm, DMSO-$d_6$): 8.22 (d, 1), 7.90 (d, 1), 7.80 (m, 1), 7.67 (m, 1), 7.00 (s, 1), 6.87-6.82 (m, 2), 6.47 (bs, 2), 5.96 (s, 2), 4.42 (bs, 2)

EXAMPLE 13

5-benzo[1,3]dioxol-5-ylmethyl-8-nitro-[1,2,4]triazolo[1,5-c]quinazolin-2-ylamine

[(I); R1=8-NO$_2$, X=phenyl, Z=CH$_2$, W=benzo[1,3]dioxol-5-yl]

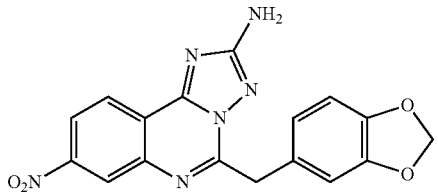 [SMILES: Nc1nc2c3ccc([N+](=O)[O-])cc3nc(Cc3ccc4c(c3)OCO4)n2n1]

Operating as in Example 2, but employing benzo[1,3]dioxol-5-yl-acetyl chloride instead of (3-nitro-phenyl)-acetyl chloride and instead of (3-nitro-phenyl)-acetyl chloride and 2-amino-4-nitro-benzoic acid instead of 2-aminobenzoic acid, the title compound was obtained in 23% yield.

1H-NMR (400 MHz), δ (ppm, DMSO-$d_6$): 8.60 (d, 1), 8.44-8.38 (m, 2), 7.01 (d, 1), 6.89-6.83 (m, 2), 6.70 (bs, 2), 5.98 (s, 2), 4.48 (bs, 2 H).

EXAMPLE 14

5-(2,3-dihydro-benzo[1,4]dioxin-6-ylmethyl)-[1,2,4]triazolo[1,5-c]quinazolin-2-ylamine

[(I); m=0, X=phenyl, Z=CH$_2$, W=benzo[1,4]dioxin-5-yl]

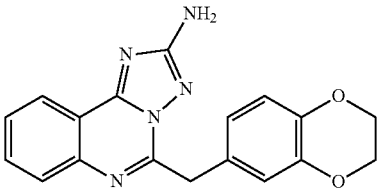 [SMILES: Nc1nc2c3ccccc3nc(Cc3ccc4c(c3)OCCO4)n2n1]

Operating as in Example 2, but employing (2,3-dihydro-benzo[1,4]dioxin-6-yl)-acetyl chloride instead of (3-nitro-phenyl)-acetyl chloride, the title compound was obtained in 28% yield.

1H-NMR (400 MHz), δ (ppm, DMSO-$d_6$): 8.21 (d, 1 H), 7.90 (d, 1 H), 7.81 (m, 1 H), 7.67 (m, 1 H), 6.90 (d, 1 H), 6.85 (dd, 1 H), 6.78 (d, 1 H), 6.47 (bs, 2 H), 4.38 (bs, 2 H), 4.18 (s, 4 H).

EXAMPLE 15

(R)-(2-amino-[1,2,4]triazolo[1,5-c]quinazolin-5-yl)-phenyl-methanol

[(I); m=0, X=phenyl, Z=CHOH, W=phenyl]

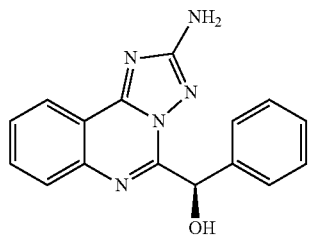 [SMILES: Nc1nc2c3ccccc3nc([C@H](O)c3ccccc3)n2n1]

Operating as in Example 2, but employing (R)-2-chloro-2-oxo-1-phenylethyl acetate instead of (3-nitro-phenyl)-acetyl chloride, the title compound was obtained in 17% yield.

1H-NMR (400 MHz), δ (ppm, DMSO-$d_6$): 8.22 (d, 1 H), 7.96 (d, 1 H), 7.84 (m, 1 H), 7.70 (m, 1 H), 7.54-7.52 (m, 2 H), 7.34-7.30 (m, 2 H), 7.26 (m, 1 H), 6.49 (bs, 2 H), 6.39 (d, 1 H), 6.27 (d, 1 H).

EXAMPLE 16

(S)-(2-amino-[1,2,4]triazolo[1,5-c]quinazolin-5-yl)-phenyl-methanol

[(I); m=0, X=phenyl, Z=CHOH, W=phenyl]

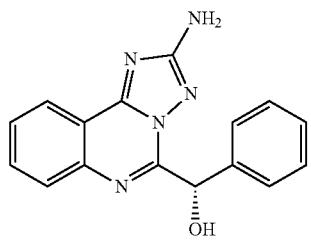 [SMILES: Nc1nc2c3ccccc3nc([C@@H](O)c3ccccc3)n2n1]

Operating as in Example 14, but employing (S)-2-chloro-2-oxo-1-phenylethyl acetate instead of (R)-2-chloro-2-oxo-1-phenylethyl acetate, the title compound was obtained in 12% yield.

1H-NMR (400 MHz), δ (ppm, DMSO-$d_6$): 8.22 (d, 1 H), 7.96 (d, 1 H), 7.84 (m, 1 H), 7.70 (m, 1 H), 7.54-7.52 (m, 2 H), 7.34-7.30 (m, 2 H), 7.26 (m, 1 H), 6.49 (bs, 2 H), 6.39 (d, 1 H), 6.27 (d, 1 H).

EXAMPLE 17

5-(2-benzyloxy-benzyl)-[1,2,4]triazolo[1,5-c]quinazolin-2-ylamine

[(I); m=0, X=phenyl, Z=CHOH, W=2-benzyloxy-phenyl]

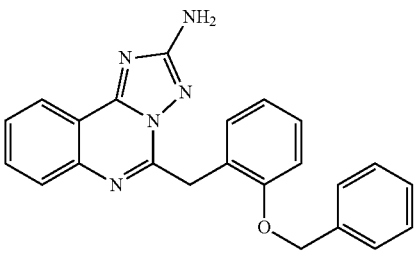 [SMILES: Nc1nc2c3ccccc3nc(Cc3ccccc3OCc3ccccc3)n2n1]

Operating as in Example 2, but employing (2-benzyloxy-phenyl)-acetyl chloride instead of (3-nitro-phenyl)-acetyl chloride, the title compound was obtained in 21% yield.

1H-NMR (400 MHz), δ (ppm, DMSO-$d_6$): 8.20 (d, 1 H), 7.78-7.76 (m, 2 H), 7.65 (m, 1 H), 7.27-7.22 (m, 2 H), 7.20-7.14 (m, 4 H), 7.05 (d, 1 H), 6.92 (m, 1 H), 6.43 (bs, 2 H), 5.06 (s, 2 H), 4.55 (bs, 2 H).

EXAMPLE 18

5-(2,3-dihydro-benzofuran-5-ylmethyl)-[1,2,4]triazolo[1,5-c]quinazolin-2-ylamine

[(I); m=0, X=phenyl, Z=$CH_2$, W=2,3-dihydro-benzofuran-5-yl]

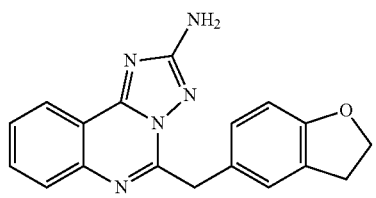 [SMILES: Nc1nc2c3ccccc3nc(Cc3ccc4c(c3)CCO4)n2n1]

Operating as in Example 2, but employing (2,3-dihydro-benzofuran-5-yl)-acetyl chloride instead of (3-nitro-phenyl)-acetyl chloride, the title compound was obtained in 18% yield.

1H-NMR (400 MHz), δ (ppm, DMSO-$d_6$): 8.20 (d, 1 H), 7.89 (d, 1 H), 7.81 (m, 1 H), 7.67 (m, 1 H), 7.25 (s, 1 H), 7.12 (d, 1 H), 6.68 (d, 1 H), 6.47 (bs, 2 H), 4.47 (t, 2 H), 4.43 (bs, 2 H), 3.12 (t, 2 H).

EXAMPLE 19

5-benzo[1,3]dioxol-5-ylmethyl-8-methanesulfonyl-[1,2,4]triazolo[1,5-c]quinazolin-2-ylamine

[(I); R1=8-$CH_3SO_2$, X=phenyl, Z=$CH_2$, W=benzo[1,3]dioxol-5-yl]

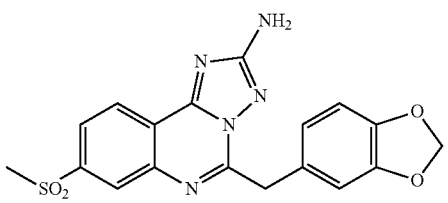 [SMILES: CS(=O)(=O)c1ccc2c(c1)nc(Cc1ccc3c(c1)OCO3)n1nc(N)nc21]

Operating as in Example 2, but employing benzo[1,3]dioxol-5-yl-acetyl chloride instead of (3-nitro-phenyl)-acetyl chloride and 2-amino-4-methylsulphonyl-benzoic acid instead of 2-aminobenzoic acid, the title compound was obtained in 13% yield.

1H-NMR (400 MHz), δ (ppm, DMSO-$d_6$): 8.45 (d, 1 H), 8.35 (d, 1H), 8.10 (dd, 1 H), 7.01 (d, 1H), 6.88-6.83 (m, 2 H), 6.65 (bs, 2 H), 5.98 (s, 2 H), 4.46 (bs, 2 H), 3.35 (s, 3 H).

EXAMPLE 20

2-amino-5-benzo[1,3]dioxol-5-ylmethyl-[1,2,4]triazolo[1,5-c]quinazoline-8-carboxylic acid

[(I); R1=8-COOH, X=phenyl, Z=CH$_2$, W=benzo[1,3]dioxol-5-yl]

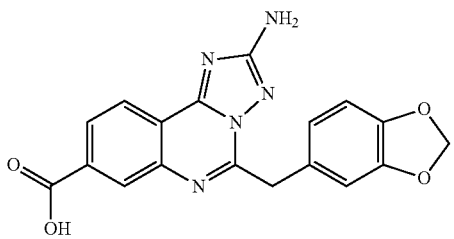 [SMILES: Nc1nc2c3ccc(C(=O)O)cc3nc(Cc3ccc4c(c3)OCO4)n2n1]

Operating as in Example 2, but employing benzo[1,3]dioxol-5-yl-acetyl chloride instead of (3-nitro-phenyl)-acetyl chloride and 2-amino-4-methoxycarbonyl-benzoic acid instead of 2-aminobenzoic acid, the title compound was obtained in 9% yield.

1H-NMR (400 MHz), δ (ppm, DMSO-$d_6$): 13.20 (bs, 1 H), 8.37 (d, 1 H), 8.28 (d, 1 H), 8.05 (dd, 1 H), 7.00 (d, 2H), 6.65 (bs, 2 H), 5.97 (s, 2 H), 4.47 (bs, 2 H).

EXAMPLE 21

5-benzo[1,3]dioxol-5-ylmethyl-8-fluoro-[1,2,4]triazolo[1,5-c]quinazolin-2-ylamine

[(I); R1=8-F, X=phenyl, Z=CH$_2$, W=benzo[1,3]dioxol-5-yl]

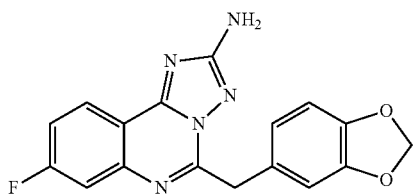 [SMILES: Nc1nc2c3ccc(F)cc3nc(Cc3ccc4c(c3)OCO4)n2n1]

Operating as in Example 2, but employing benzo[1,3]dioxol-5-yl-acetyl chloride instead of (3-nitro-phenyl)-acetyl chloride and 2-amino-4-fluoro-benzoic acid instead of 2-aminobenzoic acid, the title compound was obtained in 9% yield.

1H-NMR (400 MHz), δ (ppm, DMSO-$d_6$): 8.26 (dd, 1 H), 7.67 (dd, 1 H), 7.56 (m, 1 H), 6.99 (s, 1 H), 6.86-6.82 (m, 2 H), 6.51 (bs, 2 H), 5.97 (s, 2 H), 4.42 (bs, 2 H).

EXAMPLE 22

5-benzo[1,3]dioxol-5-ylmethyl-10-fluoro-[1,2,4]triazolo[1,5-c]quinazolin-2-ylamine

[(I); R1=10-F, X=phenyl, Z=CH$_2$, W=benzo[1,3]dioxol-5-yl]

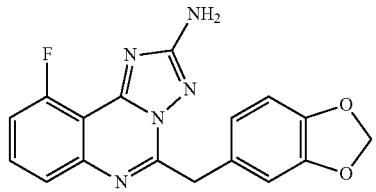 [SMILES: Nc1nc2c3c(F)cccc3nc(Cc3ccc4c(c3)OCO4)n2n1]

Operating as in Example 2, but employing benzo[1,3]dioxol-5-yl-acetyl chloride instead of (3-nitro-phenyl)-acetyl chloride and 2-amino-6-fluoro-benzoic acid instead of 2-aminobenzoic acid, the title compound was obtained in 14% yield.

1H-NMR (400 MHz), δ (ppm, DMSO-$d_6$): 7.78 (m, 1 H), 7.71 (d, 1 H), 7.49 (m, 1 H), 7.00 (s, 1 H), 6.87-6.83 (m, 2 H), 6.59 (bs, 2 H), 5.98 (s, 2 H), 4.44 (bs, 2 H).

EXAMPLE 23

N-(2-amino-5-benzo[1,3]dioxol-5-ylmethyl-[1,2,4]triazolo[1,5-c]quinazolin-9-yl)-acetamide

[(I); R1=9—NHCOCH$_3$, X=phenyl, Z=CH$_2$, W=benzo[1,3]dioxol-5-yl]

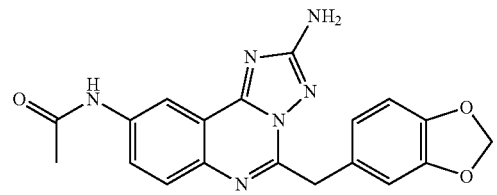 [SMILES: CC(=O)Nc1ccc2nc(Cc3ccc4c(c3)OCO4)n3nc(N)nc3c2c1]

Operating as in Example 2, but employing benzo[1,3]dioxol-5-yl-acetyl chloride instead of (3-nitro-phenyl)-acetyl chloride and 2-amino-5-acetamido-benzoic acid instead of 2-aminobenzoic acid, the title compound was obtained in 10% yield.

1H-NMR (400 MHz), δ (ppm, DMSO-$d_6$): 10.36 (bs, 1), 8.72 (d, 1 H), 7.84-7.77 (m, 2 H), 6.99 (s, 1 H), 6.85-6.82 (m, 2 H), 6.44 (bs, 2 H), 5.97 (s, 2 H), 4.40 (bs, 2 H), 2.13 (s, 3 H).

EXAMPLE 24

5-benzo[1,3]dioxol-5-ylmethyl-8-bromo-[1,2,4]triazolo[1,5-c]quinazolin-2-ylamine (I); R1=8-Br, X=phenyl, Z=CH$_2$, W=benzo[1,3]dioxol-5-yl]

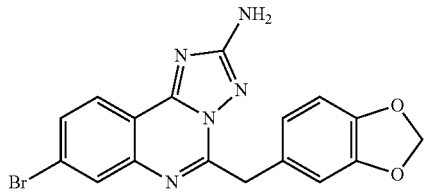 [SMILES: Nc1nc2c3ccc(Br)cc3nc(Cc3ccc4c(c3)OCO4)n2n1]

Operating as in Example 2, but employing benzo[1,3]dioxol-5-yl-acetyl chloride instead of (3-nitro-phenyl)-acetyl chloride and 2-amino-4-bromo-benzoic acid instead of 2-aminobenzoic acid, the title compound was obtained in 12% yield.

1H-NMR (400 MHz), δ (ppm, DMSO-d$_6$): 8.13 (d, 1 H), 8.10 (d, 1 H), 7.82 (dd, 1 H), 6.99 (s, 1 H), 6.85-6.83 (m, 2 H), 6.56 (bs, 2), 5.98 (s, 2 H), 4.43 (bs, 2 H).

EXAMPLE 25

2-amino-5-benzo[1,3]dioxol-5-ylmethyl-[1,2,4]triazolo[1,5-c]quinazoline-9-carbonitrileylamine

[(I); R1=9-CN, X=phenyl, Z=CH$_2$, W=aenzo[1,3]dioxol-5-yl]

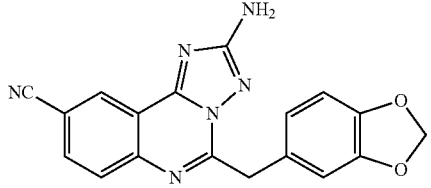 [SMILES: N#Cc1ccc2nc(Cc3ccc4c(c3)OCO4)n3nc(N)nc3c2c1]

Operating as in Example 2, but employing benzo[1,3]dioxol-5-yl-acetyl chloride instead of (3-nitro-phenyl)-acetyl chloride and 2-amino-5-cyano-benzoic acid instead of 2-aminobenzoic acid, the title compound was obtained in 21% yield.

1H-NMR (400 MHz), δ (ppm, DMSO-d$_6$): 8.64 (d, 1 H), 8.11 (dd, 1 H), 8.00 (d 1 H), 7.00 (s, 1 H), 6.87-6.82 (m, 2 H), 6.67 (bs, 2 H), 5.97 (s, 2 H), 4.46 (bs, 2 H).

EXAMPLE 26

2-amino-5-benzo[1,3]dioxol-5-ylmethyl-[1,2,4]triazolo[1,5-c]quinazolin-9-ol

[(I); R1=9-OH, X=phenyl, Z=CH$_2$, W=benzo[1,3]dioxol-5-yl]

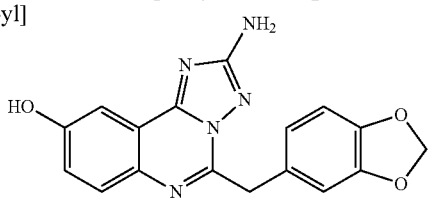

Operating as in Example 2, but employing benzo[1,3]dioxol-5-yl-acetyl chloride instead of (3-nitro-phenyl)-acetyl chloride and 2-amino-5-hydroxy-benzoic acid instead of 2-aminobenzoic acid, the title compound was obtained in 11% yield.

1H-NMR (400 MHz), δ (ppm, DMSO-d$_6$): 10.27 (bs, 1 H), 7.73 (d, 1 H), 7.43 (d, 1 H), 7.26 (dd, 1 H), 6.98 (s, 1 H), 6.83-6.80 (m, 2 H), 6.37 (bs, 2 H), 5.97 (s, 2 H), 4.37 (bs, 2 H).

EXAMPLE 27

2-amino-5-benzo[1,3]dioxol-5-ylmethyl-[1,2,4]triazolo[1,5-c]quinazolin-7-ol

[(I); R1=7-OH, X=phenyl, Z=CH$_2$, W=benzo[1,3]dioxol-5-yl]

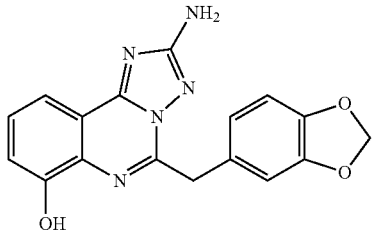 [SMILES: Nc1nc2c3cccc(O)c3nc(Cc3ccc4c(c3)OCO4)n2n1]

Operating as in Example 2, but employing benzo[1,3]dioxol-5-yl-acetyl chloride instead of (3-nitro-phenyl)-acetyl chloride and 2-amino-3-hydroxy-benzoic acid instead of 2-aminobenzoic acid, the title compound was obtained in 17% yield.

1H-NMR (400 MHz), δ (ppm, DMSO-d$_6$): 9.87 (bs, 1 H), 7.60 (dd, 1 H), 7.47 (t, 1 H), 7.18 (dd, 1 H), 7.07 (d, 1 H), 6.88-6.81 (m, 2 H), 6.43 (bs, 2H), 5.95 (s, 2 H), 4.41 (bs, 2 H).

EXAMPLE 28

5-benzo[1,3]dioxol-5-ylmethyl-10-methoxy-[1,2,4]triazolo[1,5-c]quinazolin-2-ylamine

[(I); R1=10-OCH$_3$, X=phenyl, Z=CH$_2$, W=benzo[1,3]dioxol-5-yl]

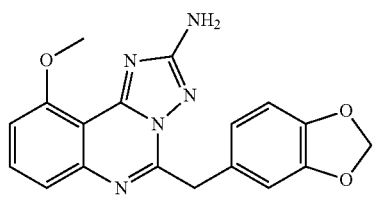 [SMILES: COc1cccc2nc(Cc3ccc4c(c3)OCO4)n3nc(N)nc3c12]

Operating as in Example 2, but employing benzo[1,3]dioxol-5-yl-acetyl chloride instead of (3-nitro-phenyl)-acetyl chloride and 2-amino-6-methoxy-benzoic acid instead of 2-aminobenzoic acid, the title compound was obtained in 15% yield.

1H-NMR (400 MHz), δ (ppm, DMSO-d$_6$): 7.71 (t, 1 H), 7.44 (dd, 1 H), 7.20 (d, 1 H), 6.99 (s, 1 H), 6.84-6.83 (m, 2 H), 6.46 (bs, 1 H), 5.97 (s, 2 H), 4.41 (bs, 2 H), 3.98 (s, 3 H).

EXAMPLE 29

2-amino-5-benzo[1,3]dioxol-5-ylmethyl-[1,2,4]triazolo[1,5-c]quinazolin-8-ol

[(I); R1=8-OH, X=phenyl, Z=CH$_2$, W=benzo[1,3]dioxol-5-yl]

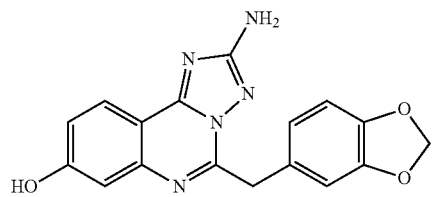

Operating as in Example 2, but employing benzo[1,3]dioxol-5-yl-acetyl chloride instead of (3-nitro-phenyl)-acetyl chloride and 2-amino-4-hydroxy-benzoic acid instead of 2-aminobenzoic acid, the title compound was obtained in 12% yield.

1H-NMR (400 MHz), δ (ppm, DMSO-d$_6$): 10.39 (bs, 1 H), 8.04 (d, 1 H), 7.15-7.12 (m, 2 H), 6.98 (s, 1 H), 6.83-6.82 (m, 2 H), 6.35 (bs, 2 H), 5.96 (s, 2 H), 4.36 (bs, 2 H).

EXAMPLE 30

5-benzo[1,3]dioxol-5-ylmethyl-8,10-difluoro-[1,2,4]triazolo[1,5-c]quinazolin-2-ylamine

[(I); R1=8,10-difluoro, X=phenyl, Z=CH₂, W=benzo[1,3]dioxol-5-yl]

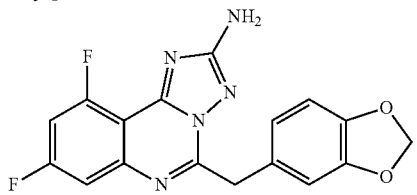

Operating as in Example 2, but employing benzo[1,3]dioxol-5-yl-acetyl chloride instead of (3-nitro-phenyl)-acetyl chloride and 2-amino-4,6-difluoro-benzoic acid instead of 2-aminobenzoic acid, the title compound was obtained in 14% yield.

1H-NMR (400 MHz), δ (ppm, DMSO-d₆): 7.61-7.54 (m, 2 H), 6.98 (s, 1 H), 6.84-6.83 (m, 2 H), 6.63 (bs, 2 H), 5.97 (s, 2 H), 4.42 (bs, 2 H).

EXAMPLE 31

5-benzo[1,3]dioxol-5-ylmethyl-10-chloro-[1,2,4]triazolo[1,5-c]quinazolin-2-ylamine

[(I); R1=10-Cl, X=phenyl, Z=CH₂, W=benzo[1,3]dioxol-5-yl]

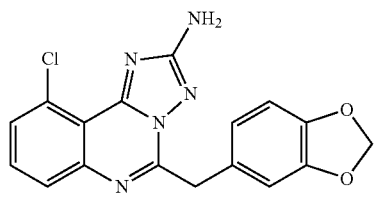

Operating as in Example 2, but employing benzo[1,3]dioxol-5-yl-acetyl chloride instead of (3-nitro-phenyl)-acetyl chloride and 2-amino-6-chloro-benzoic acid instead of 2-aminobenzoic acid, the title compound was obtained in 8% yield.

1H-NMR (400 MHz), δ (ppm, DMSO-d₆): 7.85 (m, 1 H), 7.75-7.74 (m, 2 H), 7.00 (s, 1 H), 6.86-6.85 (m, 2 H), 6.58 (bs, 2 H), 5.98 (s, 2 H), 4.45 (bs, 2 H).

EXAMPLE 32

8-fluoro-5-(5-methoxy-1H-indol-3-ylmethyl)-[1,2,4]triazolo[1,5-c]quinazolin-2-ylamine

[(I); R1=8-F, X=phenyl, Z=CH₂, W=5-methoxy-1H-indol-3-yl]

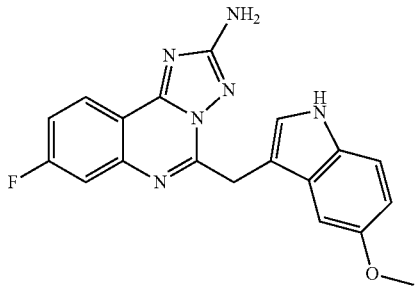 [SMILES: COc1ccc2[nH]cc(Cc3nc4cc(F)ccc4c4nc(N)nn34)c2c1]

Operating as in Example 2, but employing (5-methoxy-1H-indol)-acetyl chloride instead of (3-nitro-phenyl)-acetyl chloride and 2-amino-4-fluoro-benzoic acid instead of 2-aminobenzoic acid, the title compound was obtained in 13% yield.

1H-NMR (400 MHz), δ (ppm, DMSO-d₆): 10.78 (bs, 1 H), 8.26 (m, 1 H), 7.68 (dd, 1 H), 7.55 (m, 1 H), 7.25-7.20 (m, 3 H), 6.70 (dd, 1 H), 6.52 (bs, 2 H), 4.56 (bs, 2 H), 3.71 (s, 3 H).

EXAMPLE 33

8-fluoro-5-(2,34-trimethoxy-benzyl)-[1,2,4]triazolo[1,5-c]quinazolin-2-ylamine

[(I); R1=8-F, X=phenyl, Z=CH₂, W=3,4,5-trimethoxyphenyl]

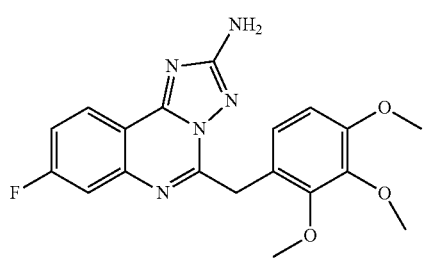 [SMILES: COc1ccc(Cc2nc3cc(F)ccc3c3nc(N)nn23)c(OC)c1OC]

Operating as in Example 2, but employing (2,3,4-trimethoxy-phenyl)-acetyl chloride instead of (3-nitro-phenyl)-acetyl chloride and 2-amino-4-fluoro-benzoic acid instead of 2-aminobenzoic acid, the title compound was obtained in 23% yield.

1H-NMR (400 MHz), δ (ppm, DMSO-d₆): 8.27 (m, 1 H), 7.72 (dd, 1 H), 7.57 (m, 1 H), 6.76 (s, 2 H), 6.52 (bs, 2 H), 4.44 (bs, 2 H), 3.72 (s, 6 H), 3.62 (s, 3 H).

EXAMPLE 34

5-(4-benzyloxy-3-methoxy-benzyl)-8-fluoro-[1,2,4]triazolo[1,5-c]quinazolin-2-ylamine

[(I); R1=8-F, X=phenyl, Z=CH₂, W=4-benzyloxy-3-trimethoxy-phenyl]

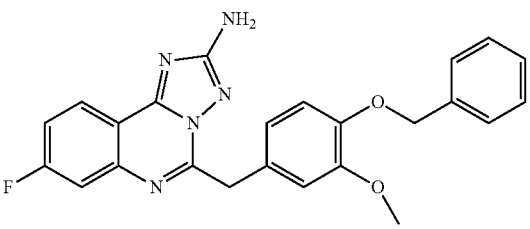 [SMILES: COc1cc(Cc2nc3cc(F)ccc3c3nc(N)nn23)ccc1OCc1ccccc1]

Operating as in Example 2, but employing (4-benzyloxy-3-trimethoxy-phenyl)-acetyl chloride instead of (3-nitrophenyl)-acetyl chloride and 2-amino-4-fluoro-benzoic acid instead of 2-aminobenzoic acid, the title compound was obtained in 16% yield.

1H-NMR (400 MHz), δ (ppm, DMSO-d₆): 8.27 (m, 1 H), 7.70 (dd, 1 H), 7.56 (m, 1 H), 7.41 (m, 2 H), 7.37 (m, 2 H), 7.31 (m, 1 H), 7.11 (d, 1 H), 6.95 (d, 1 H), 6.85 (dd, 1 H), 6.52 (bs, 2 H), 5.03 (s, 2 H), 4.43 (bs, 2 H), 3.74 (s, 3 H).

EXAMPLE 35

8-fluoro-5-(4-trifluoromethoxy-benzyl)-[1,2,4]triazolo[1,5-c]quinazolin-2-ylamine

[(I); R1=8-F, X=phenyl, Z=CH$_2$, W=4-trifluoromethoxyphenyl]

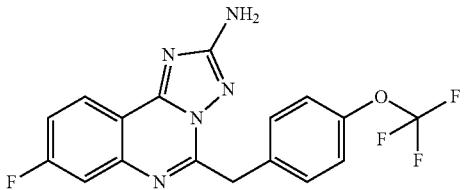 [SMILES: Nc1nc2c3ccc(F)cc3nc(Cc3ccc(OC(F)(F)F)cc3)n2n1]

Operating as in Example 2, but employing (4-trifluoromethoxy-phenyl)-acetyl chloride instead of (3-nitro-phenyl)-acetyl chloride and 2-amino-4-fluoro-benzoic acid instead of 2-aminobenzoic acid, the title compound was obtained in 24% yield.

1H-NMR (400 MHz), δ (ppm, DMSO-d$_6$): 8.28 (m, 1 H), 7.68 (dd, 1 H), 7.58 (m, 1 H), 7.53 (d, 2 H), 7.33 (d, 2 H), 6.53 (bs, 2 H), 4.56 (bs, 2 H).

EXAMPLE 36

5-benzo[1,3]dioxol-5-ylmethyl-8,10-dimethoxy-[1,2,4]triazolo[1,5-c]quinazolin-2-ylamine

[(I); R1=9,10-OCH$_3$, X=phenyl, Z=CH$_2$, W=benzo[1,3]dioxol-5-yl]

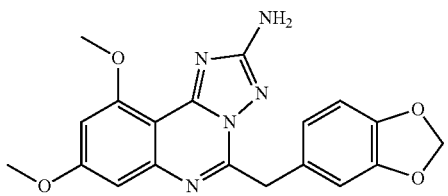 [SMILES: COc1cc(OC)c2c(c1)nc(Cc1ccc3c(c1)OCO3)n1nc(N)nc21]

Operating as in Example 2, but employing benzo[1,3]dioxol-5-yl-acetyl chloride instead of (3-nitro-phenyl)-acetyl chloride and 2-amino-4,5-dimethoxy-benzoic acid instead of 2-aminobenzoic acid, the title compound was obtained in 18% yield.

1H-NMR (400 MHz), δ (ppm, DMSO-d$_6$): 6.98 (s, 1 H), 6.90 (d, 1 H), 6.83-6.82 (m, 2 H), 6.75 (d, 1 H), 6.39 (bs, 1 H), 5.97 (s, 2 H), 4.37 (bs, 2 H), 3.94 (s, 3 H), 3.90 (s, 3 H).

EXAMPLE 37

5-(4-iodo-benzo[1,3]dioxol-5-ylmethyl)-[1,2,4]triazolo[1,5-c]quinazolin-2-ylamine

[(I); m=0, X=phenyl, Z=CH$_2$, W=benzo[1,3]dioxol-6-iodo-5-yl]

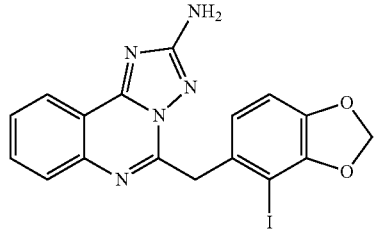 [SMILES: Nc1nc2c3ccccc3nc(Cc3ccc4c(c3I)OCO4)n2n1]

Operating as in Example 2, but employing benzo[1,3]dioxol-6-iodo-5-yl-acetyl chloride instead of (3-nitro-phenyl)-acetyl chloride, the title compound was obtained in 28% yield.

1H-NMR (400 MHz), δ (ppm, DMSO-d$_6$): 8.22 (d, 1 H), 7.78-7.74 (m, 2 H), 7.67 (m, 1 H), 7.42 (s, 1 H), 7.04 (s, 1 H), 6.51 (bs, 2 H), 6.07 (s, 2 H), 4.55 (bs, 2 H).

EXAMPLE 38

5-(4-bromo-benzo[1,3]dioxol-5-ylmethyl)-[1,2,4]triazolo[1,5-c]quinazolin-2-ylamine

[(I); m=0, X=phenyl, Z=CH$_2$, W=benzo[1,3]dioxol-6-bromo-5-yl]

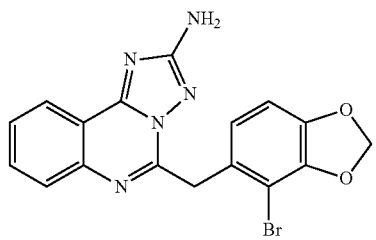 [SMILES: Nc1nc2c3ccccc3nc(Cc3ccc4c(c3Br)OCO4)n2n1]

Operating as in Example 2, but employing benzo[1,3]dioxol-6-bromo-5-yl-acetyl chloride instead of (3-nitro-phenyl)-acetyl chloride, the title compound was obtained in 23% yield.

1H-NMR (400 MHz), δ (ppm, DMSO-d$_6$): 8.22 (d, 1 H), 7.81-7.74 (m, 2 H), 7.67 (m, 1 H), 7.25 (s, 1 H), 7.05 (s, 1 H), 6.50 (bs, 2 H), 6.08 (s, 2 H), 4.55 (bs, 2 H).

Conversion of a compound of formula (I) into another compound of formula (I) as described under conversion (h).

EXAMPLE 39

5-(2-amino-[1,2,4]triazolo[1,5-c]quinazolin-5-ylmethyl)-benzene-1,3-diol

[(I); m=0, X=phenyl, Z=CH$_2$, W=3,4-dihydroxyphenyl]

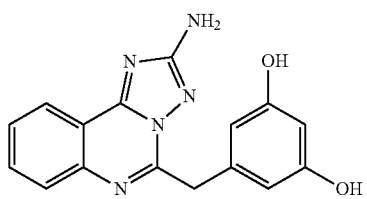 [SMILES: Nc1nc2c3ccccc3nc(Cc3cc(O)cc(O)c3)n2n1]

To a stirred suspension of 5-(3,5-dimethoxy-benzyl)-[1,2,4]triazolo[1,5-c]quinazolin-2-ylamine (0.10 g, 0.30 mmol), prepared as described in Example 4, in anhydrous dichloromethane (10 mL) was added dropwise, under argon, 1M BBr$_3$ solution (3 mL, 3 mmol) in DCM at 0-5° C. The ice bath was removed and the mixture was stirred at room temperature overnight. The reaction was diluted with ethyl acetate and washed with NaHCO$_3$ satured solution, then with water and brine. After drying over Na$_2$SO$_4$, the solvent was removed to give a crude that was crystallized twice from ethyl acetate to afford the title compound (0.70 g, 70% yield).

1H-NMR (400 MHz), δ (ppm, DMSO-$d_6$): 9.12 (bs, 2 H), 8.21 (d, 1 H), 7.90 (d, 1 H), 7.82 (m, 1 H), 7.68 (m, 1 H), 6.45 (bs, 2 H), 6.18 (d, 2 H), 6.05 (t, 1 H), 4.32 (bs, 2 H).

EXAMPLE 40

4-(2-amino-[1,2,4]triazolo[1,5-c]quinazolin-5-ylmethyl)-benzene-1,3-diol

[(I); m=0, X=phenyl, Z=CH$_2$, W=2,4-dihydroxyphenyl]

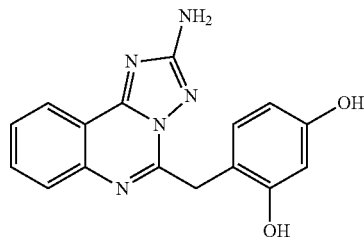 [SMILES: Nc1nc2c3ccccc3nc(Cc3ccc(O)cc3O)n2n1]

Operating as in Example 39, but employing 5-(2,4-dimethoxy-benzyl)-8-nitro-[1,2,4]triazolo[1,5-c]quinazolin-2-ylamine, prepared as described in Example 5, instead of 5-(3,5-dimethoxy-benzyl)-[1,2,4]triazolo[1,5-c]quinazolin-2-ylamine, the title compound was obtained in 76% yield.

1H-NMR (400 MHz), δ (ppm, DMSO-$d_6$): 9.33 (bs, 1 H), 9.10 (bs, 1 H), 8.20 (d, 1 H), 7.83-7.75 (m, 2 H), 7.65 (m, 1 H), 6.79 (d, 1 H), 6.45 (bs, 2 H), 6.32 (d, 1 H), 6.12 (dd, 1 H), 4.32 (bs, 2 H).

EXAMPLE 41

4-(2-amino-[1,2,4]triazolo[1,5-c]quinazolin-5-ylmethyl)-phenol

[(I); m=0, X=phenyl, Z=CH$_2$, W=4-hydroxyphenyl]

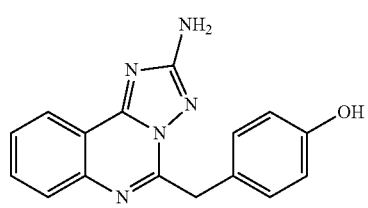 [SMILES: Nc1nc2c3ccccc3nc(Cc3ccc(O)cc3)n2n1]

Operating as in Example 39, but employing 5-(4-methoxy-benzyl)-[1,2,4]triazolo[1,5-c]quinazolin-2-ylamine, prepared as described in Example 3, instead of 5-(3,5-dimethoxy-benzyl)-[1,2,4]triazolo[1,5-c]quinazolin-2-ylamine, the title compound was obtained in 71% yield.

1H-NMR (400 MHz), δ (ppm, DMSO-$d_6$): 9.28 (bs, 1 H), 8.20 (d, 1 H), 7.88 (d, 1 H), 7.81 (m, 1 H), 7.67 (m, 1 H), 7.19 (d, 2 H), 6.68 (d, 2 H), 6.46 (bs, 2 H), 4.39 (bs, 2 H).

EXAMPLE 42

2-(2-amino-[1,2,4]triazolo[1,5-c]quinazolin-5-ylmethyl)-benzene-1,4-diol [(I); m=0, X=phenyl, Z=CH$_2$, W=2,4-hydroxyphenyl]

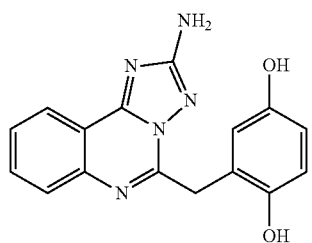 [SMILES: Nc1nc2c3ccccc3nc(Cc3cc(O)ccc3O)n2n1]

Operating as in Example 39, but employing 5-(2,5-dimethoxy-benzyl)-[1,2,4]triazolo[1,5-c]quinazolin-2-ylamine, prepared as described in Example 6, instead of 5-(3,5-dimethoxy-benzyl)-[1,2,4]triazolo[1,5-c]quinazolin-2-ylamine, the title compound was obtained in 41% yield.

1H-NMR (400 MHz), δ (ppm, DMSO-$d_6$): 8.80 (bs, 1 H), 8.52 (bs, 1 H), 8.22 (d, 1 H), 7.87-7.78 (m, 2 H), 7.67 (m, 1 H), 6.65 (d, 1 H), 6.48-6.45 (m, 3 H), 6.36 (d, 1 H), 4.37 (bs, 2 H).

EXAMPLE 43

4-(2-amino-[1,2,4]triazolo[1,5-c]quinazolin-5-ylmethyl)-benzene-1,2-diol [(I); m=0, X=phenyl, Z=CH$_2$, W=3,4-hydroxyphenyl]

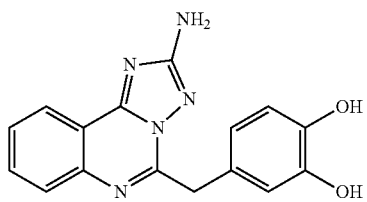 [SMILES: Nc1nc2c3ccccc3nc(Cc3ccc(O)c(O)c3)n2n1]

Operating as in Example 39, but employing 5-(3,4-dimethoxy-benzyl)-[1,2,4]triazolo[1,5-c]quinazolin-2-ylamine, prepared as described in Example 7, instead of 5-(3,5-dimethoxy-benzyl)-[1,2,4]triazolo[1,5-c]quinazolin-2-ylamine, the title compound was obtained in 37% yield.

1H-NMR (400 MHz), δ (ppm, DMSO-$d_6$): 8.38 (bs, 2 H), 8.20 (d, 1 H), 7.89 (d, 1 H), 7.81 (m, 1 H), 7.66 (m, 1 H), 6.74 (s, 1 H), 6.66-6.64 (m, 2 H), 6.44 (bs, 2 H), 4.32 (bs, 2 H).

EXAMPLE 44

4-(2-amino-[1,2,4]triazolo[1,5-c]quinazolin-5-ylmethyl)-2-bromo-phenol

[(I); m=0, X=phenyl, Z=CH$_2$, W=3-bromo-4-hydroxyphenyl]

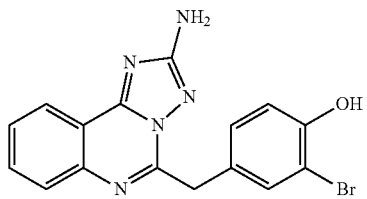 [SMILES: Nc1nc2c3ccccc3nc(Cc3ccc(O)c(Br)c3)n2n1]

Operating as in Example 39, but employing 5-(3-bromo-4-methoxy-benzyl)-[1,2,4]triazolo[1,5-c]quinazolin-2-ylamine, prepared as described in Example 11, instead of 5-(3,5-dimethoxy-benzyl)-[1,2,4]triazolo[1,5-c]quinazolin-2-ylamine, the title compound was obtained in 68% yield.

1H-NMR (400 MHz), δ (ppm, DMSO-$d_6$): 10.12 (bs, 1) 8.20 (d, 1), 7.87 (d, 1H), 7.80 (m, 1), 7.67 (m, 1H), 7.52 (d, 1), 7.17 (dd, 1), 6.87 (d, 1), 6.48 (bs, 2), 4.41 (bs, 2)

Conversion of a compound of formula (I) into another compound of formula (I) as described under conversion (f).

EXAMPLE 45

5-(3-amino-benzyl)-[1,2,4]triazolo[1,5-c]quinazolin-2-ylamine

[(I); m=0, X=phenyl, Z=$CH_2$, W=3-aminophenyl]

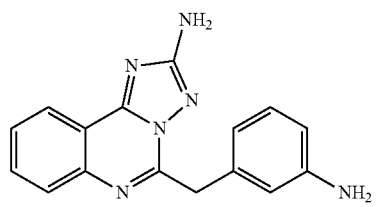

To a solution of 5-(3-nitro-benzyl)-[1,2,4]triazolo[1,5-c]quinazolin-2-ylamine (0.10 g, 0.31 mmol), prepared as described in Example 2, in N,N-dimethylformamide (10 mL), 10% Pd/C (50% w/w, 0.05 g) was added. The mixture was reacted in Parr Apparatus at 40 p.s.i. for 5 h. The suspension was filtered through Celite®. After washing the filter with methanol, the solution was evaporated to dryness. The crude was twice crystallized from ethyl acetate to provide the title product (0.062 g, 67% yield).

1H-NMR (400 MHz), δ (ppm, DMSO-$d_6$): 8.21 (d, 1 H), 7.89 (d, 1 H), 7.81 (m, 1 H), 7.68 (m, 1 H), 7.01 (t, 1 H), 6.66 (d, 1 H), 6.63 (d, 1 H), 6.45-6.28 (m, 4 H), 4.39 (bs, 2 H).

EXAMPLE 46

5-(2,5-dimethoxy-benzyl)-[1,2,4]triazolo[1,5-c]quinazoline-2,8-diamine

[(I); R1=8—$NH_2$, X=phenyl, Z=$CH_2$, W=2,4-dimethoxyphenyl]

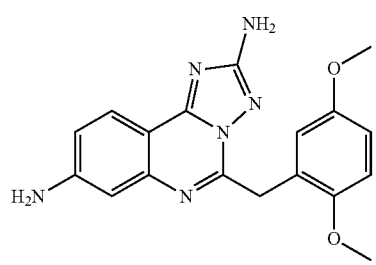 [SMILES: COc1ccc(OC)c(Cc2nc3cc(N)ccc3c3nc(N)nn23)c1]

Operatine as Example 45, but employing 5-(2,5-dimethoxy-benzyl)-[1,2,4]triazolo[1,5-c]quinazoline-8-nitro-2-ylamine prepared as described in Example 9 instead of 5-(3-nitro-benzyl)-[1,2,4]triazolo[1,5-c]quinazolin-2-ylamine, the title compound was obtained in 53% yield.

1H-NMR (400 MHz), δ (ppm, DMSO-$d_6$): 7.83 (d, 1 H), 6.94-6.90 (m, 2 H), 6.75 (d, 1 H), 6.57 (d, 1 H), 6.42 (dd, 2 H), 6.68 (bs, 2 H), 6.16 (bs, 2 H), 4.26 (bs, 2 H), 3.74 (s, 3 H), 3.73 (s, 3 H).

EXAMPLE 47

5-benzo[1,3]dioxol-5-ylmethyl-[1,2,4]triazolo[1,5-c]quinazoline-2,8-diamine

[(I); R1=8—$NH_2$, X=phenyl, Z=$CH_2$, W=5-benzo[1,3]dioxol-5-yl]

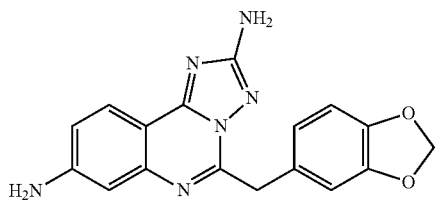 [SMILES: Nc1ccc2c(c1)nc(Cc1ccc3c(c1)OCO3)n1nc(N)nc21]

Operating as in Example 45, but employing 5-benzo[1,3]dioxol-5-ylmethyl-[1,2,4]triazolo[1,5-c]quinazoline-8-nitro-2-ylamine, prepared as described in Example 13, instead of 5-(3-nitro-benzyl)-[1,2,4]triazolo[1,5-c]quinazolin-2-ylamine, the title compound was obtained in 47% yield.

1H-NMR (400 MHz), δ (ppm, DMSO-$d_6$): 7.85 (d, 1), 6.98 (bs, 1), 6.92 (dd, 1), 8.64 (d, 1), 6.84-6.83 (m, 2), 6.21 (bs, 2), 5.97 (s, 2), 5.94 (bs, 2), 4.31 (bs, 2)

EXAMPLE 48

2-amino-5-benzo[1,3]dioxol-5-ylmethyl-[1,2,4]triazolo[1,5-c]quinazoline-8-sulfonic acid amide

[(I); R1=8-$SO_2NH_2$, X=phenyl, Z=$CH_2$, W=5-benzo[1,3]dioxol-5-yl]

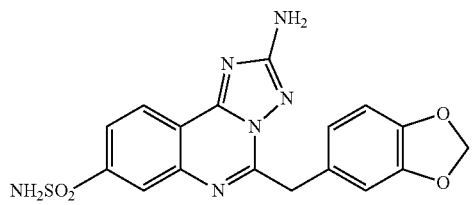

Steps 1 and 2
2-(2-Benzo[1,3]dioxol-5-yl-acetylamino)-4-sulfamoyl-benzoic acid (V)

To a solution of benzo[1,3]dioxol-5-yl-acetic acid (0.18 g, 1 mmol) in dry N,N-dimethylformamide (15 mL), 1,1-carbonyldiimidazole (0.18 g, 1.1 mmol) was added. The mixture was stirred at room temperature for 1 h, then 2-amino-4-sulfamoyl-benzoic acid (0.22 g, 1 mmol) was added portion wise. The reaction was stirred at room temperature for 2 days, diluted with dichloromethane and washed with 1N HCl solution, then with water and brine. The organic phase was dried over $Na_2SO_4$, filtered and evaporated to give a crude that was purified by flash column chromatography on silica gel eluting with ethyl acetate/hexane 8/2, to afford the title compound (0.20 g, 53% yield).

1H-NMR (400 MHz), δ (ppm, DMSO-$d_6$): 14.62 (bs, 1 H), 12.24 (bs, 1 H), 8.93 (d, 1 H), 8.09 (d, 1 H), 7.37 (dd, 1 H), 7.25 (bs, 2 H), 6.90 (d, 1 H), 6.85 (d, 1 H), 6.80 (dd, 1 H), 5.97 (s, 2 H), 3.54 (bs, 2 H).

Steps 3 and 4

2-Amino-5-benzo[1,3]dioxol-5-ylmethyl-[1,2,4]triazolo[1,5-c]quinazoline-8-sulfonic acid amide (I)

A mixture of 2-(2-benzo[1,3]dioxol-5-yl-acetylamino)-4-sulfamoyl-benzoic acid (0.10 g, 0.26 mmol), acetic acid (1.5 mL) and acetic anhydride (0.10 mL, 1.06 mmol) was stirred at reflux for 1 h. The reaction was diluted with ethyl acetate and washed with NaHCO$_3$ satured solution, then with water and brine. The organic phase was dried over Na$_2$SO$_4$, filtered and evaporated to give the 2-benzo[1,3]dioxol-5-ylmethyl-4-oxo-4H-benzo[d][1,3]oxazine-7-sulfonic acid amide intermediate (0.032 g) as yellow oil. To a solution of 2-benzo[1,3]dioxol-5-ylmethyl-4-oxo-4H-benzo[d][1,3]oxazine-7-sulfonic acid amide (0.032 g, 0.09 mmol) in dry pyridine (1 mL) was added aminoguanidine hydrogencarbonate (0.013 g, 0.098 mmol) and the mixture was heated under microwave condition at 180° C. for 1.5 h. The solvent was then evaporated and the crude was taken up in methanol to give the title compound (0.013 g, 12% yield).

1H-NMR (400 MHz), δ (ppm, DMSO-d$_6$): 8.36 (d, 1 H), 8.25 (d, 1 H), 8.00 (dd, 1 H), 7.59 (s, 2 H), 7.01 (d, 1 H), 6.86-6.84 (m, 2 H), 6.60 (bs, 2 H), 5.98 (s, 2 H), 4.46 (bs, 2 H).

EXAMPLE 49

[(R)-(2-amino-[1,2,4]triazolo[1,5-c]quinazolin-5-yl)-phenyl-methyl]-carbamic acid tert-butyl ester

[(I); m=0, X=phenyl, Z=CHNHCOOC$_4$H$_9$, W=phenyl]

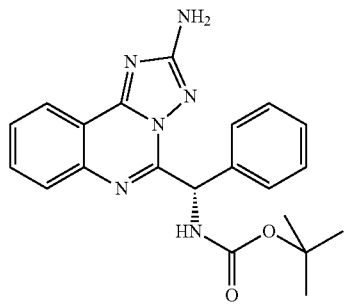 [SMILES: CC(C)(C)OC(=O)N[C@@H](c1ccccc1)c1nc2ccccc2c2nc(N)nn12]

Steps 1, 2, 3 and 4

To a stirred mixture of commercially available (R)-tert-butoxycarbonylamino-phenyl-acetic acid (1.00 g, 3.98 mmol), dimethyl-pyridin-4-yl-amine (0.49 g, 3.98 mmol) and N-ethyl-N'-(3-dimethylaminopropyl)carbodiimide (0.84 g, 4.38 mmol) in anhydrous dichloromethane (30 mL), a solution of 2-aminobenzoic acid (0.55 g, 3.98 mmol) and triethylamine (0.56 mL, 4.38 mmol) in anhydrous dichloromethane (6 mL) was added drop wise at 0-5° C. The reaction was stirred at room temperature for 4 h, then the resulting solution was washed with 1N HCl solution, water and brine After drying over Na$_2$SO$_4$, the solvent was removed to give the intermediate 2-((R)-2-tert-butoxycarbonylamino-2-phenyl-acetylamino)-benzoic acid. To a solution of this intermediate in dry dichloromethane (20 mL), dimethyl-pyridin-4-yl-amine (0.19 g, 1.59 mmol) and N-ethyl-N'-(3-dimethylaminopropyl)carbodiimide (0.84 g, 4.38 mmol) were added. The mixture was stirred at room temperature for 2 h, then washed with 1N HCl solution, then with water and brine, dried over Na$_2$SO$_4$ and evaporated to dryness. The intermediate [(R)-(4-oxo-4H-benzo[d][1,3]oxazin-2-yl)-phenyl-methyl]-carbamic acid tert-butyl ester was dissolved in dry pyridine (5 mL) and aminoguanidine hydrogencarbonate (0.60 g, 4.38 mmol) was added. The mixture was heated under microwave condition at 180° C. for 30 minutes, the solvent was then evaporated and the crude purified by flash column chromatography on silica gel eluting with DCM/CH$_3$OH 96/4, to afford title compound (0.16 g, 10% yield).

1H-NMR (400 MHz), δ (ppm, DMSO-d$_6$): 8.23 (d, 1 H), 7.97 (d, 1 H), 7.85 (m, 1 H), 7.82 (s, 1 H), 7.70 (m, 1 H), 7.50-7.46 (m, 2 H), 7.32-7.28 (m, 2 H), 7.23 (m, 1 H), 6.51 (bs, 3 H), 1.50 (s, 9 H).

EXAMPLE 50

[(S)-(2-amino-[1,2,4]triazolo[1,5-c]quinazolin-5-yl)-phenyl-methyl]-carbamic acid tert-butyl ester

[(I); m=0, X=phenyl, Z=CHNHCOOC$_4$H$_9$, W=phenyl]

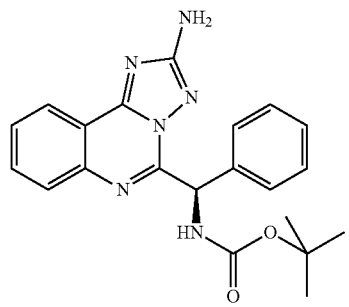 [SMILES: CC(C)(C)OC(=O)N[C@H](c1ccccc1)c1nc2ccccc2c2nc(N)nn12]

Operating as in Example 49, but employing (S)-tert-butoxycarbonylamino-phenyl-acetic acid instead of (R)-tert-butoxycarbonylamino-phenyl-acetic acid, the title compound was obtained in 8% yield.

1H-NMR (400 MHz), δ (ppm, DMSO-d$_6$): 8.23 (d, 1 H), 7.97 (d, 1 H), 7.85 (m, 1 H), 7.82 (s, 1 H), 7.70 (m, 1 H), 7.50-7.46 (m, 2 H), 7.32-7.28 (m, 2 H), 7.23 (m, 1 H), 6.51 (bs, 3 H), 1.50 (s, 9 H).

Conversion of a compound of formula (I) into another compound of formula (I) as described under conversion (h).

EXAMPLE 51

5-((R)-amino-phenyl-methyl)-[1,2,4]triazolo[1,5-c]quinazolin-2-ylamine

[(I); m=0, X=phenyl, Z=Z=CHNH$_2$, W=phenyl]

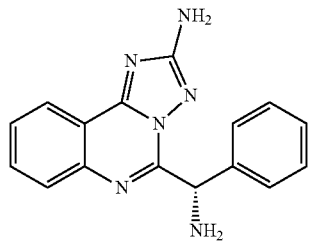 [SMILES: Nc1nc2c3ccccc3nc([C@@H](N)c3ccccc3)n2n1]

To a suspension of [(R)-(2-amino-[1,2,4]triazolo[1,5-c]quinazolin-5-yl)-phenyl-methyl]-carbamic acid tert-butyl ester (0.05 g, 0.13 mmol), prepared as described in Example 49, in dichloromethane (4 mL), trifluoroacetic acid (1 mL) was added. The mixture was stirred at room temperature for 1 h, then the solvent was evaporated and the residue was diluted with ethyl acetate and washed with NaHCO$_3$ satured solution then with water and brine. The organic phase was dried over Na₂SO₄, filtered and evaporated to provide the title compound (0.02 g, 65% yield).

1H-NMR (400 MHz), δ (ppm, DMSO-d₆): 8.23 (d, 1 H), 7.97 (d, 1 H), 7.85 (m, 1 H), 7.70 (m, 1 H), 7.50-7.46 (m, 2 H), 7.32-7.28 (m, 2 H), 7.23 (m, 1 H), 6.48 (bs, 2 H), 5.70 (bs, 1 H), 2.97 (bs, 2 H).

EXAMPLE 52

5-((S)-amino-phenyl-methyl)-[1,2,4]triazolo[1,5-c]quinazolin-2-ylamine

[(I); m=0, X=phenyl, Z=Z=CHNH₂, W=phenyl]

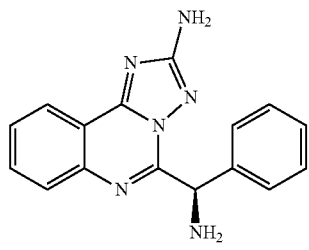 [SMILES: Nc1nc2c3ccccc3nc([C@H](N)c3ccccc3)n2n1]

Operating as Example 51, but employing [(S)-(2-amino-[1,2,4]triazolo[1,5-c]quinazolin-5-yl)-phenyl-methyl]-carbamic acid tert-butyl ester instead of [(R)-(2-amino-[1,2,4]triazolo[1,5-c]quinazolin-5-yl)-phenyl-methyl]-carbamic acid tert-butyl ester, the title compound was obtained in 61% yield.

1H-NMR (400 MHz), δ (ppm, DMSO-d₆): 8.23 (d, 1 H), 7.97 (d, 1 H), 7.85 (m, 1 H), 7.70 (m, 1 H), 7.50-7.46 (m, 2 H), 7.32-7.28 (m, 2 H), 7.23 (m, 1 H), 6.48 (bs, 2 H), 5.70 (bs, 1 H), 2.97 (bs, 2 H).

EXAMPLE 53

9-aminomethyl-5-benzo[1,3]dioxol-5-ylmethyl-[1,2,4]triazolo[1,5-c]quinazolin-2-ylamine

[(I); R1=9-CH₂NH₂, X=phenyl, Z=CH₂, W=5-benzo[1,3]dioxol-5-yl]

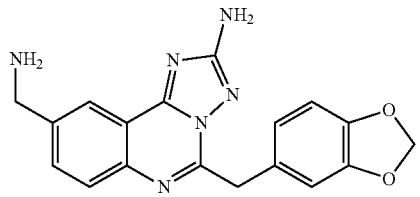 [SMILES: NCc1ccc2nc(Cc3ccc4c(c3)OCO4)n3nc(N)nc3c2c1]

To a solution of 2-amino-5-benzo[1,3]dioxol-5-ylmethyl-[1,2,4]triazolo[1,5-c]quinazoline-9-carbonitrile (0.07 g, 0.20 mmol), prepared as described in Example 25, in a mixture of tetrahydrofuran (5 mL) and methanol (5 mL), were sequentially added cobalt(II) chloride (0.11 g, 0.81 mmol) and sodium borohydride (0.03 g, 0.81 mmol). The reaction was stirred at room temperature overnight, then the solvent was evaporated. The residue was dissolved in CHCl₃/CH₃OH 9/1 and washed with ammonium hydroxide solution (pH 12). The organic phase was dried over Na₂SO₄, filtered and evaporated to obtain a crude which was purified by preparative HPLC to give the title compound (0.01 g, 7% yield).

1H-NMR (400 MHz), δ (ppm, DMSO-d₆): 8.16 (d, 1.H), 7.80 (d, 1.H), 7.75 (dd, 1H), 6.99 (s, 1.H), 6.84-6.83 (m, 2.H), 6.42 (bs, 2.H), 5.96 (s, 2.H), 4.41 (bs, 2.H), 3.92 (bs, 2.H), 2.30 (bs, 2.H)

Conversion of a compound of formula (I) into another compound of formula (I) as described under conversion (g)

EXAMPLE 54

5-benzo[1,3]dioxol-5-ylmethyl-8-morpholin-4-yl-[1,2,4]triazolo[1,5-c]quinazolin-2-ylamine

[(I); R1=8-C₄H₈NO, X=phenyl, Z=CH₂, W=5-benzo[1,3]dioxol-5-yl]

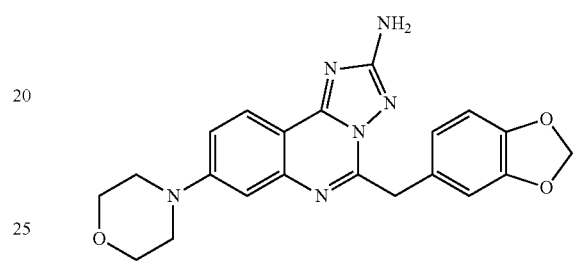

To 5-benzo[1,3]dioxol-5-ylmethyl-8-fluoro-[1,2,4]triazolo[1,5-c]quinazolin-2-ylamine (0.05 g, 0.15 mmol), prepared as described in Example 21, morpholine (1 mL) was added and the mixture was heated at 140° C. for 2 h. The reaction was cooled at room temperature, the solid precipitated was filtered and washed with a mixture MeOH/H₂O 9:1, to provide the title compound (0.03 g, 50% yield).

1H-NMR (400 MHz), δ (ppm, DMSO-d₆): 7.99 (d, 1 H), 7.39 (dd, 1 H), 7.16 (d, 1 H), 6.98 (s, 1 H), 6.83-6.82 (m, 2 H), 6.31 (bs, 2 H), 5.96 (s, 2 H), 4.35 (bs, 2 H), 3.76 (t, 4 H), 3.31 (t, 4 H).

EXAMPLE 55

5-benzo[1,3]dioxol-5-ylmethyl-8-(4-methyl-piperazin-1-yl)[1,2,4]triazolo[1,5-c]quinazolin-2-ylamine

[(I); R1=8-C₆H₁₁N₂, X=phenyl, Z=CH₂, W=5-benzo[1,3]dioxol-5-yl]

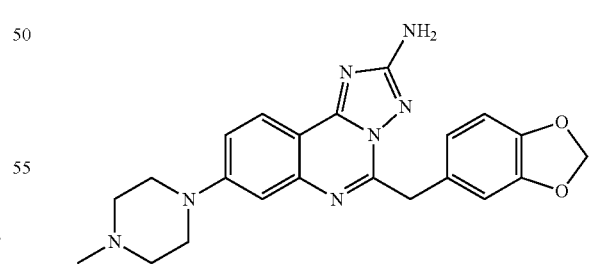

Operating as in Example 54, but employing N-methylpiperazine instead of morpholine, the title compound was obtained in 53% yield.

1H-NMR (400 MHz), δ (ppm, DMSO-d₆): 7.97 (d, 1 H), 7.38 (dd, 1 H), 7.13 (d, 1 H), 6.98 (s, 1 H), 6.83-6.81 (m, 2 H), 6.30 (bs, 2 H), 5.96 (s, 2 H), 4.35 (bs, 2 H), 3.35 (t, 4 H), 2.46 (t, 4 H).

EXAMPLE 56

2-(2-amino-5-benzo[1,3]dioxol-5-ylmethyl-[1,2,4]triazolo[1,5-c]quinazolin-8-ylamino)-ethanol

[(I); R1=2-$C_2H_6NO$, X=phenyl, Z=$CH_2$, W=5-benzo[1,3]dioxol-5-yl]

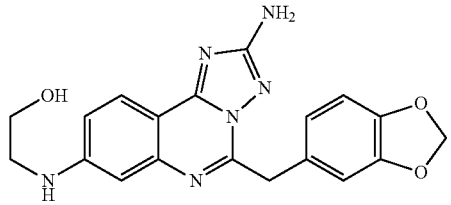 [SMILES: Nc1nc2c3ccc(NCCO)cc3nc(Cc3ccc4c(c3)OCO4)n2n1]

Operating as in Example 54, but employing 2-hydroxyethylamine instead of morpholine, the title compound was obtained in 61% yield.

1H-NMR (400 MHz), δ (ppm, DMSO-$d_6$): 7.83 (d, 1 H), 7.00 (dd, 1 H), 6.97 (s, 1 H), 6.83-6.82 (m, 2 H), 6.76 (d, 1 H), 6.48 (t, 1 H), 6.21 (bs, 2 H), 5.96 (s, 2 H), 4.75 (t, 1 H), 4.31 (bs, 2 H), 3.59 (m, 2 H), 3.21 (m, 2 H).

EXAMPLE 57

5-benzo[1,3]dioxol-5-ylmethyl-N*8*-(2-morpholin-4-yl-ethyl)-[1,2,4]triazolo[1,5-c]quinazoline-2,8-diamine

[(I); R1=2-$C_6H_{13}N_2O$, X=phenyl, Z=$CH_2$, W=5-benzo[1,3]dioxol-5-yl]

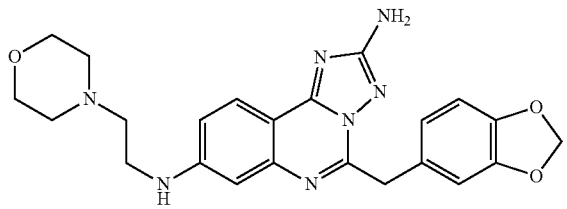 [SMILES: Nc1nc2c3ccc(NCCN4CCOCC4)cc3nc(Cc3ccc4c(c3)OCO4)n2n1]

Operating as in Example 54, but employing 2-morpholin-4-yl-ethylamine instead of morpholine, the title compound was obtained in 73% yield.

1H-NMR (400 MHz), δ (ppm, DMSO-$d_6$): 7.87 (d, 1 H), 7.04 (dd, 1 H), 6.98 (s, 1 H), 6.84-6.83 (m, 2 H), 6.78 (bs, 1 H), 6.39 (bs, 1 H), 6.23 (bs, 2 H), 5.97 (s, 2 H), 4.32 (bs, 2 H), 3.61 (m, 4 H), 3.35 (m, 2 H), 2.55-2.46 (m, 6 H).

EXAMPLE 58

5-benzo[1,3]dioxol-5-ylmethyl-N*8*-(2-methoxyethyl)-[1,2,4]triazolo[1,5-c]quinazoline-2,8-diamine

[(I); R1=2-$C_3H_8NO$, X=phenyl, Z=$CH_2$, W=5-benzo[1,3]dioxol-5-yl]

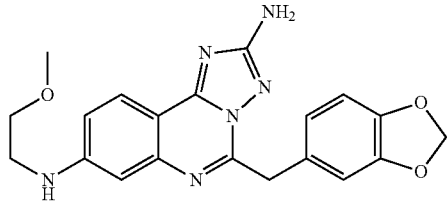 [SMILES: COCCNc1ccc2c(c1)nc(Cc1ccc3c(c1)OCO3)n1nc(N)nc21]

Operating as in Example 54, but employing 2-methoxyethylamine instead of morpholine, the title compound was obtained in 55% yield.

1H-NMR (400 MHz), δ (ppm, DMSO-$d_6$): 7.86 (d, 1 H), 7.05 (dd, 1 H), 6.98 (s, 1 H), 6.84-6.83 (m, 2 H), 6.78 (d, 1 H), 6.55 (bs, 1 H), 6.23 (bs, 2 H), 5.97 (s, 2 H), 4.32 (bs, 2 H), 3.55 (t, 2 H), 3.33-3.31 (m, 5 H).

EXAMPLE 59

5-benzo[1,3]dioxol-5-ylmethyl-N*8*-(2-dimethylamino-ethyl)-[1,2,4]triazolo[1,5-c]quinazoline-2,8-diamine

[(I); R1=7-$C_4H_{11}N_2$, X=phenyl, Z=$CH_2$, W=5-benzo[1,3]dioxol-5-yl]

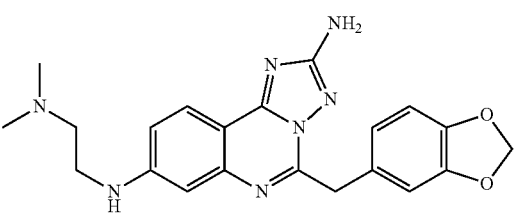 [SMILES: CN(C)CCNc1ccc2c(c1)nc(Cc1ccc3c(c1)OCO3)n1nc(N)nc21]

Operating as in Example 54, but employing N,N-dimethylethane-1,2-diamine instead of morpholine, the title compound was obtained in 55% yield.

1H-NMR (400 MHz), δ (ppm, DMSO-$d_6$): 7.87 (d, 1 H), 7.05 (dd, 1 H), 6.98 (s, 1 H), 6.84-6.83 (m, 2 H), 6.78 (d, 1 H), 6.37 (t, 1 H), 6.23 (bs, 2 H), 5.97 (s, 2 H), 4.32 (bs, 2 H), 3.26 (m, 2 H), 2.57 (m, 2 H), 2.28 (s, 6 H).

EXAMPLE 60

5-benzo[1,3]dioxol-5-ylmethyl-N*8*-(2-pyrrolidin-1-yl-ethyl)-[1,2,4]triazolo[1,5-c]quinazoline-2,8-diamine

[(I); R1=8-$C_6H_{15}N_2$, X=phenyl, Z=$CH_2$, W=5-benzo[1,3]dioxol-5-yl]

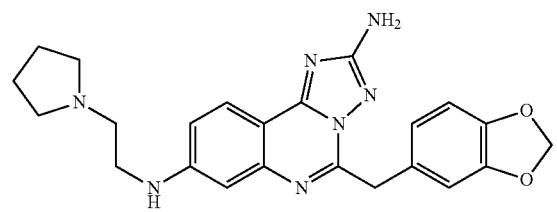 [SMILES: Nc1nc2c3ccc(NCCN4CCCC4)cc3nc(Cc3ccc4c(c3)OCO4)n2n1]

Operating as in Example 54, but employing 2-(pyrrolidin-1-yl)ethanamine instead of morpholine, the title compound was obtained in 41% yield.

1H-NMR (400 MHz), δ (ppm, DMSO-$d_6$): 7.87 (d, 1 H), 7.04 (dd, 1 H), 6.98 (s, 1 H), 6.84-6.83 (m, 2 H), 6.77 (d, 1 H), 6.45 (t, 1 H), 6.23 (bs, 2 H), 5.97 (s, 2 H), 4.32 (bs, 2 H), 3.32 (m, 2 H), 2.75-2.67 (m, 6 H), 1.74 (m, 4 H).

EXAMPLE 61

3-(2-amino-5-benzo[1,3]dioxol-5-ylmethyl-[1,2,4]triazolo[1,5-c]quinazolin-8-ylamino)-propan-1-ol

[(I); R1=8-C$_3$H$_8$NO, X=phenyl, Z=CH$_2$, W=5-benzo[1,3]dioxol-5-yl]

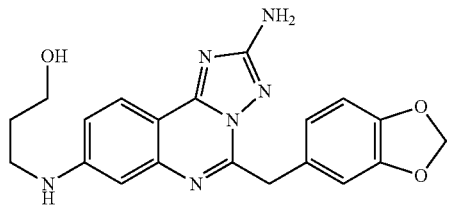 [SMILES: Nc1nc2c3ccc(NCCCO)cc3nc(Cc3ccc4c(c3)OCO4)n2n1]

Operating as in Example 54, but employing 3-amino-propan-1-olo instead of morpholine, the title compound was obtained in 28% yield.

1H-NMR (400 MHz), δ (ppm, DMSO-d$_6$): 7.85 (d, 1 H), 6.98-6.96 (m, 2 H), 6.97 (s, 1 H), 6.83-6.82 (m, 2 H), 6.72 (d, 1 H), 6.49 (t, 1 H), 6.21 (bs, 2 H), 5.96 (s, 2 H), 4.50 (t, 1 H), 4.31 (bs, 2 H), 3.53 (m, 2 H), 3.19 (m, 2 H), 1.74 (m, 2 H).

EXAMPLE 62

N*8*-(2-amino-ethyl)-5-benzo[1,3]dioxol-5-ylmethyl-[1,2,4]triazolo[1,5-c]quinazoline-2,8-diamine

[(I); R1=8-C$_2$H$_7$N$_2$, X=phenyl, Z=CH$_2$, W=5-benzo[1,3]dioxol-5-yl]

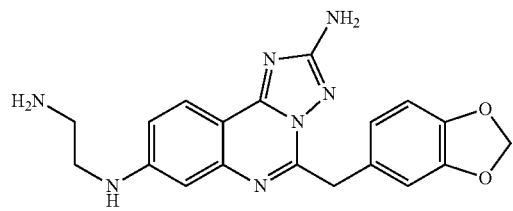 [SMILES: NCCNc1ccc2c(c1)nc(Cc1ccc3c(c1)OCO3)n1nc(N)nc21]

Operating as in Example 54, but employing ethane-1,2-diamine instead of morpholine, the title compound was obtained in 67% yield.

1H-NMR (400 MHz), δ (ppm, DMSO-d$_6$): 7.85 (d, 1 H), 7.00-6.97 (m, 2 H), 6.98 (s, 1 H), 6.83-6.82 (m, 2 H), 6.75 (d, 1 H), 6.50 (t, 1 H), 6.21 (bs, 2 H), 5.96 (s, 2 H), 4.31 (bs, 2 H), 3.14 (m, 2 H), 2.76 (m, 2 H), 2.09 (bs, 2 H).

EXAMPLE 63

2-[2-amino-5-(5-methoxy-1H-indol-3-ylmethyl)-[1,2,4]triazolo[1,5-c]quinazolin-8-ylamino]-ethanol

[(I); R1=8-C$_2$H$_6$NO, X=phenyl, Z=CH$_2$, W=5-methoxy-1H-indol-3-yl]

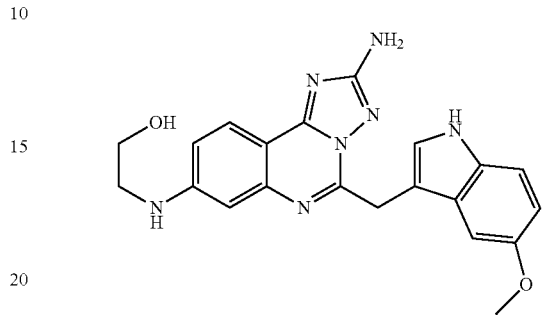

Operating as in Example 54, but employing 8-fluoro-5-(5-methoxy-1H-indol-3-ylmethyl)-[1,2,4]triazolo[1,5-c]quinazolin-2-ylamine, prepared as described in Example 32, instead of 5-benzo[1,3]dioxol-5-ylmethyl-8-fluoro-[1,2,4]triazolo[1,5-c]quinazolin-2-ylamine and 2-hydroxy-ethylamine instead of morpholine, the title compound was obtained in 35% yield.

1H-NMR (400 MHz), δ (ppm, DMSO-d$_6$): 10.75 (bs, 1H), 7.85 (d, 1 H), 7.23-7.20 (m, 3 H), 7.01 (dd, 1 H), 6.76 (d, 1 H), 6.69 (dd, 1 H), 6.25 (bs, 2 H), 4.46 (bs, 2 H), 3.71 (s, 3 H), 3.59 (m, 2 H), 3.20 (m, 2 H).

EXAMPLE 64

2-[2-amino-5-(2,3,4-trimethoxy-benzyl)-[1,2,4]triazolo[1,5-c]quinazolin-8-ylamino]-ethanol

[(I); R1=8-C$_2$H$_6$NO, X=phenyl, Z=CH$_2$, W=3,4,5-trimethoxy-phenyl]

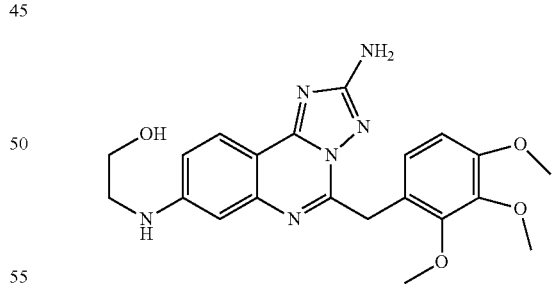

Operating as in Example 54, but employing 8-fluoro-5-(2,3,4-trimethoxy-benzyl)-[1,2,4]triazolo[1,5-c]quinazolin-2-ylamine prepared as described in Example 33, instead of 5-benzo[1,3]dioxol-5-ylmethyl-8-fluoro-[1,2,4]triazolo[1,5-c]quinazolin-2-ylamine and 2-hydroxy-ethylamine instead of morpholine, the title compound was obtained in 27% yield.

1H-NMR (400 MHz), δ (ppm, DMSO-d$_6$): 7.86 (d, 1 H), 7.03 (dd, 1 H), 6.78 (d, 1 H), 6.74 (s, 1 H), 6.48 (t, 1 H), 6.22 (bs, 2 H), 4.75 (t, 1 H), 4.34 (bs, 2 H), 3.72 (s, 6 H), 3.62-3.58 (m, 5 H), 3.22 (m, 2 H).

EXAMPLE 65

3-[2-amino-5-(2,3,4-trimethoxy-benzyl)-[1,2,4]triazolo[1,5-c]quinazolin-8-ylamino]-propan-1-ol

[(I); R1=8-C₃H₈NO, X=phenyl, Z=CH₂, W=3,4,5-trimethoxy-phenyl]

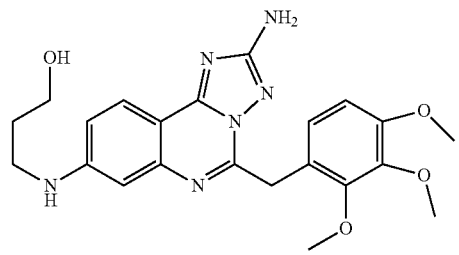 [SMILES: COc1ccc(Cc2nc3cc(NCCCO)ccc3c3nc(N)nn23)c(OC)c1OC]

Operating as in Example 64, but employing 3-hydroxy-propylamine instead of 2-hydroxy-ethylamine, the title compound was obtained in 18% yield.

1H-NMR (400 MHz), δ (ppm, DMSO-d₆): 7.86 (d, 1 H), 6.99 (dd, 1 H), 6.74-6.73 (m, 3 H), 6.48 (t, 1 H), 6.22 (bs, 2 H), 4.50 (t, 1 H), 4.34 (bs, 2 H), 3.72 (s, 6 H), 3.62 (s, 3 H), 3.53 (m, 2 H), 3.19 (m, 2 H), 1.74 (m, 2 H).

EXAMPLE 66

3-[2-amino-5-(4-benzyloxy-3-methoxy-benzyl)-[1,2,4]triazolo[1,5-c]quinazolin-8-ylamino]-propan-1-ol

[(I); R1=8-C₃H₈NO, X=phenyl, Z=CH₂, W=4-benzyloxy-3-trimethoxy-phenyl]

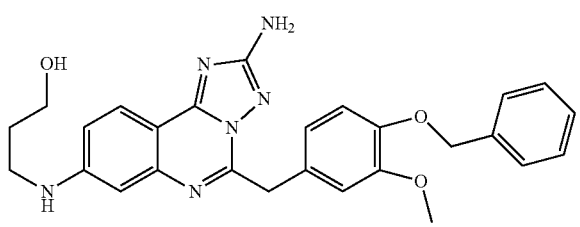 [SMILES: COc1cc(Cc2nc3cc(NCCCO)ccc3c3nc(N)nn23)ccc1OCc1ccccc1]

Operating as in Example 54, but employing 5-(4-benzyloxy-3-methoxy-benzyl)-8-fluoro-[1,2,4]triazolo[1,5-c]quinazolin-2-ylamine prepared as described in Example 34 instead of 5-benzo[1,3]dioxol-5-ylmethyl-8-fluoro-[1,2,4]triazolo[1,5-c]quinazolin-2-ylamine and 3-hydroxy-propylamine instead of morpholine, the title compound was obtained in 35% yield.

1H-NMR (400 MHz), δ (ppm, DMSO-d₆): 7.85 (d, 1 H), 7.41 (m, 2 H), 7.37 (m, 2 H), 7.31 (m, 1 H), 7.10 (d, 1 H), 6.98 (dd, 1 H), 6.94 (d, 1 H), 6.83 (dd, 1 H), 6.63 (d, 1 H), 6.48 (t, 1 H), 6.20 (bs, 2 H), 5.02 (s, 2 H), 4.50 (t, 1 H), 4.33 (bs, 2 H), 3.74 (s, 3 H), 3.53 (m, 2 H), 3.19 (m, 2 H), 1.74 (m, 2 H).

EXAMPLE 67

2-[2-amino-5-(4-benzyloxy-3-methoxy-benzyl)-[1,2,4]triazolo[1,5-c]quinazolin-8-ylamino]-ethanol

[(I); R1=8-C₂H₆NO, X=phenyl, Z=CH₂, W. 4-benzyloxy-3-trimethoxy-phenyl]

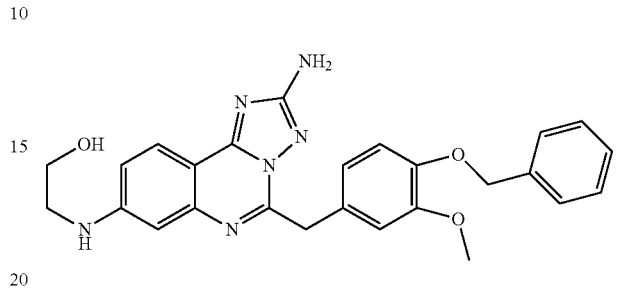

Operating as in Example 66, but employing 2-hydroxy-ethylamine instead of 3-hydroxy-propylamine, the title compound was obtained in 22% yield.

1H-NMR (400 MHz), δ (ppm, DMSO-d₆): 7.85 (d, 1 H), 7.41 (m, 2 H), 7.37 (m, 2 H), 7.31 (m, 1 H), 7.10 (d, 1 H), 7.02 (dd, 1 H), 6.95 (d, 1 H), 6.83 (dd, 1 H), 6.77 (d, 1 H), 6.48 (t, 1 H), 6.20 (bs, 2 H), 5.02 (s, 2 H), 4.75 (t, 1 H), 4.33 (bs, 2 H), 3.74 (s, 3 H), 3.61 (m, 2 H), 3.22 (m, 2 H).

EXAMPLE 68

2-(2-amino-5-benzo[1,3]dioxol-5-ylmethyl-8-fluoro-[1,2,4]triazolo[1,5-c]quinazolin-10-ylamino)-ethanol

[(I); R1=8-F, 10-C₂H₆NO, X=phenyl, Z=CH₂, W=benzo[1,3]dioxol-5-yl]

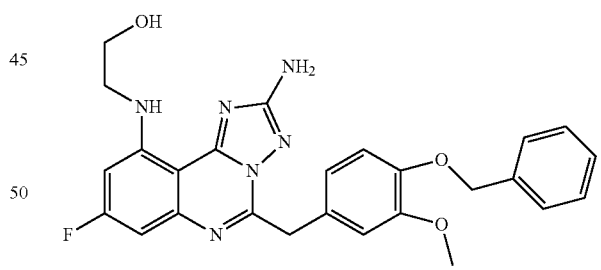

Operating as in Example 54, but employing 5-benzo[1,3]dioxol-5-ylmethyl-8,10-difluoro-[1,2,4]triazolo[1,5-c]quinazolin-2-ylamine prepared as described in Example 30 instead of 5-benzo[1,3]dioxol-5-ylmethyl-8-fluoro-[1,2,4]triazolo[1,5-c]quinazolin-2-ylamine and 2-hydroxy-ethylamine instead of morpholine, the title compound was obtained in 17% yield.

1H-NMR (400 MHz), δ (ppm, DMSO-d₆): 7.99 (t, 1 H), 6.97 (s, 1 H), 6.82-6.80 (m, 2 H), 6.73 (dd, 1 H), 6.61 (dd, 1 H), 6.48 (bs, 2 H), 5.96 (s, 2 H), 4.85 (t, 1 H), 4.36 (bs, 2 H), 3.66 (m, 2 H), 3.40 (m, 2 H).

EXAMPLE 69

5-benzo[1,3]dioxol-5-ylmethyl-8-fluoro-10-(4-methyl-piperazin-1-yl)-[1,2,4]triazolo[1,5-c]quinazolin-2-ylamine

[(I); R1=8-F, 10-$C_5H_{11}N_2$, X=phenyl, Z=$CH_2$, W=benzo[1,3]dioxol-5-yl]

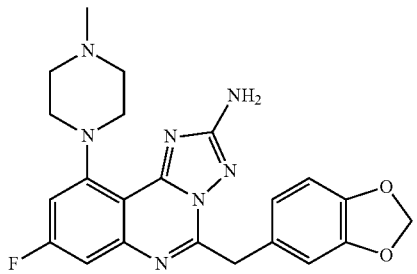 [SMILES: CN1CCN(c2cc(F)cc3nc(Cc4ccc5c(c4)OCO5)n4nc(N)nc4c23)CC1]

Operating as in Example 68, but employing N-methyl-piperazine instead of 2-hydroxy-ethylamine, the title compound was obtained in 23% yield.

1H-NMR (400 MHz), δ (ppm, DMSO-$d_6$): 7.19 (dd, 1 H), 7.01-6.97 (m, 2 H), 6.83-6.82 (m, 2 H), 6.33 (bs, 2 H), 5.96 (s, 2 H), 4.39 (bs, 2 H), 3.09 (m, 4 H), 2.64 (m, 4 H), 2.30 (s, 3 H).

EXAMPLE 70

5-benzo[1,3]dioxol-5-ylmethyl-8-fluoro-N-10-(2-morpholin-4-yl-ethyl)-[1,2,4]triazolo[1,5-c]quinazoline-2,10-diamine

[(I); R1=8-F, 10-$C_6H_{13}N_2O$, X=phenyl, Z=$CH_2$, W=benzo[1,3]dioxol-5-yl]

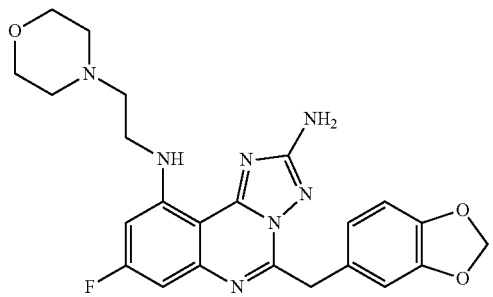 [SMILES: Nc1nc2c3c(NCCN4CCOCC4)cc(F)cc3nc(Cc3ccc4c(c3)OCO4)n2n1]

Operating as in Example 68, but employing 2-morpholin-4-yl-ethylamine instead of 2-hydroxy-ethylamine, the title compound was obtained in 11% yield.

1H-NMR (400 MHz), δ (ppm, DMSO-$d_6$): 8.03 (t, 1 H), 6.99 (s, 1 H), 6.84-6.83 (m, 2 H), 6.75 (dd, 1 H), 6.59 (dd, 1 H), 6.40 (bs, 2 H), 5.97 (s, 2 H), 4.37 (bs, 2 H), 3.61 (t, 4 H), 3.39 (m, 2 H), 2.65 (m, 2 H), 2.48 (t, 4 H).

EXAMPLE 71

5-benzo[1,3]dioxol-5-ylmethyl-8-fluoro-N-10-(2-pyrrolidin-1-yl-ethyl)-[1,2,4]triazolo[1,5-c]quinazoline-2,10-diamine [(I) R1=8-F, 10-$C_6H_{13}N_2$, X=phenyl, Z=$CH_2$, W=benzo[1,3]dioxol-5-yl]

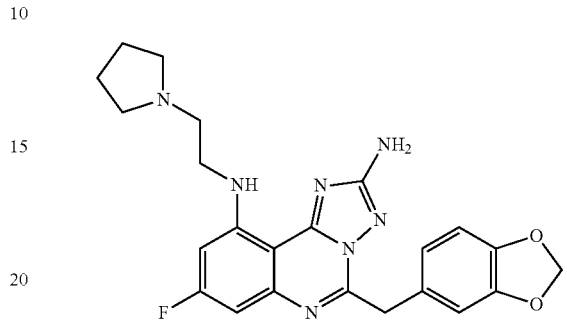

Operating as in Example 68, but employing 2-pyrrolidin-1-yl-ethylamine instead of 2-hydroxy-ethylamine, the title compound was obtained in 21% yield.

1H-NMR (400 MHz), δ (ppm, DMSO-$d_6$): 7.97 (t, 1 H), 6.96 (s, 1 H), 6.82-6.81 (m, 2 H), 6.73 (dd, 1 H), 6.58 (dd, 1 H), 6.43 (bs, 2 H), 5.96 (s, 2 H), 4.35 (bs, 2 H), 3.43 (m, 2 H), 2.76 (m, 2 H), 2.56 (m, 4 H), 1.71 (m, 4 H).

EXAMPLE 72

5-benzo[1,3]dioxol-5-ylmethyl-N-10-(2-dimethylamino-ethyl)-8-fluoro-[1,2,4]triazolo[1,5-c]quinazoline-2,10-diamine

[(I); R1=8-F, 10-$C_4H_{11}N_2$, X=phenyl, Z=$CH_2$, W=benzo[1,3]dioxol-5-yl]

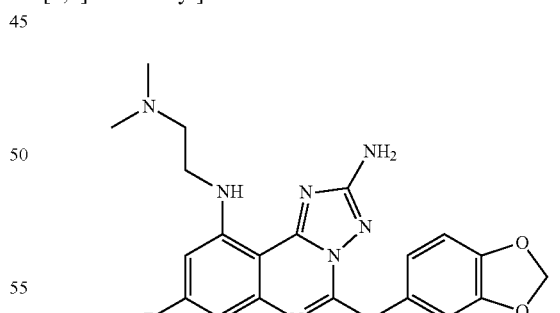

Operating as in Example 68, but employing 2-dimethylamino-1-yl-ethylamine instead of 2-hydroxy-ethylamine, the title compound was obtained in 20% yield.

1H-NMR (400 MHz), δ (ppm, DMSO-$d_6$): 7.96 (t, 1 H), 6.98 (s, 1 H), 6.83-6.82 (m, 2 H), 6.74 (dd, 1 H), 6.58 (dd, 1 H), 6.45 (bs, 2 H), 5.97 (s, 2 H), 4.37 (bs, 2 H), 3.38 (m, 2 H), 2.57 (t, 2 H), 2.25 (s, 6 H).

EXAMPLE 73

3-(2-amino-5-benzo[1,3]dioxol-5-ylmethyl-8-fluoro-[1,2,4]triazolo[1,5-c]quinazolin-10-ylamino)-propan-1-ol

[(I); R1=8-F, 10-C$_3$H$_8$NO, X=phenyl, Z=CH$_2$, W=benzo[1,3]dioxol-5-yl]

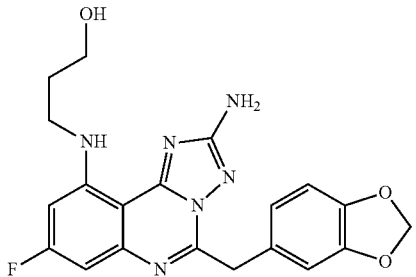 [SMILES: Nc1nc2c3c(NCCCO)cc(F)cc3nc(Cc3ccc4c(c3)OCO4)n2n1]

Operating as in Example 68, but employing 3-hydroxy-propylamine instead of 2-hydroxy-ethylamine, the title compound was obtained in 33% yield.

1H-NMR (400 MHz), δ (ppm, DMSO-d$_6$): 7.89 (t, 1 H), 6.97 (s, 1 H), 6.82-6.80 (m, 2 H), 6.73 (dd, 1 H), 6.57 (dd, 1 H), 6.51 (bs, 2 H), 5.96 (s, 2 H), 4.57 (t, 1 H), 4.36 (bs, 2 H), 3.57 (m, 2 H), 3.38 (m, 2 H), 1.81 (m, 2 H).

EXAMPLE 74

N*10*-(2-amino-ethyl)-5-benzo[1,3]dioxol-5-ylmethyl-8-fluoro-[1,2,4]triazolo[1,5-c]quinazoline-2,10-diamine

[(I); R1=8-F, 10-C$_2$H$_6$N$_2$, X=phenyl, Z=CH$_2$, W=benzo[1,3]dioxol-5-yl]

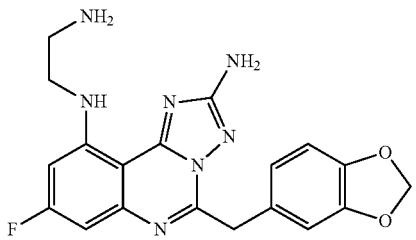 [SMILES: NCCNc1cc(F)cc2nc(Cc3ccc4c(c3)OCO4)n3nc(N)nc3c12]

Operating as in Example 68, but employing 1,2-diamino-ethane instead of 2-hydroxy-ethylamine, the title compound was obtained in 41% yield.

1H-NMR (400 MHz), δ (ppm, DMSO-d$_6$): 7.99 (t, 1 H), 6.97 (s, 1 H), 6.83-6.82 (m, 2 H), 6.73 (dd, 1 H), 6.62 (dd, 1 H), 6.51 (bs, 2 H), 5.97 (s, 2 H), 4.37 (bs, 2 H), 3.32 (m, 2 H), 2.84 (m, 2 H).

EXAMPLE 75

5-benzo[1,3]dioxol-5-ylmethyl-N-10-cyclopropyl-8-fluoro-[1,2,4]triazolo[1,5-c]quinazoline-2,10-diamine

[(I); R1=8-fluoro, 10-cyclopropylamino, X=phenyl, Z=CH$_2$, W=benzo[1,3]dioxol-5-yl]

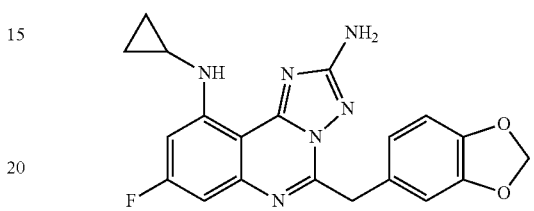

Operating as in Example 68, but employing cyclopropylamine instead of 2-hydroxy-ethylamine, the title compound was obtained in 18% yield.

1H-NMR (400 MHz), δ (ppm, DMSO-d$_6$): 8.02 (m, 1 H), 6.96 (s, 1 H), 6.84-6.77 (m, 4 H), 6.53 (bs, 2 H), 5.96 (s, 2 H), 4.36 (bs, 2 H), 2.64 (m, 1 H), 0.92 (m, 4 H).

EXAMPLE 76

5-benzo[1,3]dioxol-5-ylmethyl-8-fluoro-N*10*-(2-methoxy-ethyl)-[1,2,4]triazolo[1,5-c]quinazoline-2,10-diamine

[(I); R1=8-F, 10-C$_2$H$_6$N$_2$, X=phenyl, Z=CH$_2$, W=benzo[1,3]dioxol-5-yl]

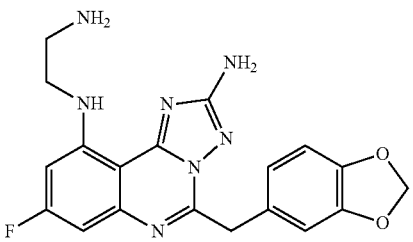 [SMILES: NCCNc1cc(F)cc2nc(Cc3ccc4c(c3)OCO4)n3nc(N)nc3c12]

Operating as in Example 68, but employing 2-methoxy-ethylamine instead of 2-hydroxy-ethylamine, the title compound was obtained in 41% yield.

1H-NMR (400 MHz), δ (ppm, DMSO-d$_6$): 7.96 (t, 1 H), 6.94 (s, 1 H), 6.80-6.79 (m, 2 H), 6.72 (dd, 1 H), 6.61 (dd, 1 H), 6.47 (bs, 2 H), 5.94 (s, 2 H), 4.33 (bs, 2 H), 3.57 (t, 2 H), 3.48 (m, 2 H), 3.29 (s, 3 H).

EXAMPLE 77

2-(2-amino-5-benzo[1,3]dioxol-5-ylmethyl-[1,2,4]triazolo[1,5-c]quinazolin-10-ylamino)-ethano

[(I); R1=10-C$_2$H$_6$NO, X=phenyl, Z=CH$_2$, W=benzo[1,3]dioxol-5-yl]

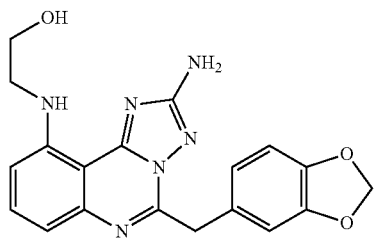 [SMILES: Nc1nc2c3c(NCCO)cccc3nc(Cc3ccc4c(c3)OCO4)n2n1]

Operating as in Example 54, but employing 5-benzo[1,3]dioxol-5-ylmethyl-10-fluoro-[1,2,4]triazolo[1,5-c]quinazolin-2-ylamine, prepared as described in Example 21, instead of 5-benzo[1,3]dioxol-5-ylmethyl-8-fluoro-[1,2,4]triazolo[1,5-c]quinazolin-2-ylamine and 2-hydroxy-ethylamine instead of morpholine, the title compound was obtained in 31% yield.

1H-NMR (400 MHz), δ (ppm, DMSO-d$_6$): 7.74 (t, 1 H), 7.53 (t, 1 H), 7.00 (d, 1 H), 6.97 (s, 1 H), 6.82-6.81 (m, 2 H), 6.72 (d, 1 H), 6.42 (bs, 2 H), 5.96 (s, 2 H), 4.82 (t, 1 H), 4.37 (bs, 2 H), 3.67 (m, 2 H), 3.40 (m, 2 H).

EXAMPLE 78

5-benzo[1,3]dioxol-5-ylmethyl-8-fluoro-N-10-dimethyl-[1,2,4]triazolo[1,5-c]quinazoline-2,10-diamine

[(I); R1=8-F, 10-C$_2$H$_6$N, X=phenyl, Z=CH$_2$, W=benzo[1,3]dioxol-5-yl]

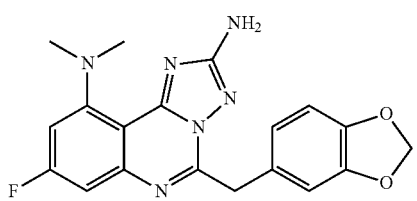 [SMILES: CN(C)c1cc(F)cc2nc(Cc3ccc4c(c3)OCO4)n3nc(N)nc3c12]

Operating as in Example 68, but employing dimethylamine instead of morpholine, the title compound was obtained in 43% yield.

1H-NMR (400 MHz), δ (ppm, DMSO-d$_6$): 7.13 (dd, 1 H), 6.99-6.96 (m, 2 H), 6.83-6.81 (m, 2 H), 6.40 (bs, 2 H), 5.96 (s, 2 H), 4.38 (bs, 2 H), 2.86 (s, 6 H).

Conversion of a compound of formula (I) into another compound of formula (I) as described under conversion (c)

EXAMPLE 79

2-amino-5-benzo[1,3]dioxol-5-ylmethyl-[1,2,4]triazolo[1,5-c]quinazoline-8-carboxylic acid-(2-hydroxy-ethyl)-amide

[(I); R1=8-CONHCH$_2$CH$_2$OH, X=phenyl, Z=CH$_2$, W=benzo[1,3]dioxol-5-yl]

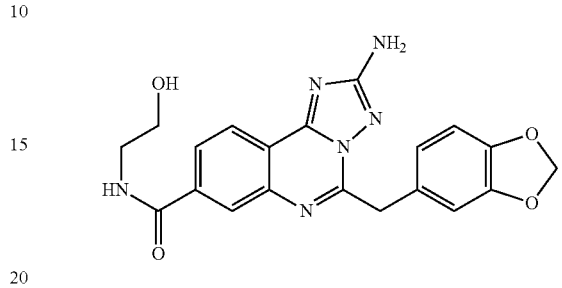

To a solution of 2-amino-5-benzo[1,3]dioxol-5-ylmethyl-[1,2,4]triazolo[1,5-c]quinazoline-8-carboxylic acid (0.05 g, 0.14 mmol) prepared as described in Example 19, and N,N-diisopropylethylamine (0.14 mL, 0.81 mmol) in anhydrous dichloromethane (5 mL), TBTU (0.05 g, 0.17 mmol) was added. The reaction was stirred at room temperature for 30 minutes, then 2-aminoethanol (0.02 mL, 0.28 mmol) was added. After stirring for 1 h, the solution washed with NaHCO$_3$ satured solution, then with water and brine. The organic phase was dried over Na$_2$SO$_4$ and evaporated to give a crude that was purified by flash column chromatography on silica gel eluting with DCM/MeOH/NH$_4$OH 8/2/1, to provide the title compound (0.03 g, 53% yield).

1H-NMR (400 MHz), δ (ppm, DMSO-d$_6$): 8.74 (t, 1 H), 8.36 (d, 1 H), 8.27 (d, 1 H), 8.09 (dd, 1 H), 7.02 (d, 1 H), 6.89-6.84 (m, 2 H), 6.54 (bs, 2 H), 5.98 (s, 2 H), 4.73 (t, 1 H), 4.45 (bs, 2 H), 3.55 (m, 2 H), 3.38 (m, 2 H).

EXAMPLE 80

2-amino-5-benzo[1,3]dioxol-5-ylmethyl-[1,2,4]triazolo[1,5-c]quinazoline-8-carboxylic acid (3-hydroxy-propyl)-amide

[(I); R1=8-CONHCH$_2$CH$_2$CH$_2$OH, X=phenyl, Z=CH$_2$, W=benzo[1,3]dioxol-5-yl]

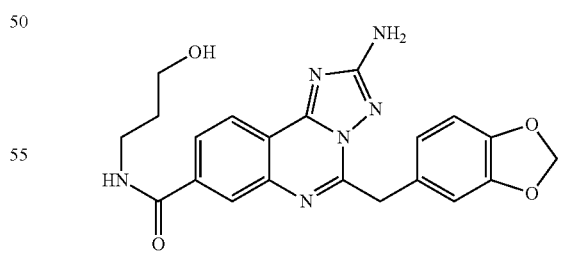

Operating as in Example 79, but employing 3-amino-propan-1-ol instead of 2-amino-ethan-1-ol, the title compound was obtained in 64% yield.

1H-NMR (400 MHz), δ (ppm, DMSO-d$_6$): 8.74 (t, 1 H), 8.34 (d, 1), 8.27 (d, 1 H), 8.08 (dd, 1 H), 7.01 (d, 1 H), 6.88-6.84 (m, 2 H), 6.54 (bs, 2 H), 5.98 (s, 2 H), 4.47-4.45 (m, 3 H), 3.49 (m, 2 H), 3.37 (m, 2 H), 1.71 (m, 2 H).

EXAMPLE 81

2-amino-5-benzo[1,3]dioxol-5-ylmethyl-[1,2,4]triazolo[1,5-c]quinazoline-8-carboxylic acid amide

[(I); R1=CONH$_2$, X=phenyl, Z=CH$_2$, W=benzo[1,3]dioxol-5-yl]

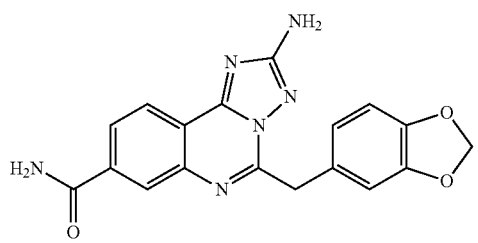 [SMILES: NC(=O)c1ccc2c(c1)nc(Cc1ccc3c(c1)OCO3)n1nc(N)nc21]

Operating as in Example 79, but employing ammonia instead of 2-amino-ethan-1-ol, the title compound was obtained in 75% yield.

1H-NMR (400 MHz), δ (ppm, DMSO-d$_6$): 8.39 (d, 1 H), 8.26-8.24 (m, 2 H), 8.10 (dd, 1 H), 7.58 (bs, 2 H), 7.01 (d, 1 H), 6.86-6.83 (m, 2 H), 6.54 (bs, 2 H), 5.97 (s, 2 H), 4.45 (bs, 2 H).

EXAMPLE 82

5-benzo[1,3]dioxol-5-ylmethyl-10-fluoro-8-(4-methyl-piperazin-1-yl)-[1,2,4]triazolo[1,5-c]quinazolin-2-ylamine

[(I); R1=8-C$_5$H$_{13}$N$_2$, 10-F, X=phenyl, Z=CH$_2$, W=benzo[1,3]dioxol-5-yl]

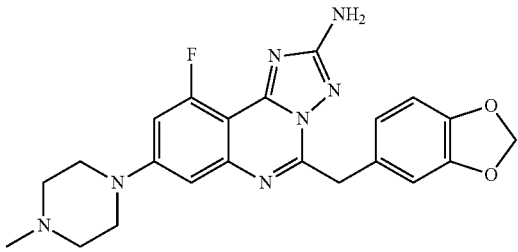 [SMILES: CN1CCN(c2cc(F)c3c(c2)nc(Cc2ccc4c(c2)OCO4)n2nc(N)nc32)CC1]

Scheme B

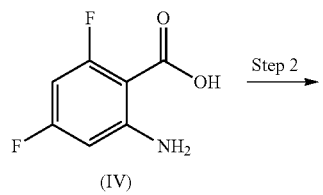

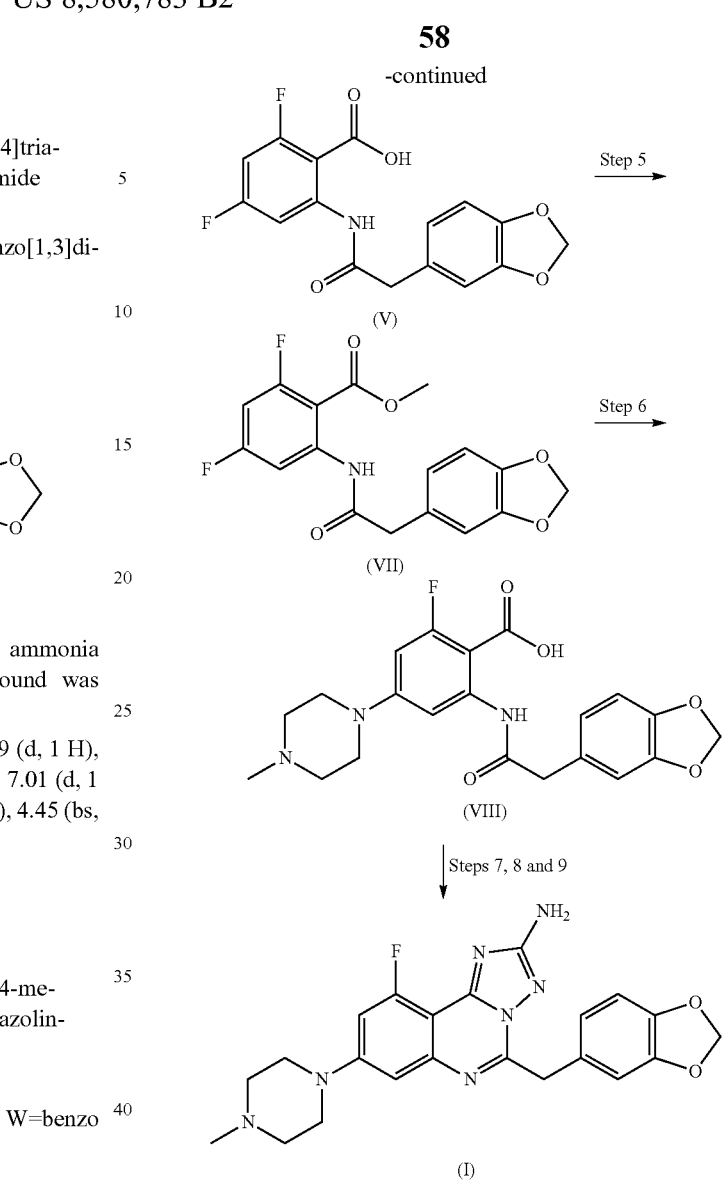

Step 2

2-(2-benzo[1,3]dioxol-5-yl-acetylamino)-4,6-difluoro-benzoic acid (V)

To a solution of commercially available benzo[1,3]dioxol-5-yl-acetyl chloride (3.70 g, 18.70 mmol) in anhydrous dichloromethane (20 mL) was added 2-amino-4,6-difluoro-benzoic acid (2.20 g, 12.5 mmol). After the addition of pyridine (5 mL), the mixture was heated under microwave condition at 120° C. for 5 minutes. The solvent was evaporated and the residue was diluted with 2 N HCl solution to induce the precipitation of a brown solid which was filtered, washed with water and dried under vacuum at 50° C., to afford the title compound (3.34 g, 80% yield).

1H-NMR (400 MHz), δ (ppm, DMSO-d$_6$): 12.21 (bs, 1 H), 10.65 (bs, 1 H), 7.93 (m, 1 H), 7.07 (m, 1 H), 6.90 (d, 1 H), 6.88 (d, 1 H), 6.80 (dd, 1 H), 5.99 (s, 2 H), 3.66 (bs, 2 H).

Step 5

2-(2-benzo[1,3]dioxol-5-yl-acetylamino)-4,6-difluoro-benzoic acid methyl ester (VII)

To a 0-5° C. cooled suspension of 2-(2-benzo[1,3]dioxol-5-yl-acetylamino)-4,6-difluoro-benzoic acid (0.50 g, 1.49 mmol) in dichloromethane (20 mL) was added 2 M (trimethylsilyl)diazomethane diethyl ether solution (0.82 mL, 1.64 mmol). The mixture was stirred at room temperature for 1 h, then the solvent was evaporated, to provide the title compound (0.52 g, 98% yield).

1H-NMR (400 MHz), δ (ppm, DMSO-$d_6$): 10.28 (bs, 1 H), 7.55 (m, 1 H), 7.15 (m, 1 H), 6.89-6.87 (m, 2H), 6.79 (dd, 1 H), 5.99 (s, 2H), 3.72 (s, 3 H), 3.60 (bs, 2 H).

Step 6

2-(2-benzo[1,3]dioxol-5-yl-acetylamino)-6-fluoro-4-(4-methyl-piperazin-1-yl)-benzoic acid methyl ester (VIII)

To a solution of 2-(2-benzo[1,3]dioxol-5-yl-acetylamino)-4,6-difluoro-benzoic acid methyl ester (0.50 g, 1.43 mmol) in dimethylsulfoxide (8 mL) was added N-methylpiperazine (0.20 mL, 2.86 mmol). The reaction was stirred at 80° C. for 3 h then cooled at room temperature. The solid precipitated was filtered and washed with a mixture $H_2O$/EtOH 1/1, to provide after drying the title compound (0.15 g, 25% yield).

1H-NMR (400 MHz), δ (ppm, DMSO-$d_6$): 10.52 (bs, 1 H), 7.58, (d, 1 H) 6.89-6.86 (m, 2 H), 6.78 (dd, 1 H), 6.59 (dd, 1 H), 5.99 (s, 2 H), 3.71 (s, 3 H), 3.60 (bs, 2 H), 3.28 (m, 4 H), 2.41 (m, 4 H), 2.22 (s, 3 H).

Steps 7, 8 and 9

5-benzo[1,3]dioxol-5-ylmethyl-10-fluoro-8-(4-methyl-piperazin-1-yl)-[1,2,4]triazolo[1,5-c]quinazolin-2-ylamine (I)

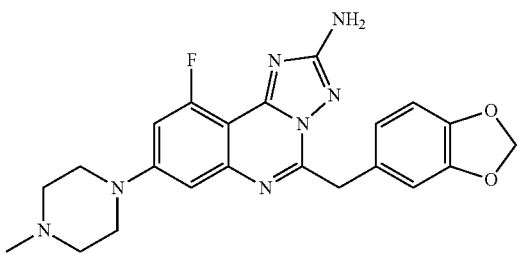 [SMILES: CN1CCN(c2cc(F)c3c(c2)nc(Cc2ccc4c(c2)OCO4)n2nc(N)nc32)CC1]

To a suspension of 2-(2-benzo[1,3]dioxol-5-yl-acetylamino)-6-fluoro-4-(4-methyl-piperazin-1-yl)-benzoic acid methyl ester (0.15 g, 0.35 mmol) in a mixture of tetrahydrofuran (10 mL), methanol (1 mL) and water (2 mL), was added lithium hydroxide (0.15 g, 3.49 mmol). The reaction was stirred at room temperature overnight then the solvent was evaporated. The residue was diluted with water and 2 N HCl solution was added until pH 7. The solid precipitated was filtered and washed with water to obtain the 2-(2-benzo[1,3]dioxol-5-yl-acetylamino)-6-fluoro-4-(4-methyl-piperazin-1-yl)-benzoic acid crude. 2-(2-Benzo[1,3]dioxol-5-yl-acetylamino)-6-fluoro-4-(4-methyl-piperazin-1-yl)-benzoic acid was suspended in acetic anhydride (3 mL) and the reaction mixture was heated under microwave condition at 130° C. for 10 minutes. The solvent was evaporated to obtain the 2-benzo[1,3]dioxol-5-ylmethyl-5-fluoro-7-(4-methyl-piperazin-1-yl)-benzo[d][1,3]oxazin-4-one crude. To a solution of 2-benzo[1,3]dioxol-5-ylmethyl-5-fluoro-7-(4-methyl-piperazin-1-yl)-benzo[d][1,3]oxazin-4-one in dry pyridine (3 mL) was added aminoguanidine hydrogencarbonate (0.05 g, 0.39 mmol) and the mixture was heated under microwave condition at 180° C. for 15 minutes. The reaction was cooled at room temperature and diluted with water to induce the precipitation of a brown solid which was washed with a mixture MeOH/$H_2O$ 8/2, to afford the title compound (0.07 g, 46% yield).

1H-NMR (400 MHz), δ (ppm, DMSO-$d_6$): 7.25 (dd, 1 H), 6.97-6.96 (m, 2 H), 6.83-6.82 (m, 2 H), 6.40 (bs, 2 H), 5.97 (s, 2 H), 4.34 (bs, 2 H), 3.37 (m, 4 H), 2.44 (m, 4 H), 2.22 (s, 3 H).

Conversion of a compound of formula (I) into another compound of formula (I) as described under conversion (h)

EXAMPLE 83

4-(2-amino-8-fluoro-[1,2,4]triazolo[1,5-c]quinazolin-5-ylmethyl)-2-methoxy-phenol

[(I); R1=8-F, X=phenyl, Z=$CH_2$, W=3-methoxy-4-hydroxy-phenyl]

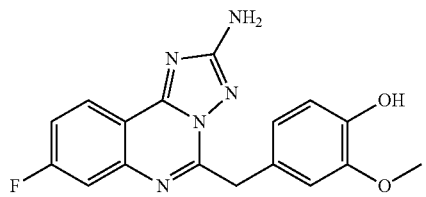 [SMILES: COc1cc(Cc2nc3cc(F)ccc3c3nc(N)nn23)ccc1O]

To a solution of 5-(4-benzyloxy-3-methoxy-benzyl)-8-fluoro-[1,2,4]triazolo[1,5-c]quinazolin-2-ylamine (0.04 g, 0.09 mmol) in MeOH (5 mL), prepared as described in example 34, were added 1,4-cyclohexadiene (0.1 mL, 1.40 mmol) and 10% Pd/C (0.02 g, 50% w/w). The reaction was heated at 70° C. for 1 h, then filtered through Celite® washing with MeOH and THF and evaporated, to afford the title compound (0.03 g, 97% yield).

1H-NMR (400 MHz), δ (ppm, DMSO-$d_6$): 8.84 (bs, 1 H), 8.26 (m, 1 H), 7.70 (dd, 1 H), 7.56 (m, 1 H), 7.04 (d, 1 H), 6.76 (dd, 1 H), 669 (d, 1 H), 6.50 (bs, 2 H), 4.39 (bs, 2 H), 3.72 (s, 3 H).

EXAMPLE 84

4-[2-amino-8-(2-hydroxy-ethylamino)-[1,2,4]triazolo[1,5-c]quinazolin-5-ylmethyl]-2-methoxy-phenol

[(I); R1=8-$C_2H_5NO$, X=phenyl, Z=$CH_2$, W=3-methoxy-4-hydroxy-phenyl]

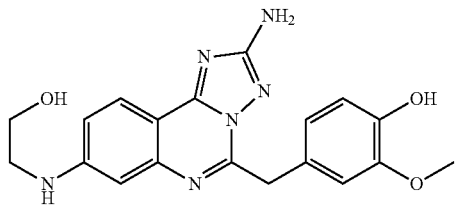 [SMILES: COc1cc(Cc2nc3cc(NCCO)ccc3c3nc(N)nn23)ccc1O]

Operating as in Example 83, but employing 5-(4-benzyloxy-3-methoxy-benzyl)-8-(2-hydroxy-ethylamino)-[1,2,4]triazolo[1,5-c]quinazolin-2-ylamine, prepared as described in Example 67, instead of 5-(4-benzyloxy-3-methoxy-benzyl)-8-fluoro-[1,2,4]triazolo[1,5-c]quinazolin-2-ylamine, the title compound was obtained in 86% yield.

1H-NMR (400 MHz), δ (ppm, DMSO-$d_6$): 8.81 (bs, 1 H), 7.85 (d, 1 H), 7.01-6.99 (m, 2 H), 6.77 (d, 1 H), 6.74 (dd, 1 H), 6.68 (d, 1 H), 6.47 (t, 1 H), 6.20 (bs, 2 H), 4.75 (t, 1 H), 4.28 (bs, 2 H), 3.72 (s, 3 H), 3.61 (m, 2 H), 3.22 (m, 2 H).

EXAMPLE 85

4-[2-amino-8-(3-hydroxy-propylamino)-[1,2,4]triazolo[1,5-c]quinazolin-5-ylmethyl]-2-methoxy-phenol

[(I); R1=8-C$_3$H$_7$NO, X=phenyl, Z=CH$_2$, W=3-methoxy-4-hydroxy-phenyl]

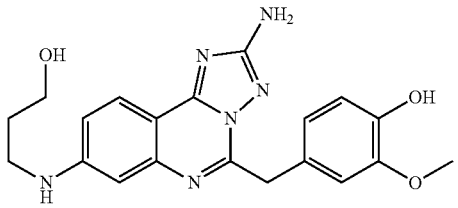 [SMILES: COc1cc(Cc2nc3cc(NCCCO)ccc3c3nc(N)nn23)ccc1O]

Operating as in Example 83, but employing 5-(4-benzyloxy-3-methoxy-benzyl)-8-(3-hydroxy-propylamino)-[1,2,4]triazolo[1,5-c]quinazolin-2-ylamine, prepared as described in Example 66, instead of 5-(4-benzyloxy-3-methoxy-benzyl)-8-fluoro-[1,2,4]triazolo[1,5-c]quinazolin-2-ylamine, the title compound was obtained in 91% yield.

1H-NMR (400 MHz), δ (ppm, DMSO-d$_6$): 8.80 (bs, 1 H), 7.85 (d, 1 H), 7.02 (d, 1 H), 6.98 (dd, 1 H), 6.74-6.72 (m, 2H), 6.68 (d, 1 H), 6.48 (t, 1 H), 6.19 (bs, 2 H), 4.51 (t, 1 H), 4.28 (bs, 2 H), 3.72 (s, 3 H), 3.53 (m, 2 H), 3.19 (m, 2 H), 1.74 (m, 2 H).

The invention claimed is:
1. A compound of the formula (I):

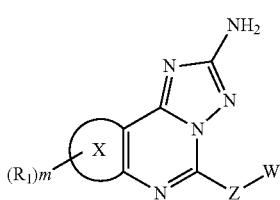

(I)

wherein:
m is 0, 1 or 2;
X is phenyl, naphtyl, pyridine, furan or thiophene;
any R1, if present, is independently halogen, trifluoromethyl, cyano, nitro, CONHRa, ORa, NRbRc, NHCORa, NHSO$_2$Ra, SO$_2$Rd, COORe or an optionally substituted group selected from linear or branched C$_1$-C$_7$ alkyl, C$_2$-C$_7$ alkenyl, C$_2$-C$_7$ alkynyl, C$_3$-C$_8$ cycloalkyl, C$_4$-C$_8$ cycloalkenyl and C$_4$-C$_8$ heterocyclyl,
wherein
Ra is hydrogen, trifluoromethyl or an optionally substituted group selected from linear or branched C$_1$-C$_7$ alkyl, C$_2$-C$_7$ alkenyl, C$_2$-C$_7$ alkynyl, C$_3$-C$_8$ cycloalkyl, C$_4$-C$_8$ cycloalkenyl, C$_4$-C$_8$ heterocyclyl, aryl and heteroaryl;
Rb and Rc, the same or different, are hydrogen or an optionally substituted group selected from linear or branched C$_1$-C$_7$ alkyl, C$_2$-C$_7$ alkenyl, C$_2$-C$_7$ alkynyl, C$_3$-C$_8$ cycloalkyl, C$_4$-C$_8$ cycloalkenyl, C$_4$-C$_8$ heterocyclyl, aryl and heteroaryl or Rb and Rc together with the nitrogen atom to which they are bonded form an optionally substituted heterocyclyl group comprising oxygen, sulfur or nitrogen atom,
Rd is an optionally substituted linear or branched C$_1$-C$_7$ alky,
Re is hydrogen or an optionally substituted linear or branched C$_1$-C$_7$ alky;
W is a substituted linear or branched C$_1$-C$_7$ alkyl or an optionally substituted aryl or heteroaryl, optionally fused with C$_3$-C$_8$ cycloalkyl or C$_4$-C$_8$ heterocyclyl;
Z is CH$_2$, CH(OR2) or CH(NHR3),
wherein
R2 is hydrogen or an optionally substituted linear or branched C$_1$-C$_7$ alky,
R3 is hydrogen or COR4, wherein R4 is O—C$_1$-C$_7$ Alkyl,
and pharmaceutically acceptable salts thereof,
provided that
5-benzyl-[1,2,4]triazolo[1,5-c]quinazolin-2-ylamine is excluded.

2. A compound of formula (I) according to claim 1, wherein X is phenyl and m, R1, Z and W are as defined in claim 1.

3. A compound of formula (I) according to claim 1 wherein Z is CH$_2$ and m, R1 and W are as defined in claim 1.

4. A compound of formula (I) according to claim 1 wherein W is an optionally substituted aryl, optionally fused with C$_3$-C$_8$ cycloalkyl or C$_4$-C$_8$ heterocyclyl, and m and R1 are as defined in claim 1.

5. A compound of formula (I) according to claim 1 which is selected from the group consisting of:
5-(3-bromo-4-methoxybenzyl)[1,2,4]triazolo[1,5-c]quinazolin-2-amine,
5-[3-(2-furyl)-4-methoxybenzyl][1,2,4]triazolo[1,5-c]quinazolin-2-amine,
4-[(2-amino[1,2,4]triazolo[1,5-c]quinazolin-5-yl)methyl]-2-bromophenol,
5-(1,3-benzodioxol-5-ylmethyl)-8-nitro[1,2,4]triazolo[1,5-c]quinazolin-2-amine,
tert-butyl[(S)-(2-amino[1,2,4]triazolo[1,5-c]quinazolin-5-yl)(phenyl)methyl]carbamate,
5-(1,3-benzodioxol-5-ylmethyl)[1,2,4]triazolo[1,5-c]quinazoline-2,8-diamine,
2-amino-5-(1,3-benzodioxol-5-ylmethyl)[1,2,4]triazolo[1,5-c]quinazoline-8-sulfonamide,
(R)-(2-amino[1,2,4]triazolo[1,5-c]quinazolin-5-yl)(phenyl)methanol,
5-(2,3-dihydro-1,4-benzodioxin-6-ylmethyl)[1,2,4]triazolo[1,5-c]quinazolin-2-amine,
5-[2-(benzyloxy)benzyl]-[1,2,4]triazolo[1,5-c]quinazolin-2-amine,
5-(2,3-dihydro-1-benzofuran-5-ylmethyl)[1,2,4]triazolo[1,5-c]quinazolin-2-amine,
(S)-(2-amino[1,2,4]triazolo[1,5-c]quinazolin-5-yl)(phenyl)methanol,
tert-butyl[(R)-(2-amino[1,2,4]triazolo[1,5-c]quinazolin-5-yl)(phenyl)methyl]carbamate,
2-amino-5-(1,3-benzodioxol-5-ylmethyl)[1,2,4]triazolo[1,5-c]quinazoline-9-carbonitrile,
5-(1,3-benzodioxol-5-ylmethyl)-8-fluoro[1,2,4]triazolo[1,5-c]quinazolin-2-amine,
5-[(R)-amino(phenyl)methyl][1,2,4]triazolo[1,5-e]quinazolin-2-amine,
5-(1,3-benzodioxol-5-ylmethyl)-8-(methylsulfonyl)[1,2,4]triazolo[1,5-c]quinazolin-2-amine,
5-[(6-iodo-1,3-benzodioxol-5-yl)methyl][1,2,4]triazolo[1,5-c]quinazolin-2-amine, 9-(aminomethyl)-5-(1,3-benzodioxol-5-ylmethyl)[1,2,4]triazolo[1,5-c]quinazolin-2-amine,
2-amino-5-(1,3-benzodioxol-5-ylmethyl)[1,2,4]triazolo[1,5-c]quinazolin-9-ol,
5-[(6-bromo-1,3-benzodioxol-5-yl)methyl][1,2,4]triazolo[1,5-c]quinazolin-2-amine,
2-amino[1,2,4]triazolo[1,5-c]quinazolin-5-ol,
5-(1,3-benzodioxol-5-ylmethyl)-10-fluoro[1,2,4]triazolo[1,5-c]quinazolin-2-amine,
N-[2-amino-5-(1,3-benzodioxol-5-ylmethyl)[1,2,4]triazolo[1,5-c]quinazolin-9-yl]acetamide,
5-(1,3-benzodioxol-5-ylmethyl)-8-bromo[1,2,4]triazolo[1,5-c]quinazolin-2-amine,
5-(1,3-benzodioxol-5-ylmethyl)-8-morpholin-4-yl[1,2,4]triazolo[1,5-e]quinazolin-2-amine,
2-amino-5-(1,3-benzodioxol-5-ylmethyl)[1,2,4]triazolo[1,5-c]quinazolin-7-ol,
5-(1,3-benzodioxol-5-ylmethyl)-8-(4-methylpiperazin-1-yl)[1,2,4]triazolo[1,5-c]quinazolin-2-amine,
2-{[2-amino-5-(1,3-benzodioxol-5-ylmethyl)[1,2,4]triazolo[1,5-c]quinazolin-8-yl]amino}ethanol,
5-(1,3-benzodioxol-5-ylmethyl)-N~8~-(2-morpholin-4-ylethyl)[1,2,4]triazolo[1,5-e]quinazoline-2,8-diamine,
5-(1,3-benzodioxol-5-ylmethyl)-N~8~-(2-pyrrolidin-1-ylethyl)[1,2,4]triazolo[1,5-c]quinazoline-2,8-diamine,
5-(1,3-benzodioxol-5-ylmethyl)-N~8~-[2-(dimethylamino)ethyl][1,2,4]triazolo[1,5-c]quinazoline-2,8-diamine,
5-(1,3-benzodioxol-5-ylmethyl)-N~8~-(2-methoxyethyl)[1,24]triazolo[1,5-c]quinazoline-2,8-diamine,
5-(1,3-benzodioxol-5-ylmethyl)-10-methoxy[1,2,4]triazolo[1,5-c]quinazolin-2-amine,
3-{[2-amino-5-(1,3-benzodioxol-5-ylmethyl)[1,2,4]triazolo[1,5-c]quinazolin-8-yl]amino}propan-1-ol,
N-8-(2-aminoethyl)-5-(1,3-benzodioxol-5-ylmethyl)[1,2,4]triazolo[1,5-c]quinazoline-2,8-diamine,
5-(1,3-benzodioxol-5-ylmethyl)-8,10-difluoro[1,2,4]triazolo[1,5-c]quinazolin-2-amine,
2-{[2-amino-5-(1,3-benzodioxol-5-ylmethyl)-8-fluoro[1,2,4]triazolo[1,5-e]quinazolin-10-yl]amino}ethanol,
N-10-(2-aminoethyl)-5-(1,3-benzodioxol-5-ylmethyl)-8-fluoro[1,2,4]triazolo[1,5-e]quinazoline-2,10-diamine,
3{-[2-amino-5-(1,3-benzodioxol-5-ylmethyl)-8-fluoro[1,2,4]triazolo[1,5-c]quinazolin-10-yl]amino}propan-1-ol,
5-(1,3-benzodioxol-5-ylmethyl)-N~10~-[2-(dimethylamino)ethyl]-8-fluoro[1,2,4]triazolo[1,5-c]quinazoline-2,10-diamine,
5-(1,3-benzodioxol-5-ylmethyl)-8-fluoro-N~10~-(2-pyrrolidin-1-ylethyl)[1,2,4]triazolo[1,5-c]quinazoline-2,10-diamine,
5-(1,3-benzodioxol-5-ylmethyl)-8-fluoro-N~10~-(2-morpholin-4-ylethyl)[1,2,4]triazolo[1,5-c]quinazoline-2,10-diamine,
5-(1,3-benzodioxol-5-ylmethyl)-8-fluoro-10-(4-methylpiperazin-1-yl)[1,2,4]triazolo[1,5-c]quinazolin-2-amine,
5-(1,3-benzodioxol-5-ylmethyl)-10-chloro[1,2,4]triazolo[1,5-c]quinazolin-2-amine,
5-(1,3-benzodioxol-5-ylmethyl)-N-10-cyclopropyl-8-fluoro[1,2,4]triazolo[1,5-c]quinazoline-2,10-diamine,
5-(1,3-benzodioxol-5-ylmethyl)-10-fluoro-8-(4-methylpiperazin-1-yl)[1,2,4]triazolo[1,5-c]quinazolin-2-amine,
2-amino-5-(1,3-benzodioxol-5-ylmethyl)[1,2,4]triazolo[1,5-e]quinazolin-8-ol,
5-(1,3-benzodioxol-5-ylmethyl)-8-fluoro-N~10~-(2-methoxyethyl)[1,2,4]triazolo[1,5-c]quinazoline-2,10-diamine,
2-amino-5-(1,3-benzodioxol-5-ylmethyl)-N-(2-hydroxyethyl)[1,2,4]triazolo[1,5-c]quinazoline-8-carboxamide,
2-amino-5-(1,3-benzodioxol-5-ylmethyl)[1,2,4]triazolo[1,5-c]quinazoline-8-carboxamide,
2-amino-5-(1,3-benzodioxol-5-ylmethyl)-N-(3-hydroxypropyl)[1,2,4]triazolo[1,5-c]quinazoline-8-carboxamide,
8-fluoro-5-[(5-methoxy-1H-indol-3-yl)methyl][1,2,4]triazolo[1,5-c]quinazolin-2-amine,
2-({2-amino-5-[(5-methoxy-1H-indol-3-yl)methyl][1,2,4]triazolo[1,5-c]quinazolin-8-yl}amino)ethanol,
8-fluoro-5-(3,4,5-trimethoxybenzyl)[1,2,4]triazolo[1,5-c]quinazolin-2-amine,
2-{[2-amino-5-(3,4,5-trimethoxybenzyl)[1,2,4]triazolo[1,5-c]quinazolin-8-yl]amino}ethanol,
3-{[2-amino-5-(3,4,5-trimethoxybenzyl)[1,2,4]triazolo[1,5-c]quinazolin-8-yl]amino}propan-1-ol,
2-{[2-amino-5-(1,3-benzodioxol-5-ylmethyl)[1,2,4]triazolo[1,5-c]quinazolin-10-yl]amino}ethanol,
2-[(2-amino-8-fluoro-5-propyl[1,2,4]triazolo[1,5-c]quinazolin-10-yl)amino]ethanol,
5-(1,3-benzodioxol-5-ylmethyl)-10-fluoro-8-(4-methylpiperazin-1-yl)[1,2,4]triazolo[1,5-c]quinazolin-2-amine trifluoroacetate,
5-[4-(benzyloxy)-3-methoxybenzyl]-8-fluoro[1,2,4]triazolo[1,5-c]quinazolin-2-amine,
8-fluoro-5-[4-(trifluoromethoxy)benzyl][1,2,4]triazolo[1,5-c]quinazolin-2-amine,
2-({2-amino-5-[4-(trifluoromethoxy)benzyl][1,2,4]triazolo[1,5-c]quinazolin-8-yl}amino)ethanol,
3-({2-amino-5-[4-(trifluoromethoxy)benzyl][1,2,4]triazolo[1,5-c]quinazolin-8-yl}amino)propan-1-ol,
3-({2-amino-5-[4-(benzyloxy)-3-methoxybenzyl][1,2,4]triazolo[1,5-c]quinazolin-8-yl}amino)propan-1-ol,
2-({2-amino-5-[4-(benzyloxy)-3-methoxybenzyl][1,2,4]triazolo[1,5-c]quinazolin-8-yl}amino)ethanol,
4-({2-amino-8-[(2-hydroxyethyl)amino][1,2,4]triazolo[1,5-c]quinazolin-5-yl}methyl)-2-methoxyphenol,
4-[(2-amino-8-fluoro[1,2,4]triazolo[1,5-c]quinazolin-5-yl)methyl]-2-methoxyphenol,
4-({2-amino-8-[(3-hydroxypropyl)amino][1,2,4]triazolo[1,5-c]quinazolin-5-yl}methyl)-2-methoxyphenol,
5-(1,3-benzodioxol-5-ylmethyl)-8-fluoro-N~10~,N~10~-dimethyl[1,2,4]triazolo[1,5-c]quinazoline-2,10-diamine,
5-(1,3-benzodioxol-5-ylmethyl)-8,10-dimethoxy[1,2,4]triazolo[1,5-c]quinazolin-2-amine,
5-[2-(3,5-dimethoxyphenyl)ethyl][1,2,4]triazolo[1,5-c]quinazolin-2-amine,
5-[2-(3,5-dimethoxyphenyl)ethyl]-8,10-difluoro[1,2,4]triazolo[1,5-c]quinazolin-2-amine,
2-({2-amino-5-[2-(3,5-dimethoxyphenyl)ethyl]-8-fluoro[1,2,4]triazolo[1,5-c]quinazolin-10-yl}amino)ethanol,
5-[2-(2-amino[1,2,4]triazolo[1,5-c]quinazolin-5-yl)ethyl]benzene-1,3-diol,
5-(2-{2-amino-8-fluoro-10-[(2-hydroxyethyl)amino][1,2,4]triazolo[1,5-c]quinazolin-5-yl}ethyl)benzene-1,3-diol and
{(2S)-1-[2-amino-5-(1,3-benzodioxol-5-ylmethyl)[1,2,4]triazolo[1,5-c]quinazolin-8-yl]pyrrolidin-2-yl}methanol.

6. A process for preparing a compound of the formula (I) as defined in claim 1, which process comprises:

1) reacting a compound of formula (II)

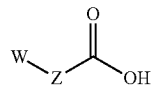
(II)

with $SOCl_2$, or $(COCl)_2$, or 2-(1H-7-azabenzotriazol-1-yl)-1,1,3,3-tetramethyl uronium hexafluorophosphate methanaminium, or O-(benzotriazol-1-yl)-N,N,N',N'-tetramethyluronium tetrafluoroborate or N,N'-dicyclohexylcarbodiimide; or N,N'-dicyclohexylcarbodiimide and pentafluorophenol; or N,N'-dicyclohexylcarbodiimide and 1-hydroxy-pirrolidine-2,5-dione;

2) condensing the resultant compound of formula (III)

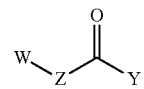
(III)

wherein Y is

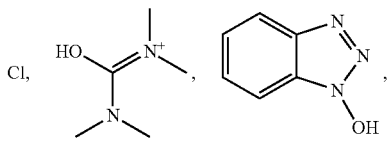

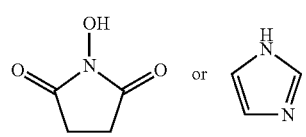

with a compound of formula (IV);

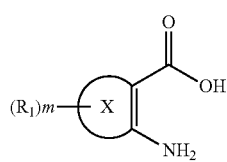
(IV)

3) reacting the resultant compound of formula (V)

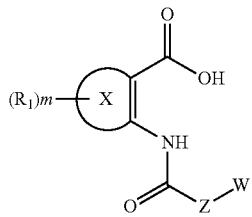
(V)

with $SOCl_2$, acetic or trifluoroacetic anhydride;

4) condensing the resultant compound of formula (VI)

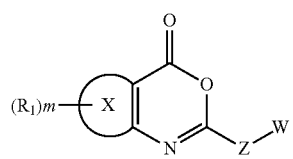
(VI)

with aminoguanidine hydrogencarbonate, to give a compound of formula (I) as defined above and optionally converting the resultant compound of the formula (I) as defined above into a different compound of the formula (I); and, if desired, converting a compound of formula (I) into a pharmaceutically acceptable salt thereof or converting a salt into the free compound (I).

7. A process according to claim 6 for preparing a compound of formula (I)A',

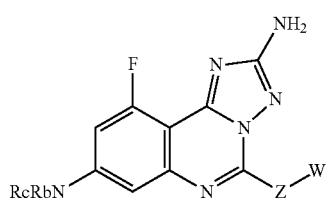
(I)A' characterized in that the process comprises the following steps:

5) reacting a compound of formula (V)A

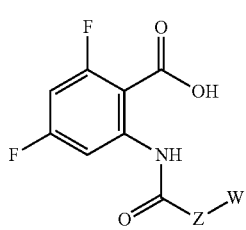
(V)A with diazomethane or trimethylsilyldiazomethane diethyl ether;

6) reacting the resultant compound of formula (VII)A

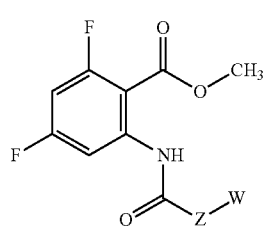
(VII)A with a compound of formula NHRbRc;
7) reacting the resultant compound of formula (VIII)A

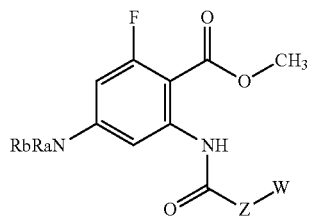
(VIII)A with NaOH or LiOH;
8) hydrolyzing the resultant compound of formula (IX)A

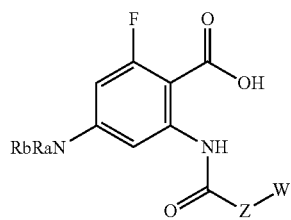
(IX)A with acetic or trifluoroacetic anhydride;

9) reacting the resultant compound of formula (X)A

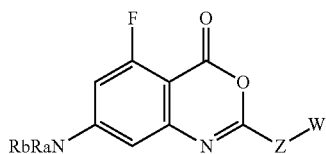
(X)A with aminoguanidine hydrogenocarbonate, to give a compound of formula (I)A' as defined above, and optionally converting the resultant compound of formula (I)A' as defined above into a different compound of formula (I)A; and, if desired, converting a compound of formula (I)A' into a pharmaceutically acceptable salt thereof or converting a salt into the free compound of formula (I)A.

8. A pharmaceutical composition comprising a therapeutically effective amount of a compound of formula (I), as defined in claim 1, and at least one pharmaceutically acceptable carrier and/or diluent.

9. A pharmaceutical composition according to claim 8 further comprising one or more chemotherapeutic agents.

10. A product comprising a compound of formula (I) as defined in claim 1 or a pharmaceutical composition comprising a therapeutically effective amount of said compound and at least one pharmaceutically acceptable carrier and/or diluent, and one or more chemotherapeutic agents, as a combined preparation for simultaneous, separate or sequential use in anticancer therapy.

11. An invitro method for inhibiting HSP90 activity which comprises contacting the said enzyme with an effective amount of a compound of formula (I) as defined in claim 1.

* * * * *